(12) United States Patent
Shioda et al.

(10) Patent No.: US 10,934,287 B2
(45) Date of Patent: Mar. 2, 2021

(54) FUSED HETEROCYCLIC COMPOUND AND COMPOSITION CONTAINING SAME

(71) Applicant: Sumitomo Chemical Company, Limited, Tokyo (JP)

(72) Inventors: Takayuki Shioda, Takarazuka (JP); Takeshi Tsuruda, Takarazuka (JP); Masaru Shimomura, Tokyo (JP)

(73) Assignee: SUMITOMO CHEMICAL COMPANY, LIMITED, Tokyo (JP)

( * ) Notice: Subject to any disclaimer, the term of this patent is extended or adjusted under 35 U.S.C. 154(b) by 0 days.

(21) Appl. No.: 16/495,460

(22) PCT Filed: Mar. 22, 2018

(86) PCT No.: PCT/JP2018/011444
§ 371 (c)(1),
(2) Date: Sep. 19, 2019

(87) PCT Pub. No.: WO2018/174170
PCT Pub. Date: Sep. 27, 2018

(65) Prior Publication Data
US 2020/0071320 A1    Mar. 5, 2020

(30) Foreign Application Priority Data

Mar. 23, 2017 (JP) .............................. JP2017-057088
Dec. 20, 2017 (JP) .............................. JP2017-243609

(51) Int. Cl.
| | |
|---|---|
| *C07D 471/04* | (2006.01) |
| *C07D 413/14* | (2006.01) |
| *A01N 43/54* | (2006.01) |
| *A01N 43/76* | (2006.01) |
| *A01N 43/50* | (2006.01) |
| *C07D 405/04* | (2006.01) |

(52) U.S. Cl.
CPC ............ *C07D 471/04* (2013.01); *A01N 43/50* (2013.01); *A01N 43/54* (2013.01); *A01N 43/76* (2013.01); *C07D 405/04* (2013.01); *C07D 413/14* (2013.01)

(58) Field of Classification Search
CPC ........ A01N 43/50; A01N 43/54; A01N 43/76; C07D 405/04; C07D 413/14
USPC ....................................................... 514/303
See application file for complete search history.

(56) References Cited

U.S. PATENT DOCUMENTS

| | | | | |
|---|---|---|---|---|
| 2014/0194290 A1* | 7/2014 | Takahashi | ............ | C07D 498/04 504/246 |
| 2015/0191474 A1* | 7/2015 | Takahashi | ............ | A61K 31/498 514/249 |
| 2016/0002260 A1* | 1/2016 | Tanabe | .................... | A01N 43/52 514/338 |
| 2016/0368915 A1 | 12/2016 | Tanabe et al. | | |
| 2018/0352811 A1 | 12/2018 | Yonemura et al. | | |
| 2020/0085051 A1* | 3/2020 | Tanaka | ............... | A61K 31/4439 |
| 2020/0165244 A1* | 5/2020 | Shioda | ................. | A61K 31/437 |

FOREIGN PATENT DOCUMENTS

| | | | | |
|---|---|---|---|---|
| EP | 3385261 A1 | 10/2018 | | |
| JP | 2017501176 A | 1/2017 | | |
| WO | 2004035563 A1 | 4/2004 | | |
| WO | 2007028135 A2 | 3/2007 | | |
| WO | 2012086848 A1 | 6/2012 | | |
| WO | 2013018928 A1 | 2/2013 | | |
| WO | 2015002211 A1 | 1/2015 | | |
| WO | 2015091945 A1 | 6/2015 | | |
| WO | 2016071214 A1 | 5/2016 | | |
| WO | 2017094750 A1 | 6/2017 | | |
| WO | WO-2018008727 A1 * | 1/2018 | ............. | A01N 43/54 |
| WO | WO-2018197315 A1 * | 11/2018 | ........... | C07D 471/04 |
| WO | WO-2019065568 A1 * | 4/2019 | ........... | C07D 213/84 |

(Continued)

OTHER PUBLICATIONS

English Translation of International Preliminary Report on Patentability dated Sep. 24, 2019 in International Application No. PCT/JP2018/011444.
English Translation of International Search Report dated May 29, 2018 in International Application No. PCT/JP2018/011444.
Extended European Search Report dated Nov. 18, 2020 in EP Application No. 18771072.8.

*Primary Examiner* — Daniel R Carcanague
(74) *Attorney, Agent, or Firm* — Panitch Schwarze Belisario & Nadel LLP

(57) ABSTRACT

A compound of formula (I) is provided. In the compound of formula (I), Q represents a group represented by formula Q1 or the like and the rest of the variable definitions are as set forth in the specification. The compounds of formula (I) have excellent control efficacy against harmful arthropods.

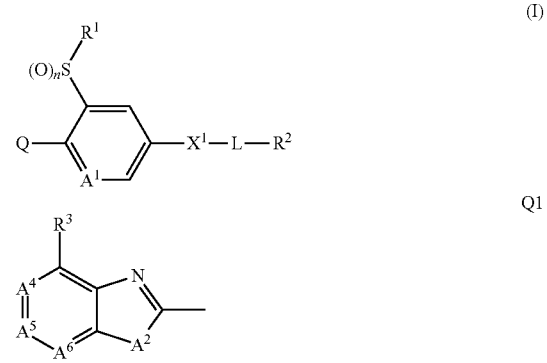

7 Claims, No Drawings

(56) References Cited

FOREIGN PATENT DOCUMENTS

| WO | WO-2019131575 A1 | * | 7/2019 | ............ | C07D 487/04 |
| WO | WO-2019131587 A1 | * | 7/2019 | ............ | C07D 487/04 |

* cited by examiner

FUSED HETEROCYCLIC COMPOUND AND COMPOSITION CONTAINING SAME

CROSS-REFERENCE TO RELATED APPLICATION

This application is a Section 371 of International Application No. PCT/JP2018/011444, filed Mar. 22, 2018, which was published in the Japanese language on Sep. 27, 2018, under International Publication No. WO 2018/174170 A1, which claims priority under 35 U.S.C. § 119(b) to Japanese Application No. 2017-057088 filed on Mar. 23, 2017 and Japanese Application No. 2017-243609 filed on Dec. 20, 2017, the disclosures of which are incorporated herein by reference in their entireties.

TECHNICAL FIELD

The present invention relates to a heterocyclic compound and a composition for controlling a harmful arthropod comprising the same.

BACKGROUND ART

To date, various compounds for controlling harmful arthropods have been studied and come into practical use.

Also, certain kinds of compounds are known to have pest control efficacies (for example, see Patent Documents 1 and 2).

CITATION LIST

Patent Document

Patent Document 1: WO 2012/086848 pamphlet
Patent Document 2: WO 2013/018928 pamphlet

SUMMARY OF THE INVENTION

Problems to be Solved by Invention

An object of the present invention is to provide a compound having excellent control efficacies against harmful arthropods.

Means to Solve Problems

The present invention provides the followings.
[1] A compound represented by formula (I)

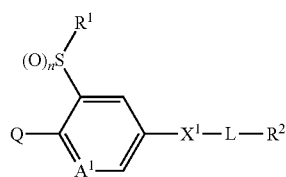

[wherein:

Q represents a group represented by formula Q1, a group represented by formula Q2, a group represented by formula Q3, a group represented by formula Q4, a group represented by formula Q5, a group represented by formula Q6, or a group represented by formula Q7;

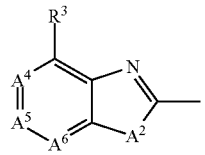

Q1

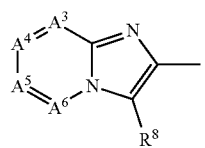

Q2

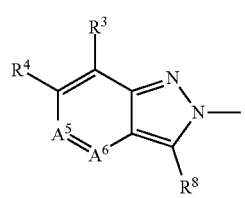

Q3

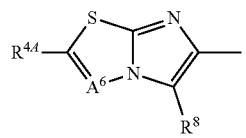

Q4

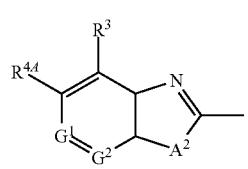

Q5

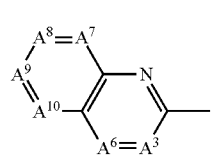

Q6

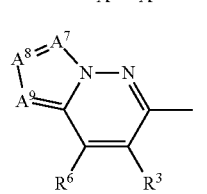

Q7

$A^1$ represents a $CR^7$ or a nitrogen atom;
$A^2$ represents a $NR^{8A}$, an oxygen atom, or a sulfur atom;
$A^3$ represents a nitrogen atom or a $CR^3$;
$A^4$ represents a nitrogen atom or a $CR^4$;
$A^5$ represents a nitrogen atom or a $CR^5$;
$A^6$ represents a nitrogen atom or a $CR^6$;
$A^7$ represents a nitrogen atom or a $CR^9$;
$A^8$ represents a nitrogen atom or a $CR^{10}$;
$A^9$ represents a nitrogen atom or a $CR^{11}$;
$A^{10}$ represents a nitrogen atom or a $CR^{12}$
(provided that
in the group represented by formula Q1, $A^4$ and $A^5$ do not each simultaneously represent a nitrogen atom,
in the group represented by formula Q2, $A^3$, $A^4$, $A^5$, and $A^6$ do not each simultaneously represent a nitrogen atom,
in the group represented by formula Q6, $A^3$ and $A^6$ do not each simultaneously represent a nitrogen atom, and $A^7$, $A^8$, $A^9$, and $A^{10}$ do not each simultaneously represent a nitrogen atom, and in the group represented by formula Q7, $A^7$, $A^8$, and $A^9$ do not each simultaneously represent a nitrogen atom);

$R^1$ represents a cyclopropyl group, a cyclopropylmethyl group, or a C1-C6 alkyl group optionally having one or more halogen atom(s);

$R^2$ represents a 5-10 membered heterocyclic group optionally having one or more substituent(s) selected from Group B;

$R^3$, $R^6$, $R^7$, and $R^9$ represent each independently a C1-C6 chain hydrocarbon group optionally having one or more halogen atom(s), a nitro group, a $OR^{13}$, a $NR^{14}R^{15}$, a cyano group, a halogen atom, or a hydrogen atom;

$R^{10}$, $R^{11}$, and $R^{12}$ represent each independently a C1-C6 chain hydrocarbon group optionally having one or more substituent(s) selected from Group C, a $OR^{16}$, a $S(O)_mR^{17}$, a $SF_5$, a halogen atom, or a hydrogen atom (wherein $R^{10}$ and $R^{11}$ do not each simultaneously represent a hydrogen atom);

$R^{4.4}$ represents a C1-C6 chain hydrocarbon group optionally having one or more substituent(s) selected from Group C, a $OR^{16}$, a $S(O)_mR^{17}$, a $SF_5$, or a halogen atom;

when $A^4$ represents a $CR^4$ and $A^5$ represents a $CR^5$, then $R^4$ represents a hydrogen atom, and $R^5$ represents a C1-C6 chain hydrocarbon group optionally having one or more substituent(s) selected from Group C, a $OR^{16}$, a $S(O)_mR^{17}$, a $SF_5$, or a halogen atom;

$R^5$ represents a hydrogen atom, and $R^4$ represents a C1-C6 chain hydrocarbon group optionally having one or more substituent(s) selected from Group C, a $OR^{16}$, a $S(O)_mR^{17}$, a $SF_5$, or a halogen atom; or $R^4$ and $R^5$ may be combined with the carbon atom to which they are attached to form a benzene ring, a 5-6 membered aromatic heterocyclic ring (wherein said benzene ring and said 5-6 membered aromatic heterocyclic ring may optionally have one or more substituent(s) selected from Group B), or a 5-8 membered nonaromatic heterocyclic ring optionally having one or more substituent(s) selected from Group E;

when $A^4$ represents a nitrogen atom and $A^5$ represents a $CR^5$, then $R^5$ represents a C1-C6 chain hydrocarbon group optionally having one or more substituent(s) selected from Group C, a $OR^{16}$, a $S(O)_mR^{17}$, a $SF_5$, or a halogen atom;

when $A^5$ represents a nitrogen atom and $A^4$ represents a $CR^4$, then $R^4$ represents a C1-C6 chain hydrocarbon group optionally having one or more substituent(s) selected from Group C, a $OR^{16}$, a $S(O)_mR^{17}$, a $SF_5$, or a halogen atom;

$R^8$ represents a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{18}$, a $C(O)OR^{18}$, or a hydrogen atom;

$R^{8.4}$ represents a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{18}$, or a $C(O)OR^{18}$;

$G^1$ represents a $NR^{19}$ and $G^2$ represents a $C(X^2)$; $G^1$ represents a $C(X^2)$ and $G^2$ represents a $NR^{19}$; or $G^1$ represents a $NR^{19}$ and $G^2$ represents a $NR^{20}$;

$R^{19}$ and $R^{20}$ represent each independently a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{21}$, a $C(O)OR^{21}$, or a hydrogen atom;

$R^{13}$, $R^{14}$, $R^{15}$, $R^{16}$, $R^{17}$, $R^{18}$, and $R^{21}$ represent each independently a C1-C6 chain hydrocarbon group optionally having one or more halogen atom(s), or a hydrogen atom;

$X^1$ and $X^2$ represent each independently an oxygen atom or a sulfur atom;

L represents a single bond or a $CH_2$;

m and n represent each independently 0, 1, or 2;

Group B: a group consisting of a C1-C6 chain hydrocarbon group optionally having one or more halogen atom(s), a hydroxy group, a C1-C6 alkoxy group optionally having one or more halogen atom(s), a C3-C6 alkenyloxy group optionally having one or more halogen atom(s), a C3-C6 alkynyloxy group optionally having one or more halogen atom(s), a sulfanyl group, a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a $NR^{22}R^{23}$, a $C(O)R^{22}$, a $OC(O)R^{22}$, a $C(O)OR^{22}$, a cyano group, a nitro group, and a halogen atom {wherein $R^{22}$ and $R^{23}$ represent each independently a C1-C6 chain hydrocarbon group optionally having one or more halogen atom(s), or a hydrogen atom};

Group C: a group consisting of a C1-C6 alkoxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C2-C6 alkylcarbonyl group optionally having one or more halogen atom(s), a C2-C6 alkoxycarbonyl group optionally having one or more halogen atom(s), a C3-C6 cycloalkyl group optionally having one or more halogen atom(s) or one or more C1-C3 alkyl group(s), a nitro group, a cyano group, a hydroxy group, and a halogen atom;

Group D: a group consisting of a C1-C6 alkoxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C2-C6 alkylcarbonyl group optionally having one or more halogen atom(s), a C2-C6 alkoxycarbonyl group optionally having one or more halogen atom(s), a C3-C6 cycloalkyl group optionally having one or more halogen atom(s) or one or more C1-C3 alkyl group(s), a phenyl group optionally having one or more substituent(s) selected from Group C, a 5-6 membered heterocyclic group optionally having one or more substituent(s) selected from Group C, a cyano group, a hydroxy group, and a halogen atom;

Group E: a group consisting of a C1-C3 alkyl group optionally having one or more halogen atom(s), a C1-C3 alkoxy group optionally having one or more halogen atom(s), a $NR^{24}R^{25}$, a C1-C3 alkylsulfanyl group optionally having one or more halogen atom(s), a C1-C3 alkylsulfinyl group optionally having one or more halogen atom(s), a C1-C3 alkylsulfonyl group optionally having one or more halogen atom(s), a C2-C4 alkylcarbonyl group optionally having one or more halogen atom(s), a C2-C4 alkoxycarbonyl group optionally having one or more halogen atom(s), a nitro group, a cyano group, a halogen atom, an oxo group, a thioxo group, and a $=NOR^{26}$ {wherein $R^{24}$ and $R^{25}$ represent each independently a hydrogen atom or a C1-C6 chain hydrocarbon group optionally having one or more halogen atom(s), and $R^{26}$ represents a C1-C6 alkyl group optionally having one or more halogen atom(s) or a hydrogen atom}}] (hereinafter referred to as "Present compound").

[2] The compound according to [1], wherein Q represents a group represented by formula Q1.

[3] The compound according to [1] or [2], wherein $A^4$ represents a $CR^4$, $X^1$ represents an oxygen atom, and L represents a single bond.

[4] The compound according to any one of [1] to [3], wherein $R^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group {wherein said pyridyl group, said pyrimidinyl group, said pyrazinyl group, said pyridazinyl group, said pyrazolyl group, said imidazolyl group, said triazolyl group, said oxazolyl group, said thiazolyl group, said thiadiazolyl group, and said isoxazolyl group may optionally have one or more substituent(s) selected from Group B}.

[5] A composition for controlling a harmful arthropod comprising the compound according to any one of [1] to [4] and an inert carrier.

[6] A method for controlling a harmful arthropod which comprises applying an effective amount of the compound according to any one of [1] to [4] to a harmful arthropod or a habitat where a harmful arthropod lives.

[7] A composition comprising one or more ingredient(s) selected from the group consisting of Group (a), Group (b), Group (c), Group (d), and Group (e), and the compound according to any one of [1] to [4];

Group (a): a group consisting of an insecticidal active ingredient, a miticidal active ingredient, and a nematicidal active ingredient;

Group (b): a fungicidal active ingredient;

Group (c): a plant growth regulatory ingredient;

Group (d): a phytotoxicity-reducing ingredient;

Group (e): a synergist.

Effect of Invention

According to the present invention, harmful arthropods can be controlled.

MODE FOR CARRYING OUT THE INVENTION

The substituent(s) in the present invention is/are explained as follows.

The term of "halogen atom" represents a fluorine atom, a chlorine atom, a bromine atom, or an iodine atom.

When a substituent has two or more halogen atoms, these halogen atoms may be identical to or different from each other.

When a substituent has two or more C1-C3 alkyl groups, these C1-C3 alkyl groups may be identical to or different from each other.

When a group "optionally having one or more substituent(s) selected from Group X" (wherein X represents any one of B to E) as described herein has two or more substituents selected from Group X, these substituents may be identical to or different from each other.

The expression of "CX-CY" as described herein means that the number of carbon atom is X to Y. For example, the expression of "C1-C6" means that the number of carbon atom is 1 to 6.

The term of "chain hydrocarbon group" represents an alkyl group, an alkenyl group, or an alkynyl group.

Examples of the term of "alkyl group" include a methyl group, an ethyl group, a propyl group, an isopropyl group, a 1,1-dimethylpropyl group, a 1,2-dimethylpropyl group, a 1-ethylpropyl group, a butyl group, a sec-butyl group, a tert-butyl group, a pentyl group, and a hexyl group.

Examples of the term of "alkenyl group" include a vinyl group, a 1-propenyl group, a 2-propenyl group, a 1-methyl-1-propenyl group, a 1-methyl-2-propenyl group, a 1,2-dimethyl-1-propenyl group, a 1-ethyl-2-propenyl group, a 3-butenyl group, a 4-pentenyl group, and a 5-hexenyl group.

Examples of the term of "alkynyl group" include an ethynyl group, a 1-propynyl group, a 2-propynyl group, a 1-methyl-2-propynyl group, a 1,1-dimethyl-2-propynyl group, a 1-ethyl-2-propynyl group, a 2-butynyl group, a 4-pentynyl group, and a 5-hexynyl group.

The term of "alkoxy group" refers to a monovalent group wherein an oxygen atom is bound to the above alkyl group.

The term of "C3-C6 cycloalkyl group" represents a cyclopropyl group, a cyclobutyl group, a cyclopentyl group, and a cyclohexyl group.

The term of "heterocyclic group" represents an aromatic heterocyclic group or a nonaromatic heterocyclic group. Examples of the aromatic heterocyclic group include a pyrrolyl group, a furyl group, a thienyl group, a pyrazolyl group, an imidazolyl group, a triazolyl group, a tetrazolyl group, an oxazolyl group, an isoxazolyl group, a thiazolyl group, an isothiazolyl group, an oxadiazolyl group, a thiadiazolyl group, a pyridyl group, a pyridazinyl group, a pyrimidinyl group, a pyrazinyl group, and a quinolyl group. Examples of the nonaromatic heterocyclic group include a pyrrolidinyl group, an imidazolinyl group, an imidazolidinyl group, a tetrahydrofuranyl group, a piperidyl group, a tetrahydropyrimidinyl group, a hexahydropyrimidinyl group, a piperazinyl group, an azepanyl group, an oxazolidinyl group, an isoxazolidinyl group, a 1,3-oxazinanyl group, a morpholinyl group, a 1,4-oxazepanyl group, a thiazolidinyl group, an isothiazolidinyl group, a 1,3-thiazinanyl group, a thiomorpholinyl group, and a 1,4-thiazepanyl group.

The term of "5-6 membered aromatic heterocyclic ring" represents a pyrrole ring, a furan ring, a thiophene ring, a pyrazole ring, an imidazole ring, a triazole ring, a tetrazole ring, an oxazole ring, an isoxazole ring, a thiazole ring, an isothiazole ring, an oxadiazole ring, a thiadiazole ring, a pyridine ring, a pyridazine ring, a pyrimidine ring, or a pyrazine ring.

The term of "5-8 membered nonaromatic heterocyclic ring" represents a pyrrolidine ring, an imidazoline ring, an imidazolidine ring, a tetrahydrofuran ring, a piperidine ring, a tetrahydropyrimidine ring, a hexahydropyrimidine ring, a piperazine ring, an azepane ring, an oxazolidine ring, an isoxazolidine ring, a 1,3-oxazinane ring, a morpholine ring, a 1,4-oxazepane ring, a thiazolidine ring, an isothiazolidine ring, a 1,3-thiazinane ring, a thiomorpholine ring, and a 1,4-thiazepane ring.

Embodiments of the Present compound include the following compounds.

Embodiment 1

The Present compound, wherein $R^1$ and $R^{8.4}$ represent each independently a C1-C6 alkyl group;

$R^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group {wherein said pyridyl group, said pyrimidinyl group, said pyrazinyl group, said pyridazinyl group, said pyrazolyl group, said imidazolyl group, said triazolyl group, said oxazolyl group, said thiazolyl group, said thiadiazolyl group, and said isoxazolyl group may optionally have one or more substituent(s) selected from Group B};

$R^3$, $R^5$, and $R^7$ represent each a hydrogen atom;

$R^4$ and $R^{4A}$ represent each independently a C1-C6 chain hydrocarbon group optionally having one or more halogen atom(s) or a $S(O)_2CF_3$; and $R^{10}$ and $R^{11}$ represent each independently a hydrogen atom, a C1-C6 chain hydrocarbon group optionally having one or more halogen atom(s), or a $S(O)_2CF_3$ (wherein $R^{10}$ and $R^{11}$ do not each simultaneously represent a hydrogen atom).

Embodiment 2

The Present compound, wherein Q represents a group represented by formula Q1.

Embodiment 3

The Present compound according to Embodiment 2, wherein $R^1$ and $R^{8A}$ represent each independently a C1-C6 alkyl group;

$R^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group {wherein said pyridyl group, said pyrimidinyl group, said pyrazinyl group, said pyridazinyl group, said pyrazolyl group, said imidazolyl group, said triazolyl group, said oxazolyl group, said thiazolyl group, said thiadiazolyl group, and said isoxazolyl group may optionally have one or more substituent(s) selected from Group B}; and $R^3$ and $R^7$ represent each a hydrogen atom.

Embodiment 4

The Present compound according to Embodiment 2, wherein $R^1$ represents an ethyl group;

$R^{8A}$ represents a methyl group;

$R^2$ represents a pyridyl group, a pyrimidinyl group, a pyrazolyl group, or a thiazolyl group {wherein said pyridyl group, said pyrimidinyl group, said pyrazolyl group, and said thiazolyl group may optionally have one or more substituent(s) selected from Group B}; and $R^3$ and $R^7$ represent each a hydrogen atom.

Embodiment 5

The Present compound according to Embodiment 3, wherein $R^4$ represents a C1-C6 chain hydrocarbon group optionally having one or more halogen atom(s) or a $S(O)_2CF_3$; and $R^5$ represents a hydrogen atom.

Embodiment 6

The Present compound according to Embodiment 4, wherein $R^4$ represents a C1-C6 chain hydrocarbon group optionally having one or more halogen atom(s) or a $S(O)_2CF_3$; and $R^5$ represents a hydrogen atom.

Embodiment 7

The Present compound according to Embodiment 2, wherein $A^4$ represents a $CR^4$;
$A^5$ represents a $CR^5$; and
$A^6$ represents a nitrogen atom.

Embodiment 8

The Present compound according to Embodiment 5, wherein $A^4$ represents a $CR^4$;
$A^5$ represents a $CR^5$; and
$A^6$ represents a nitrogen atom.

Embodiment 9

The Present compound according to Embodiment 6, wherein $A^4$ represents a $CR^4$;
$A^5$ represents a $CR^5$; and
$A^6$ represents a nitrogen atom.

Embodiment 10

The Present compound according to Embodiment 2, wherein $A^4$ represents a $CR^4$;
$A^5$ represents a nitrogen atom; and
$A^6$ represents a $CR^6$.

Embodiment 11

The Present compound according to Embodiment 3, wherein $A^4$ represents a $CR^4$;
$A^5$ represents a nitrogen atom;
$A^6$ represents a $CR^6$;
$R^4$ represents a C1-C6 chain hydrocarbon group optionally having one or more halogen atom(s) or a $S(O)_2CF_3$; and
$R^6$ represents a hydrogen atom.

Embodiment 12

The Present compound according to Embodiment 4, wherein $A^4$ represents a $CR^4$;
$A^5$ represents a nitrogen atom;
$A^6$ represents a $CR^6$;
$R^4$ represents a C1-C6 chain hydrocarbon group optionally having one or more halogen atom(s) or a $S(O)_2CF_3$; and
$R^6$ represents a hydrogen atom.

Embodiment 13

The Present compound according to Embodiment 2, wherein $A^4$ represents a $CR^4$; and
$A^5$ and $A^6$ represent each a nitrogen atom.

Embodiment 14

The Present compound according to Embodiment 3, wherein $A^4$ represents a $CR^4$;
$A^5$ and $A^6$ represent each a nitrogen atom; and

9

$R^4$ represents a C1-C6 chain hydrocarbon group optionally having one or more halogen atom(s) or a $S(O)_2CF_3$.

Embodiment 15

The Present compound according to Embodiment 4, wherein
$A^4$ represents a $CR^4$;
$A^5$ and $A^6$ represent each a nitrogen atom; and
$R^4$ represents a C1-C6 chain hydrocarbon group optionally having one or more halogen atom(s) or a $S(O)_2CF_3$.

Embodiment 16

The Present compound according to any one of Embodiments 1 to 15, wherein $X^1$ represents an oxygen atom.

Embodiment 17

The Present compound according to any one of Embodiments 1 to 15, wherein L represents a single bond.

Embodiment 18

The Present compound according to any one of Embodiments 1 to 15, wherein $A^1$ represents a nitrogen atom.

Embodiment 19

The Present compound according to any one of Embodiments 1 to 15, wherein
$A^1$ represents a nitrogen atom; and
n represents 2.

Embodiment 20

The Present compound according to any one of Embodiments 1 to 15, wherein
L represents a single bond;
$A^1$ represents a nitrogen atom; and
n represents 2.

Embodiment 21

The Present compound according to any one of Embodiments 1 to 15, wherein
$X^1$ represents an oxygen atom;
$A^1$ represents a nitrogen atom; and
n represents 2.

Embodiment 22

The Present compound according to any one of Embodiments 1 to 15, wherein
$X^1$ represents an oxygen atom;
L represents a single bond; and
$A^1$ represents a nitrogen atom.

Embodiment 23

The Present compound according to any one of Embodiments 1 to 15, wherein
$X^1$ represents an oxygen atom;
L represents a single bond;
$A^1$ represents a nitrogen atom; and
n represents 2.

10

Next, processes for preparing the Present compound are described.

Process 1

The Present compound may be prepared by reacting a compound represented by formula (M-1) (hereinafter referred to as "Compound (M-1)") with a compound represented by formula (M-2) (hereinafter referred to as "Compound (M-2)") in the presence of a base.

[wherein $X^a$ represents a fluorine atom, a chlorine atom, or a bromine atom; and the other symbols are the same as defined above.]

The reaction is usually carried out in a solvent. Examples of the solvent to be used in the reaction include ethers such as tetrahydrofuran (hereinafter referred to as "THF"), 1,4-dioxane, ethylene glycol dimethyl ether, and methyl tert-butyl ether (hereinafter referred to as "MTBE") (hereinafter collectively referred to as "ethers"); aromatic hydrocarbons such as toluene and xylene (hereinafter collectively referred to as "aromatic hydrocarbons"); aprotic polar solvents such as N-methylpyrrolidone (hereinafter referred to as "NMP") and dimethyl sulfoxide (hereinafter referred to as "DMSO") (hereinafter collectively referred to as "aprotic polar solvents"); halogenated hydrocarbons such as dichloromethane and chloroform (hereinafter collectively referred to as "halogenated hydrocarbons"); nitriles such as acetonitrile (hereinafter referred to as "nitriles"); water; and mixed solvents thereof.

Examples of the base to be used in the reaction include organic bases such as triethylamine, diisopropylethylamine, pyridine, and 4-(dimethylamino)pyridine (hereinafter collectively referred to as "organic bases"); and alkali metal carbonates such as sodium carbonate and potassium carbonate (hereinafter collectively referred to as "alkali metal carbonates").

In the reaction, the Compound (M-2) is usually used at a ratio of 1 to 10 mol, and the base is usually used at a ratio of 0.1 to 5 mol, relative to 1 mol of the Compound (M-1).

The reaction temperature is usually within the range of −20° C. to 150° C. The reaction time is usually within the range of 0.5 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Present compound.

Process 2

The Present compound may be prepared by reacting a compound represented by formula (M-3) (hereinafter referred to as "Compound (M-3)") with a compound represented by formula (M-4) (hereinafter referred to as "Compound (M-4)") in the presence of a base.

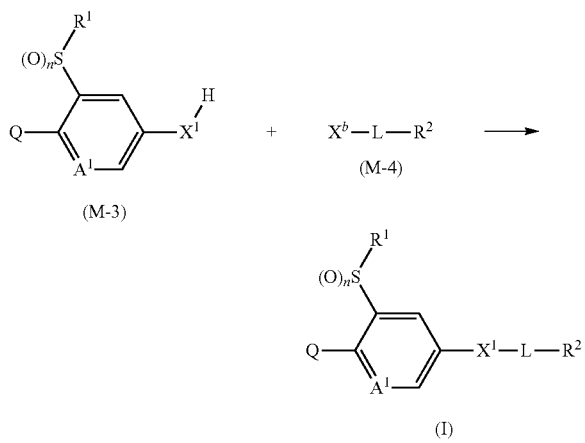

[wherein $X^b$ represents a chlorine atom, a bromine atom, or an iodine atom; and the other symbols are the same as defined above.]

The reaction is usually carried out in a solvent. Examples of the solvent to be used in the reaction include ethers, aromatic hydrocarbons, aprotic polar solvents, water, and mixed solvents thereof.

Examples of the base to be used in the reaction include alkali metal carbonates and sodium hydride.

A metal catalyst and a ligand may be added to the reaction as needed.

Examples of the metal catalyst to be used in the reaction include copper catalysts such as copper(I) iodide and copper (I) bromide.

When a metal catalyst is used in the reaction, examples of the base to be used in the reaction include organic bases, alkali metal carbonates, and tripotassium phosphate.

Examples of the ligand to be used in the reaction include 2-pyridinecarboxylic acid, 1-butylimidazole, 2,2'-bipyridine, 2-aminoethanol, and 1,10-phenanthroline.

In the reaction, the Compound (M-4) is usually used at a ratio of 1 to 10 mol, and the base is usually used at a ratio of 0.1 to 5 mol, relative to 1 mol of the Compound (M-3).

When a metal catalyst and a ligand are used in the reaction, the metal catalyst is usually used at a ratio of 0.01 to 0.5 mol, and the ligand is usually used at a ratio of 0.01 to 0.5 mol, relative to 1 mol of the Compound (M-3).

The reaction temperature is usually within the range of −20° C. to 200° C. The reaction time is usually within the range of 0.5 to 48 hour(s).

When the reaction is completed, the reaction mixture may be subjected to a work-up such as adding water to the reaction mixture, extracting the resulting reaction mixture with organic solvent(s), and drying or concentrating the resulting organic layer to give the Present compound.

Reference Process 1

A compound represented by formula (M-2a) (hereinafter referred to as "Compound (M-2a)") may be prepared by reacting a compound represented by formula (M-4a) (hereinafter referred to as "Compound (M-4a)") in the presence of water and a base.

[wherein the symbols are the same as defined above.]

The reaction is usually carried out in a solvent. Examples of the solvent to be used in the reaction include ethers, aromatic hydrocarbons, aprotic polar solvents, water, and mixed solvents thereof.

Examples of the base to be used in the reaction include alkali metal carbonates.

In the reaction, the base is usually used at a ratio of 0.1 to 5 mol, relative to 1 mol of the Compound (M-4a).

The reaction temperature is usually within the range of −20° C. to 200° C. The reaction time is usually within the range of 0.5 to 48 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-2a).

Reference Process 2

A compound represented by formula (M-2b) (hereinafter referred to as "Compound (M-2b)") may be prepared by hydrolyzing a compound represented by formula (M-5) (hereinafter referred to as "Compound (M-5)") in the presence of a base.

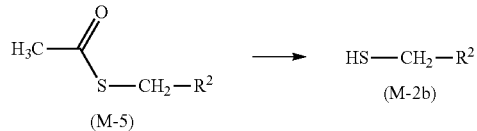

[wherein the symbol is the same as defined above.]

The reaction is usually carried out in a solvent. Examples of the solvent to be used in the reaction include ethers, aromatic hydrocarbons, aprotic polar solvents, water, and mixed solvents thereof.

Examples of the base to be used in the reaction include alkali metal hydroxides such as sodium hydroxide (hereinafter collectively referred to as "alkali metal hydroxides") and alkali metal carbonates.

In the reaction, the base is usually used at a ratio of 0.1 to 20 mol, relative to 1 mol of the Compound (M-5).

The reaction temperature is usually within the range of −20° C. to 200° C. The reaction time is usually within the range of 0.5 to 48 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-2b).

Reference Process 3

The Compound (M-5) may be prepared by reacting the Compound (M-4a) with S-potassium thioacetate.

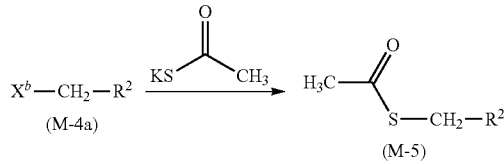

[wherein the symbols are the same as defined above.]

The reaction is usually carried out in a solvent. Examples of the solvent to be used in the reaction include ethers, aprotic polar solvents, water, and mixed solvents thereof.

In the reaction, the S-potassium thioacetate is usually used at a ratio of 0.1 to 5 mol, relative to 1 mol of the Compound (M-4a).

Reference Process 5

A compound represented by formula (M-1c) may be prepared by oxidizing a compound represented by formula (M-1a) (hereinafter referred to as "Compound (M-1a)") or a compound represented by formula (M-1b) (hereinafter referred to as "Compound (M-1b)"). The Compound (M-1b) may be prepared by oxidizing the Compound (M-1a).

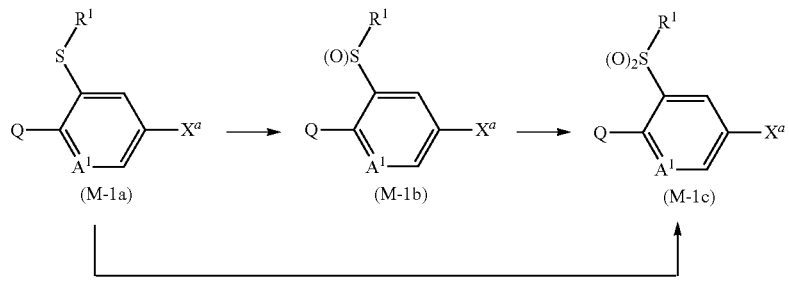

The reaction temperature is usually within the range of −20° C. to 200° C. The reaction time is usually within the range of 0.5 to 48 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-5).

Reference Process 4

The Compound (M-4a) may be prepared by reacting a compound represented by formula (M-6) (hereinafter referred to as "Compound (M-6)") with a halogenating agent in the presence of a radical initiator.

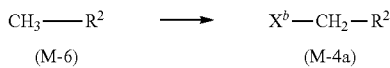

[wherein the symbols are the same as defined above.]

The reaction is usually carried out in a solvent. Examples of the solvent to be used in the reaction include ethers, halogenated hydrocarbons, nitriles, and mixed solvents thereof.

The halogenating agent to be used in the reaction is N-chlorosuccinimide, N-bromosuccinimide, or N-iodosuccinimide.

Examples of the radical initiator to be used in the reaction include benzoyl peroxide and azobisisobutyronitrile (AIBN).

In the reaction, the halogenating agent is usually used at a ratio of 0.5 to 1.5 mol, and the radical initiator is usually used at a ratio of 0.01 to 5 mol, relative to 1 mol of the Compound (M-6).

The reaction temperature is usually within the range of −20° C. to 150° C. The reaction time is usually within the range of 0.1 to 24 hour(s).

When the reaction is completed, the reaction mixture may be subjected to a work-up such as adding water to the reaction mixture, extracting the resulting reaction mixture with organic solvent(s), and drying or concentrating the resulting organic layer to give the Compound (M-4a).

The Compound (M-6) is a commercially available compound or may be prepared according to a known method.

[wherein the symbols are the same as defined above.]

These reactions may be carried out according to the methods described in WO 2013/018928 pamphlet.

Reference Process 6

The Compound (M-1a) may be prepared by reacting a compound represented by formula (M-7) (hereinafter referred to as "Compound (M-7)") with a compound represented by formula (M-12) (hereinafter referred to as "Compound (M-12)") in the presence of a base.

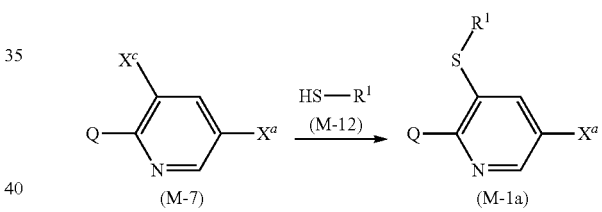

[wherein $X^c$ represents a fluorine atom or a chlorine atom; and the other symbols are the same as defined above.]

The reaction may be carried out according to the method described in WO 2013/018928 pamphlet.

The Compound (M-7) and the Compound (M-12) are commercially available compounds or may be prepared according to known methods.

Reference Process 7

A compound represented by formula (M-7Q1) may be prepared by cyclizing a compound represented by formula (M-8) (hereinafter referred to as "Compound (M-8)")

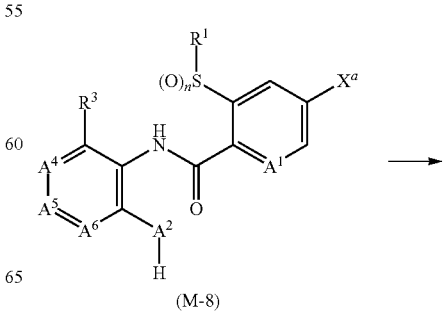

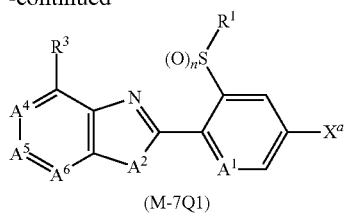

(M-7Q1)

[wherein the symbols are the same as defined above.]

The reaction may be carried out according to the methods described in WO 2013/018928 pamphlet and WO 2016/005263 pamphlet.

Reference Process 8

The Compound (M-8) may be prepared by reacting a compound represented by formula (M-9) (hereinafter referred to as "Compound (M-9)") with a compound represented by formula (M-10) (hereinafter referred to as "Compound (M-10)").

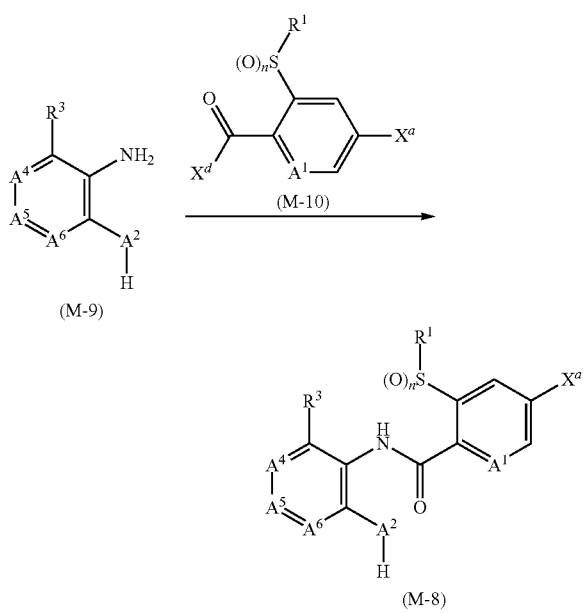

(M-9)

(M-10)

(M-8)

[wherein $X^d$ represents a hydroxy group or a chlorine atom; and the other symbols are the same as defined above.]

This reaction may be carried out according to the method described in WO 2013/018928 pamphlet.

The Compound (M-9) and the Compound (M-10) are commercially available compounds or may be prepared according to known methods.

Reference Process 9

A compound represented by formula (M-7Q2a) (hereinafter referred to as "Compound (M-7Q2a)") may be prepared according to the following scheme.

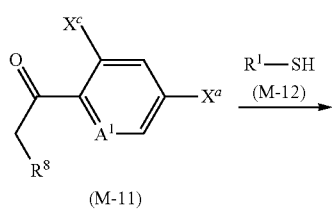

(M-11)

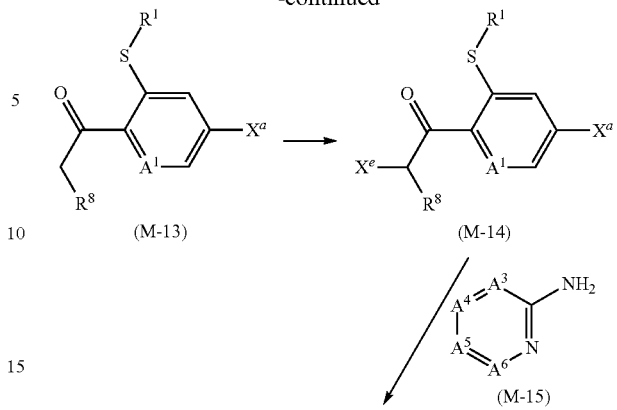

(M-13) (M-14)

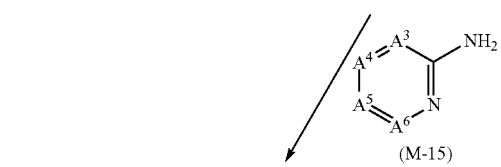

(M-15)

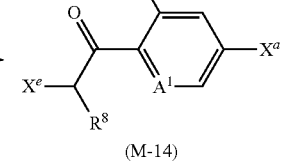

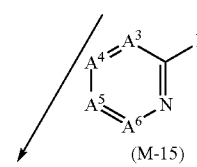

(M-7Q2a)

[wherein $X^e$ represents a chlorine atom or a bromine atom; and the other symbols are the same as defined above.]

The Compound (M-7Q2a) may be prepared by reacting a compound represented by formula (M-14) (hereinafter referred to as "Compound (M-14)") with a compound represented by formula (M-15) (hereinafter referred to as "Compound (M-15)").

The Compound (M-14) may be prepared by reacting a compound represented by formula (M-13) (hereinafter referred to as "Compound (M-13)") with a chlorinating agent or a brominating agent.

The Compound (M-13) may be prepared by reacting a compound represented by formula (M-11) (hereinafter referred to as "Compound (M-11)") with the Compound (M-12).

These reactions may be carried out according to the methods described in WO 2013/191113 pamphlet.

The Compound (M-11) and the Compound (M-15) are commercially available compounds or may be prepared according to known methods.

Reference Process 10

A compound represented by formula (M-7Q2c) (hereinafter referred to as "Compound (M-7Q2c)") may be prepared by oxidizing the Compound (M-7Q2a) or a compound represented by formula (M-7Q2b) (hereinafter referred to as "Compound (M-7Q2b)"). The Compound (M-7Q2b) may be prepared by oxidizing the Compound (M-7Q2a).

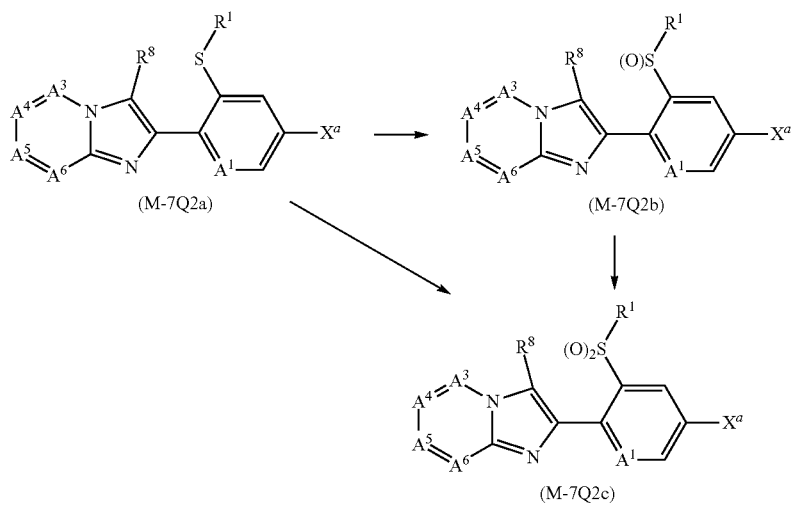

[wherein the symbols are the same as defined above.]

These reactions may be carried out according to the methods described in the Reference process 5.

Reference Process 11

A compound represented by formula (M-7Q3) (hereinafter referred to as "Compound (M-7Q3)") may be prepared according to the following scheme.

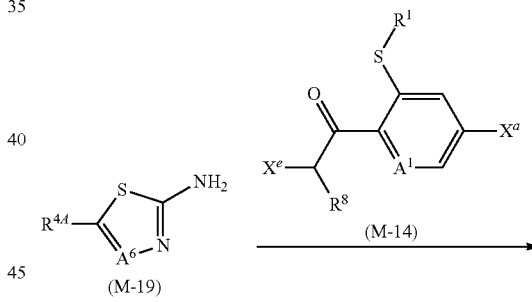

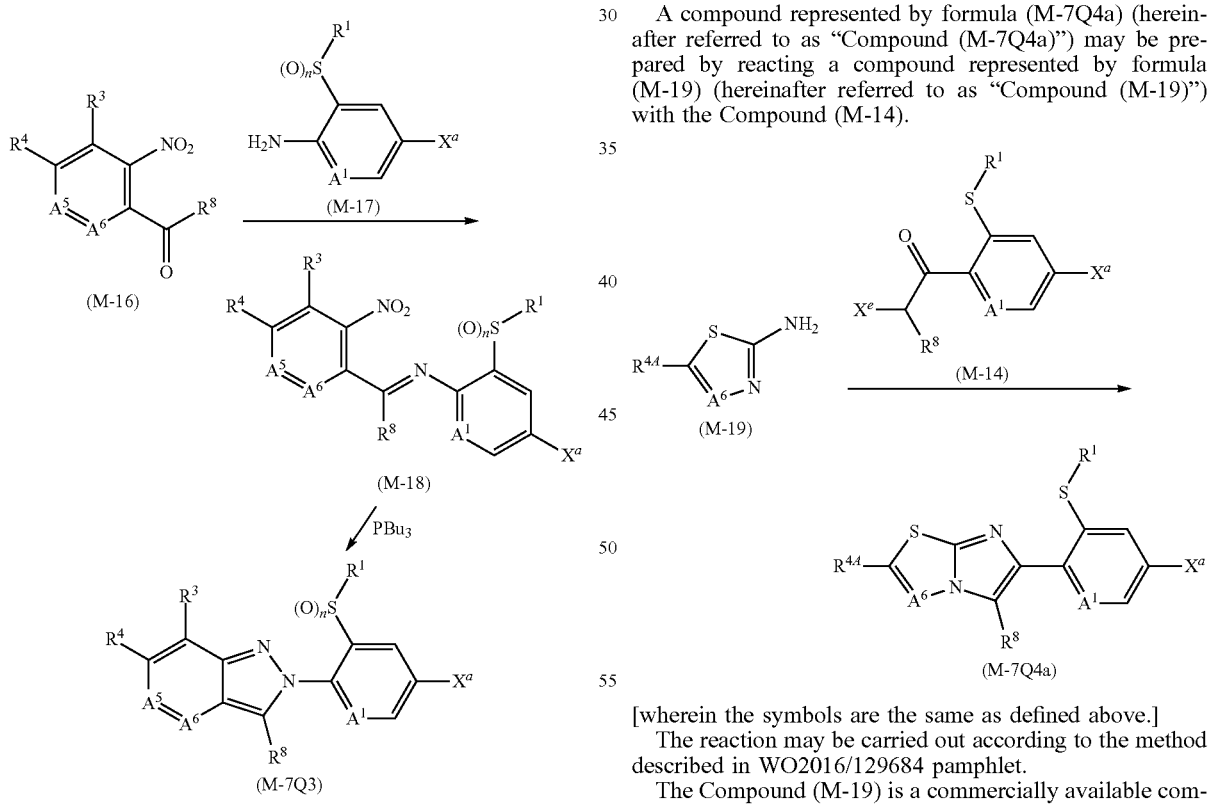

[wherein the symbols are the same as defined above.]

A compound represented by formula (M-18) (hereinafter referred to as "Compound (M-18)") may be prepared by reacting a compound represented by formula (M-16) (hereinafter referred to as "Compound (M-16)") with a compound represented by formula (M-17) (hereinafter referred to as "Compound (M-17)").

The Compound (M-7Q3) may be prepared by reacting the Compound (M-18) with tributylphosphine.

These reactions may be carried out according to the methods described in Organic Letters, 2014, 16(11), 3114.

The Compound (M-16) and the Compound (M-17) are commercially available compounds or may be prepared according to known methods.

Reference Process 12

A compound represented by formula (M-7Q4a) (hereinafter referred to as "Compound (M-7Q4a)") may be prepared by reacting a compound represented by formula (M-19) (hereinafter referred to as "Compound (M-19)") with the Compound (M-14).

[wherein the symbols are the same as defined above.]

The reaction may be carried out according to the method described in WO2016/129684 pamphlet.

The Compound (M-19) is a commercially available compound or may be prepared according to a known method.

Reference Process 13

A compound represented by formula (M-7Q4c) may be prepared by oxidizing the Compound (M-7Q4a) or a compound represented by formula (M-7Q4b) (hereinafter referred to as "Compound (M-7Q4b)"). The Compound (M-7Q4b) may be prepared by oxidizing the Compound (M-7Q4a).

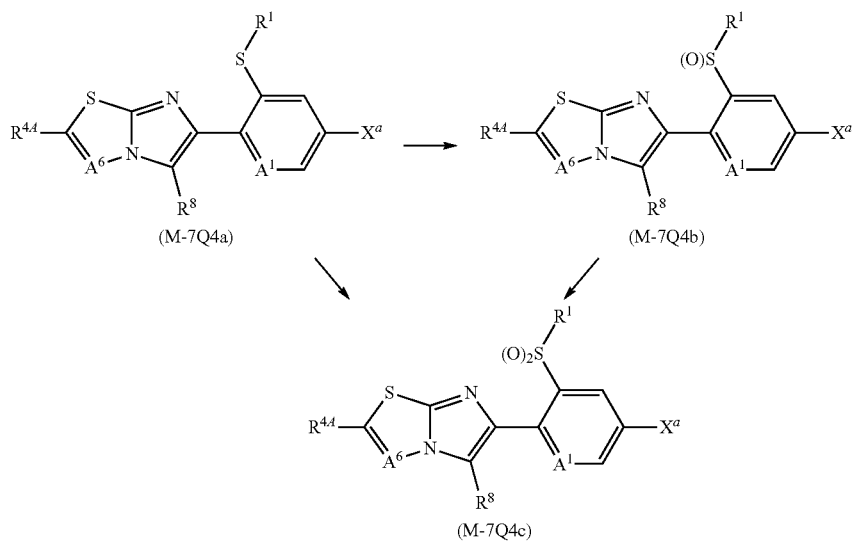

(M-7Q4a) → (M-7Q4b)

(M-7Q4c)

[wherein the symbols are the same as defined above.]

These reactions may be carried out according to the methods described in the Reference process 5.

Reference Process 14

A compound represented by formula (M-7Q5a) (hereinafter referred to as "Compound (M-7Q5a)") may be prepared according to the following scheme.

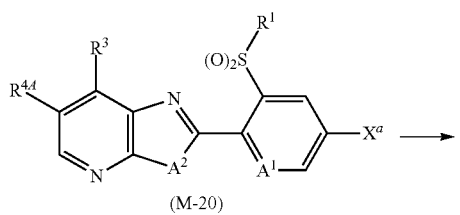

(M-20)

(M-21)

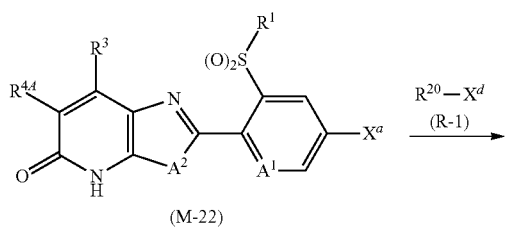

(M-22)

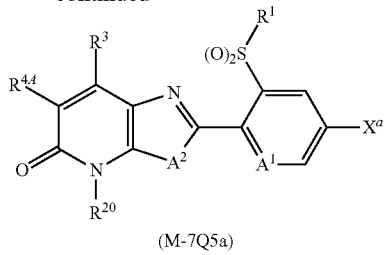

(M-7Q5a)

[wherein the symbols are the same as defined above.]

The Compound (M-7Q5a) may be prepared by reacting a compound represented by formula (M-22) (hereinafter referred to as "Compound (M-22)") with a compound represented by formula (R-1) (hereinafter referred to as "Compound (R-1)").

The Compound (M-22) may be prepared by oxidizing a compound represented by formula (M-20) (hereinafter referred to as "Compound (M-20)"), and then subjecting the resulting compound to a rearrangement reaction.

These reactions may be carried out according to the methods described in WO 2016/023954 pamphlet.

The Compound (M-20) and the Compound (R-1) are commercially available compounds or may be prepared according to known methods.

Reference Process 15

A compound represented by formula (M-7Q5b) (hereinafter referred to as "Compound (M-7Q5b)") may be prepared according to the following scheme.

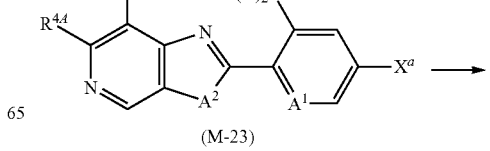

(M-23)

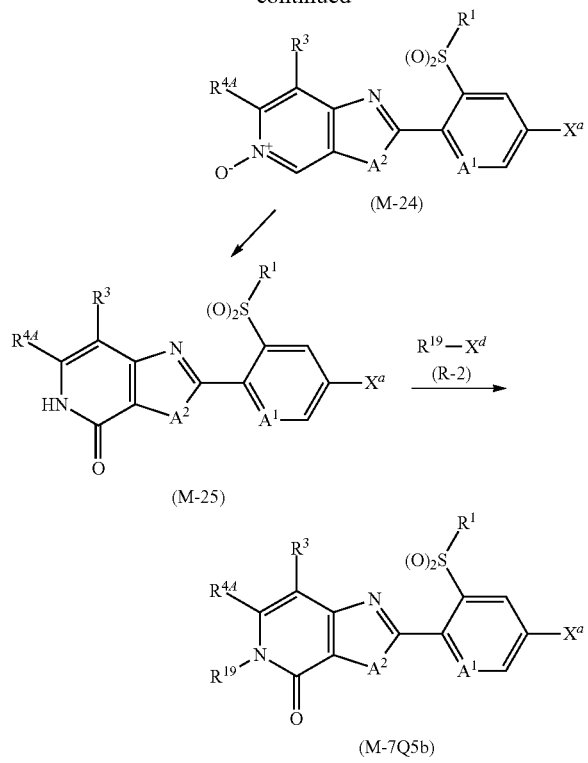

(M-24)

(M-25)

(M-7Q5b)

[wherein the symbols are the same as defined above.]

The Compound (M-7Q5b) may be prepared by reacting a compound represented by formula (M-25) (hereinafter referred to as "Compound (M-25)") with a compound represented by formula (R-2) (hereinafter referred to as "Compound (R-2)").

The Compound (M-25) may be prepared by oxidizing a compound represented by formula (M-23) (hereinafter referred to as "Compound (M-23)"), and then subjecting the resulting compound to a rearrangement reaction.

These reactions may be carried out according to the methods described in WO 2016/023954 pamphlet.

The Compound (M-23) and the Compound (R-2) are commercially available compounds or may be prepared according to known methods.

Reference Process 16

A compound represented by formula (M-7Q6) (hereinafter referred to as "Compound (M-7Q6)") may be prepared by reacting a compound represented by formula (M-26) (hereinafter referred to as "Compound (M-26)") with a compound represented by formula (M-27) (hereinafter referred to as "Compound (M-27)") in the presence of a palladium catalyst and a base.

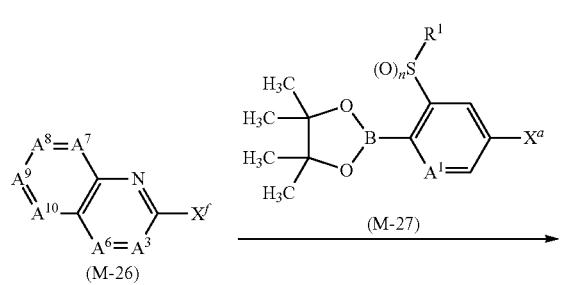

(M-26)

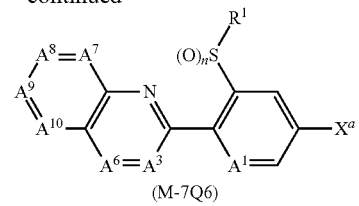

(M-7Q6)

[wherein $X^f$ represents a bromine atom or an iodine atom; and the other symbols are the same as defined above.]

The reaction may be carried out according to the method described in WO 2013/191112 pamphlet.

The Compound (M-26) is a commercially available compound or may be prepared according to a known method.

The Compound (M-27) may be prepared according to the method described in WO 2008/122603 pamphlet.

Reference Process 17

A compound represented by formula (M-7Q7d) (hereinafter referred to as "Compound (M-7Q7d)") may be prepared according to the following scheme.

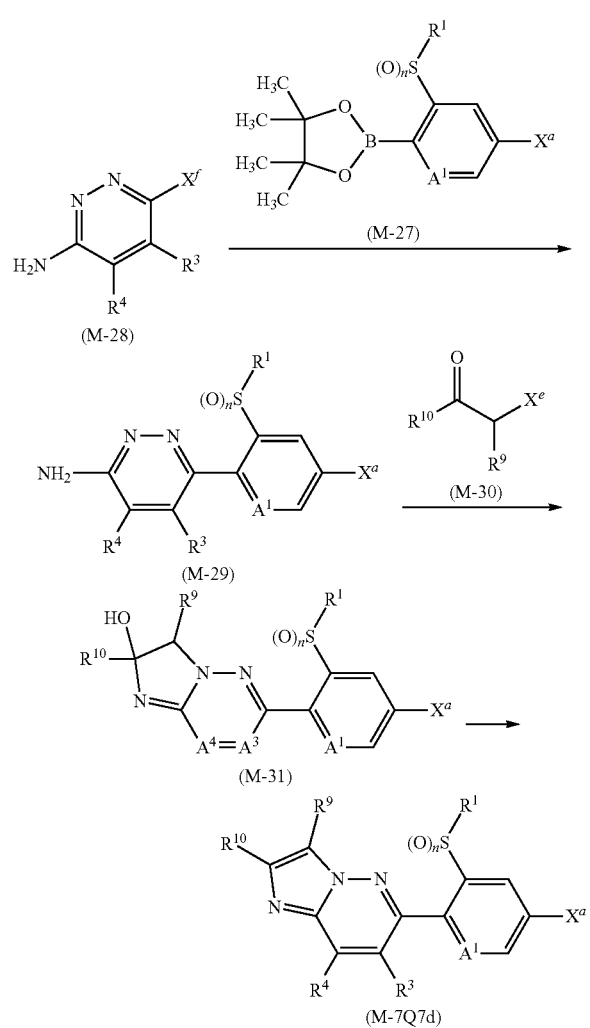

[wherein the symbols are the same as defined above.]

The Compound (M-7Q7d) may be prepared by dehydrating a compound represented by formula (M-31) (hereinafter referred to as "Compound (M-31)").

The Compound (M-31) may be prepared by reacting a compound represented by formula (M-29) (hereinafter referred to as "Compound (M-29)") with a compound represented by formula (M-30) (hereinafter referred to as "Compound (M-30)").

The Compound (M-29) may be prepared by reacting a compound represented by formula (M-28) (hereinafter referred to as "Compound (M-28)") with the Compound (M-27) in the presence of a palladium catalyst and a base.

These reactions may be carried out according to the methods described in WO 2013/191112 pamphlet.

The Compound (M-28) and the Compound (M-30) are commercially available compounds or may be prepared according to known methods.

Reference Process 18

A compound represented by formula (M-7Q7) (hereinafter referred to as "Compound (M-7Q7)") may be prepared by reacting a compound represented by formula (M-32) (hereinafter referred to as "Compound (M-32)") with the Compound (M-27) in the presence of a palladium catalyst and a base.

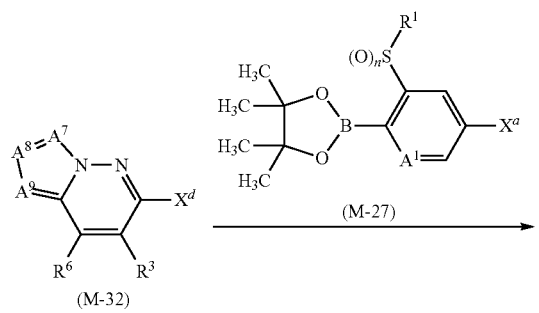

[wherein the symbols are the same as defined above.]

This reaction may be carried out according to the method described in WO 2013/191112 pamphlet.

The Compound (M-32) is a commercially available compound or may be prepared according to a known method.

Next, specific examples of the Present compound are shown below.

In the present description, Me represents a methyl group, Et represents an ethyl group, Py2 represents a 2-pyridyl group, Py3 represents a 3-pyridyl group, and Py4 represents a 4-pyridyl group. When Py2, Py3, and Py4 have substituent(s), the substituent(s) is/are indicated before the symbols with substitution position(s). For example, 4-$CF_3$-Py2 represents a 4-(trifluoromethyl)-2-pyridyl group.

A compound represented by formula (L-1)

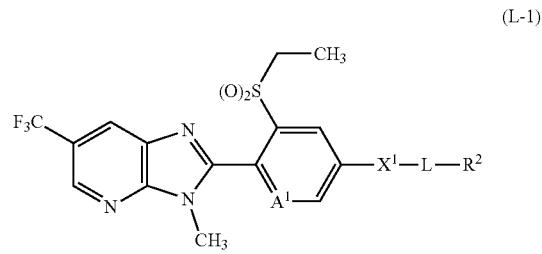

wherein $A^1$ represents a CH, $X^1$ represents an oxygen atom, L represents a $CH_2$, and $R^2$ represents any one substituent described in [Table 1] to [Table 9] (hereinafter referred to as "Compound group SX1").

TABLE 1

| Py2 |
|---|
| 3-Me—Py2 |
| 4-Me—Py2 |
| 5-Me—Py2 |
| 6-Me—Py2 |
| 3-Cl—Py2 |
| 4-Cl—Py2 |
| 5-Cl—Py2 |
| 6-Cl—Py2 |
| 3-$CF_3$—Py2 |
| 4-$CF_3$—Py2 |
| 5-$CF_3$—Py2 |
| 6-$CF_3$—Py2 |
| 3-OMe—Py2 |
| 4-OMe—Py2 |
| 5-OMe—Py2 |
| 6-OMe—Py2 |

TABLE 2

| Py3 |
|---|
| 2-Me—Py3 |
| 4-Me—Py3 |
| 5-Me—Py3 |
| 6-Me—Py3 |
| 2-Cl—Py3 |
| 4-Cl—Py3 |
| 5-Cl—Py3 |
| 6-Cl—Py3 |
| 2-$CF_3$—Py3 |
| 4-$CF_3$—Py3 |
| 5-$CF_3$—Py3 |
| 6-$CF_3$—Py3 |
| 2-OMe—Py3 |
| 4-OMe—Py3 |
| 5-OMe—Py3 |
| 6-OMe—Py3 |

TABLE 3

| Py4 |
|---|
| 2-Me—Py4 |
| 3-Me—Py4 |
| 5-Me—Py4 |
| 6-Me—Py4 |
| 2-Cl—Py4 |
| 3-Cl—Py4 |
| 5-Cl—Py4 |
| 6-Cl—Py4 |

TABLE 3-continued
Py4
2-CF$_3$—Py4
3-CF$_3$—Py4
5-CF$_3$—Py4
6-CF$_3$—Py4
2-OMe—Py4
3-OMe—Py4
5-OMe—Py4
6-OMe—Py4
TABLE 4
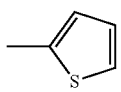
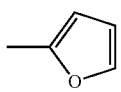
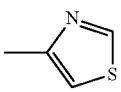
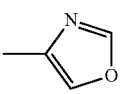
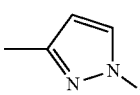
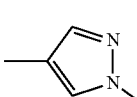
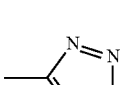
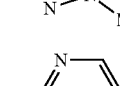
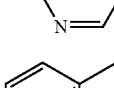
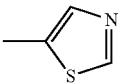
TABLE 5
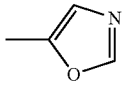
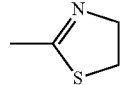
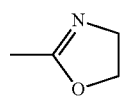
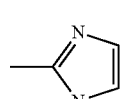
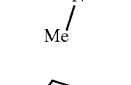
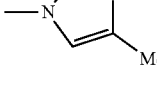
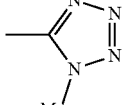
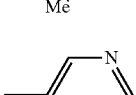
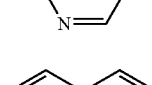
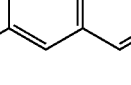
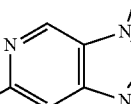
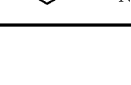
TABLE 6
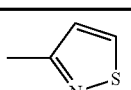
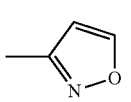
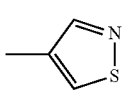
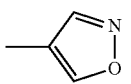

TABLE 6-continued

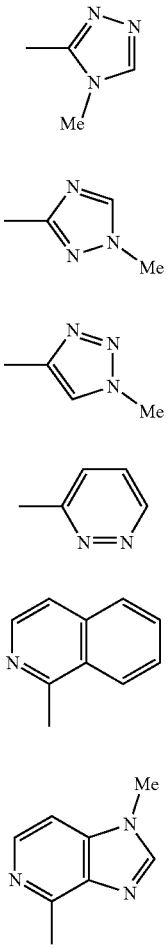

TABLE 7

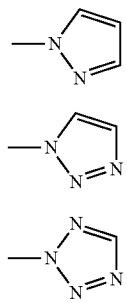

TABLE 8

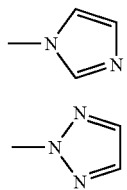

TABLE 8-continued

TABLE 9

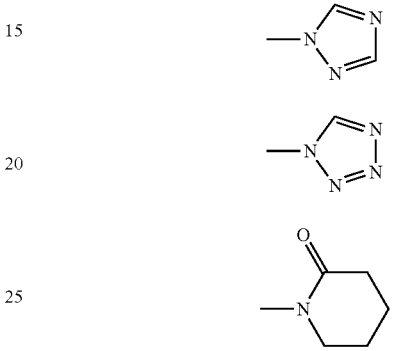

A compound represented by formula (L-1), wherein $A^1$ represents a CH, $X^1$ represents a sulfur atom, L represents a $CH_2$, and $R^2$ represents any one substituent described in [Table 1] to [Table 9] (hereinafter referred to as "Compound group SX2").

A compound represented by formula (L-1), wherein $A^1$ represents a nitrogen atom, $X^1$ represents an oxygen atom, L represents a $CH_2$, and $R^2$ represents any one substituent described in [Table 1] to [Table 9] (hereinafter referred to as "Compound group SX3").

A compound represented by formula (L-1), wherein $A^1$ represents a nitrogen atom, $X^1$ represents a sulfur atom, L represents a $CH_2$, and $R^2$ represents any one substituent described in [Table 1] to [Table 9] (hereinafter referred to as "Compound group SX4").

A compound represented by formula (L-1), wherein $A^1$ represents a CH, $X^1$ represents an oxygen atom, L represents a single bond, and $R^2$ represents any one substituent described in [Table 1] to [Table 6] (hereinafter referred to as "Compound group SX5").

A compound represented by formula (L-1), wherein $A^1$ represents a CH, $X^1$ represents a sulfur atom, L represents a single bond, and $R^2$ represents any one substituent described in [Table 1] to [Table 6] (hereinafter referred to as "Compound group SX6").

A compound represented by formula (L-1), wherein $A^1$ represents a nitrogen atom, $X^1$ represents an oxygen atom, L represents a single bond, and $R^2$ represents any one substituent described in [Table 1] to [Table 6](hereinafter referred to as "Compound group SX7").

A compound represented by formula (L-1), wherein $A^1$ represents a nitrogen atom, $X^1$ represents a sulfur atom, L represents a single bond, and $R^2$ represents any one substituent described in [Table 1] to [Table 6](hereinafter referred to as "Compound group SX8").

A compound represented by formula (L-2)

(L-2)

wherein A¹ represents a CH, X¹ represents an oxygen atom, L represents a CH$_2$, and R² represents any one substituent described in [Table 1] to [Table 9] (hereinafter referred to as "Compound group SX9").

A compound represented by formula (L-2), wherein A¹ represents a CH, X¹ represents a sulfur atom, L represents a CH$_2$, and R² represents any one substituent described in [Table 1] to [Table 9] (hereinafter referred to as "Compound group SX10").

A compound represented by formula (L-2), wherein A¹ represents a nitrogen atom, X¹ represents an oxygen atom, L represents a CH$_2$, and R² represents any one substituent described in [Table 1] to [Table 9] (hereinafter referred to as "Compound group SX11").

A compound represented by formula (L-2), wherein A¹ represents a nitrogen atom, X¹ represents a sulfur atom, L represents a CH$_2$, and R² represents any one substituent described in [Table 1] to [Table 9] (hereinafter referred to as "Compound group SX12").

A compound represented by formula (L-2), wherein A¹ represents a CH, X¹ represents an oxygen atom, L represents a single bond, and R² represents any one substituent described in [Table 1] to [Table 6] (hereinafter referred to as "Compound group SX13").

A compound represented by formula (L-2), wherein A¹ represents a CH, X¹ represents a sulfur atom, L represents a single bond, and R² represents any one substituent described in [Table 1] to [Table 6] (hereinafter referred to as "Compound group SX14").

A compound represented by formula (L-2), wherein A¹ represents a nitrogen atom, X¹ represents an oxygen atom, L represents a single bond, and R² represents any one substituent described in [Table 1] to [Table 6](hereinafter referred to as "Compound group SX15").

A compound represented by formula (L-2), wherein A¹ represents a nitrogen atom, X¹ represents a sulfur atom, L represents a single bond, and R² represents any one substituent described in [Table 1] to [Table 6](hereinafter referred to as "Compound group SX16").

A compound represented by formula (L-3)

(L-3)

wherein A¹ represents a CH, X¹ represents an oxygen atom, L represents a CH$_2$, and R² represents any one substituent described in [Table 1] to [Table 9] (hereinafter referred to as "Compound group SX17").

A compound represented by formula (L-3), wherein A represents a CH, X¹ represents a sulfur atom, L represents a CH$_2$, and R² represents any one substituent described in [Table 1] to [Table 9] (hereinafter referred to as "Compound group SX18").

A compound represented by formula (L-3), wherein A¹ represents a nitrogen atom, X¹ represents an oxygen atom, L represents a CH$_2$, and R² represents any one substituent described in [Table 1] to [Table 9] (hereinafter referred to as "Compound group SX19").

A compound represented by formula (L-3), wherein A¹ represents a nitrogen atom, X¹ represents a sulfur atom, L represents a CH$_2$, and R² represents any one substituent described in [Table 1] to [Table 9] (hereinafter referred to as "Compound group SX20").

A compound represented by formula (L-3), wherein A¹ represents a CH, X¹ represents an oxygen atom, L represents a single bond, and R² represents any one substituent described in [Table 1] to [Table 6] (hereinafter referred to as "Compound group SX21").

A compound represented by formula (L-3), wherein A¹ represents a CH, X¹ represents a sulfur atom, L represents a single bond, and R² represents any one substituent described in [Table 1] to [Table 6] (hereinafter referred to as "Compound group SX22").

A compound represented by formula (L-3), wherein A¹ represents a nitrogen atom, X¹ represents an oxygen atom, L represents a single bond, and R² represents any one substituent described in [Table 1] to [Table 6](hereinafter referred to as "Compound group SX23").

A compound represented by formula (L-3), wherein A represents a nitrogen atom, X¹ represents a sulfur atom, L represents a single bond, and R² represents any one substituent described in [Table 1] to [Table 6](hereinafter referred to as "Compound group SX24").

A compound represented by formula (L-4)

(L-4)

wherein A¹ represents a CH, X¹ represents an oxygen atom, L represents a CH$_2$, and R² represents any one substituent described in [Table 1] to [Table 9] (hereinafter referred to as "Compound group SX25").

A compound represented by formula (L-4), wherein A¹ represents a CH, X¹ represents a sulfur atom, L represents a CH$_2$, and R² represents any one substituent described in [Table 1] to [Table 9] (hereinafter referred to as "Compound group SX26").

A compound represented by formula (L-4), wherein A¹ represents a nitrogen atom, X¹ represents an oxygen atom, L represents a CH$_2$, and R² represents any one substituent described in [Table 1] to [Table 9] (hereinafter referred to as "Compound group SX27").

A compound represented by formula (L-4), wherein $A^1$ represents a nitrogen atom, $X^1$ represents a sulfur atom, L represents a $CH_2$, and $R^2$ represents any one substituent described in [Table 1] to [Table 9] (hereinafter referred to as "Compound group SX28").

A compound represented by formula (L-4), wherein $A^1$ represents a CH, $X^1$ represents an oxygen atom, L represents a single bond, and $R^2$ represents any one substituent described in [Table 1] to [Table 6] (hereinafter referred to as "Compound group SX29").

A compound represented by formula (L-4), wherein $A^1$ represents a CH, $X^1$ represents a sulfur atom, L represents a single bond, and $R^2$ represents any one substituent described in [Table 1] to [Table 6] (hereinafter referred to as "Compound group SX30").

A compound represented by formula (L-4), wherein $A^1$ represents a nitrogen atom, $X^1$ represents an oxygen atom, L represents a single bond, and $R^2$ represents any one substituent described in [Table 1] to [Table 6](hereinafter referred to as "Compound group SX31").

A compound represented by formula (L-4), wherein $A^1$ represents a nitrogen atom, $X^1$ represents a sulfur atom, L represents a single bond, and $R^2$ represents any one substituent described in [Table 1] to [Table 6](hereinafter referred to as "Compound group SX32").

A compound represented by formula (L-5)

(L-5)

wherein $A^1$ represents a CH, $X^1$ represents an oxygen atom, L represents a $CH_2$, and $R^2$ represents any one substituent described in [Table 1] to [Table 9] (hereinafter referred to as "Compound group SX33").

A compound represented by formula (L-5), wherein $A^1$ represents a CH, $X^1$ represents a sulfur atom, L represents a $CH_2$, and $R^2$ represents any one substituent described in [Table 1] to [Table 9] (hereinafter referred to as "Compound group SX34").

A compound represented by formula (L-5), wherein A represents a nitrogen atom, $X^1$ represents an oxygen atom, L represents a $CH_2$, and $R^2$ represents any one substituent described in [Table 1] to [Table 9] (hereinafter referred to as "Compound group SX35").

A compound represented by formula (L-5), wherein A represents a nitrogen atom, $X^1$ represents a sulfur atom, L represents a $CH_2$, and $R^2$ represents any one substituent described in [Table 1] to [Table 9] (hereinafter referred to as "Compound group SX36").

A compound represented by formula (L-5), wherein $A^1$ represents a CH, $X^1$ represents an oxygen atom, L represents a single bond, and $R^2$ represents any one substituent described in [Table 1] to [Table 6] (hereinafter referred to as "Compound group SX37").

A compound represented by formula (L-5), wherein $A^1$ represents a CH, $X^1$ represents a sulfur atom, L represents a single bond, and $R^2$ represents any one substituent described in [Table 1] to [Table 6] (hereinafter referred to as "Compound group SX38").

A compound represented by formula (L-5), wherein $A^1$ represents a nitrogen atom, $X^1$ represents an oxygen atom, L represents a single bond, and $R^2$ represents any one substituent described in [Table 1] to [Table 6](hereinafter referred to as "Compound group SX39").

A compound represented by formula (L-5), wherein $A^1$ represents a nitrogen atom, $X^1$ represents a sulfur atom, L represents a single bond, and $R^2$ represents any one substituent described in [Table 1] to [Table 6](hereinafter referred to as "Compound group SX40").

A compound represented by formula (L-6)

(L-6)

wherein $A^1$ represents a CH, $X^1$ represents an oxygen atom, L represents a $CH_2$, and $R^2$ represents any one substituent described in [Table 1] to [Table 9] (hereinafter referred to as "Compound group SX41").

A compound represented by formula (L-6), wherein $A^1$ represents a CH, $X^1$ represents a sulfur atom, L represents a $CH_2$, and $R^2$ represents any one substituent described in [Table 1] to [Table 9] (hereinafter referred to as "Compound group SX42").

A compound represented by formula (L-6), wherein $A^1$ represents a nitrogen atom, $X^1$ represents an oxygen atom, L represents a $CH_2$, and $R^2$ represents any one substituent described in [Table 1] to [Table 9] (hereinafter referred to as "Compound group SX43").

A compound represented by formula (L-6), wherein $A^1$ represents a nitrogen atom, $X^1$ represents a sulfur atom, L represents a $CH_2$, and $R^2$ represents any one substituent described in [Table 1] to [Table 9] (hereinafter referred to as "Compound group SX44").

A compound represented by formula (L-6), wherein $A^1$ represents a CH, $X^1$ represents an oxygen atom, L represents a single bond, and $R^2$ represents any one substituent described in [Table 1] to [Table 6] (hereinafter referred to as "Compound group SX45").

A compound represented by formula (L-6), wherein $A^1$ represents a CH, $X^1$ represents a sulfur atom, L represents a single bond, and $R^2$ represents any one substituent described in [Table 1] to [Table 6] (hereinafter referred to as "Compound group SX46").

A compound represented by formula (L-6), wherein $A^1$ represents a nitrogen atom, $X^1$ represents an oxygen atom, L represents a single bond, and $R^2$ represents any one substituent described in [Table 1] to [Table 6](hereinafter referred to as "Compound group SX47").

A compound represented by formula (L-6), wherein $A^1$ represents a nitrogen atom, $X^1$ represents a sulfur atom, L represents a single bond, and $R^2$ represents any one substituent described in [Table 1] to [Table 6](hereinafter referred to as "Compound group SX48").

A compound represented by formula (L-7)

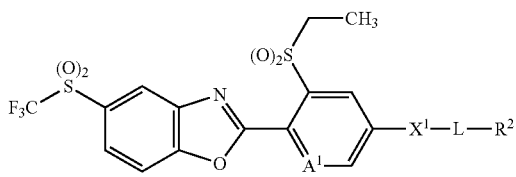

wherein A¹ represents a CH, $X^1$ represents an oxygen atom, L represents a $CH_2$, and $R^2$ represents any one substituent described in [Table 1] to [Table 9] (hereinafter referred to as "Compound group SX49").

A compound represented by formula (L-7), wherein A¹ represents a CH, $X^1$ represents a sulfur atom, L represents a $CH_2$, and $R^2$ represents any one substituent described in [Table 1] to [Table 9] (hereinafter referred to as "Compound group SX50").

A compound represented by formula (L-7), wherein A¹ represents a nitrogen atom, $X^1$ represents an oxygen atom, L represents a $CH_2$, and $R^2$ represents any one substituent described in [Table 1] to [Table 9] (hereinafter referred to as "Compound group SX51").

A compound represented by formula (L-7), wherein A¹ represents a nitrogen atom, $X^1$ represents a sulfur atom, L represents a $CH_2$, and $R^2$ represents any one substituent described in [Table 1] to [Table 9] (hereinafter referred to as "Compound group SX52").

A compound represented by formula (L-7), wherein A represents a CH, $X^1$ represents an oxygen atom, L represents a single bond, and $R^2$ represents any one substituent described in [Table 1] to [Table 6] (hereinafter referred to as "Compound group SX53").

A compound represented by formula (L-7), wherein A¹ represents a CH, $X^1$ represents a sulfur atom, L represents a single bond, and $R^2$ represents any one substituent described in [Table 1] to [Table 6] (hereinafter referred to as "Compound group SX54").

A compound represented by formula (L-7), wherein A¹ represents a nitrogen atom, $X^1$ represents an oxygen atom, L represents a single bond, and $R^2$ represents any one substituent described in [Table 1] to [Table 6](hereinafter referred to as "Compound group SX55").

A compound represented by formula (L-7), wherein A¹ represents a nitrogen atom, $X^1$ represents a sulfur atom, L represents a single bond, and $R^2$ represents any one substituent described in [Table 1] to [Table 6](hereinafter referred to as "Compound group SX56").

A compound represented by formula (L-8)

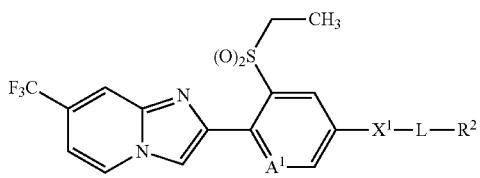

wherein A¹ represents a CH, $X^1$ represents an oxygen atom, L represents a $CH_2$, and $R^2$ represents any one substituent described in [Table 1] to [Table 9] (hereinafter referred to as "Compound group SX57").

A compound represented by formula (L-8), wherein A¹ represents a CH, $X^1$ represents a sulfur atom, L represents a $CH_2$, and $R^2$ represents any one substituent described in [Table 1] to [Table 9] (hereinafter referred to as "Compound group SX58").

A compound represented by formula (L-8), wherein A represents a nitrogen atom, $X^1$ represents an oxygen atom, L represents a $CH_2$, and $R^2$ represents any one substituent described in [Table 1] to [Table 9] (hereinafter referred to as "Compound group SX59").

A compound represented by formula (L-8), wherein A¹ represents a nitrogen atom, $X^1$ represents a sulfur atom, L represents a $CH_2$, and $R^2$ represents any one substituent described in [Table 1] to [Table 9] (hereinafter referred to as "Compound group SX60").

A compound represented by formula (L-8), wherein A¹ represents a CH, $X^1$ represents an oxygen atom, L represents a single bond, and $R^2$ represents any one substituent described in [Table 1] to [Table 6] (hereinafter referred to as "Compound group SX61").

A compound represented by formula (L-8), wherein A¹ represents a CH, $X^1$ represents a sulfur atom, L represents a single bond, and $R^2$ represents any one substituent described in [Table 1] to [Table 6] (hereinafter referred to as "Compound group SX62").

A compound represented by formula (L-8), wherein A represents a nitrogen atom, $X^1$ represents an oxygen atom, L represents a single bond, and $R^2$ represents any one substituent described in [Table 1] to [Table 6](hereinafter referred to as "Compound group SX63").

A compound represented by formula (L-8), wherein A¹ represents a nitrogen atom, $X^1$ represents a sulfur atom, L represents a single bond, and $R^2$ represents any one substituent described in [Table 1] to [Table 6](hereinafter referred to as "Compound group SX64").

A compound represented by formula (L-9)

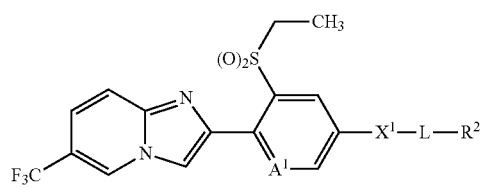

wherein A¹ represents a CH, $X^1$ represents an oxygen atom, L represents a $CH_2$, and $R^2$ represents any one substituent described in [Table 1] to [Table 9] (hereinafter referred to as "Compound group SX65").

A compound represented by formula (L-9), wherein A¹ represents a CH, $X^1$ represents a sulfur atom, L represents a $CH_2$, and $R^2$ represents any one substituent described in [Table 1] to [Table 9] (hereinafter referred to as "Compound group SX66").

A compound represented by formula (L-9), wherein A¹ represents a nitrogen atom, $X^1$ represents an oxygen atom, L represents a $CH_2$, and $R^2$ represents any one substituent described in [Table 1] to [Table 9] (hereinafter referred to as "Compound group SX67").

A compound represented by formula (L-9), wherein A¹ represents a nitrogen atom, $X^1$ represents a sulfur atom, L represents a $CH_2$, and $R^2$ represents any one substituent described in [Table 1] to [Table 9] (hereinafter referred to as "Compound group SX68").

A compound represented by formula (L-9), wherein A¹ represents a CH, X¹ represents an oxygen atom, L represents a single bond, and R² represents any one substituent described in [Table 1] to [Table 6] (hereinafter referred to as "Compound group SX69").

A compound represented by formula (L-9), wherein A¹ represents a CH, X¹ represents a sulfur atom, L represents a single bond, and R² represents any one substituent described in [Table 1] to [Table 6] (hereinafter referred to as "Compound group SX70").

A compound represented by formula (L-9), wherein A¹ represents a nitrogen atom, X¹ represents an oxygen atom, L represents a single bond, and R² represents any one substituent described in [Table 1] to [Table 6](hereinafter referred to as "Compound group SX71").

A compound represented by formula (L-9), wherein A¹ represents a nitrogen atom, X¹ represents a sulfur atom, L represents a single bond, and R² represents any one substituent described in [Table 1] to [Table 6](hereinafter referred to as "Compound group SX72").

A compound represented by formula (L-10)

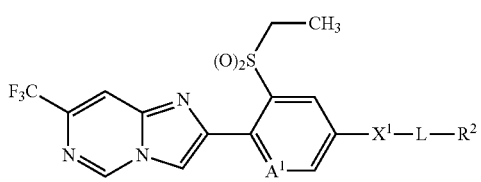

(L-10)

wherein A¹ represents a CH, X¹ represents an oxygen atom, L represents a CH₂, and R² represents any one substituent described in [Table 1] to [Table 9] (hereinafter referred to as "Compound group SX73").

A compound represented by formula (L-10), wherein A¹ represents a CH, X¹ represents a sulfur atom, L represents a CH₂, and R² represents any one substituent described in [Table 1] to [Table 9] (hereinafter referred to as "Compound group SX74").

A compound represented by formula (L-10), wherein A¹ represents a nitrogen atom, X¹ represents an oxygen atom, L represents a CH₂, and R² represents any one substituent described in [Table 1] to [Table 9] (hereinafter referred to as "Compound group SX75").

A compound represented by formula (L-10), wherein A¹ represents a nitrogen atom, X¹ represents a sulfur atom, L represents a CH₂, and R² represents any one substituent described in [Table 1] to [Table 9] (hereinafter referred to as "Compound group SX76").

A compound represented by formula (L-10), wherein A¹ represents a CH, X¹ represents an oxygen atom, L represents a single bond, and R² represents any one substituent described in [Table 1] to [Table 6] (hereinafter referred to as "Compound group SX77").

A compound represented by formula (L-10), wherein A¹ represents a CH, X¹ represents a sulfur atom, L represents a single bond, and R² represents any one substituent described in [Table 1] to [Table 6] (hereinafter referred to as "Compound group SX78").

A compound represented by formula (L-10), wherein A¹ represents a nitrogen atom, X¹ represents an oxygen atom, L represents a single bond, and R² represents any one substituent described in [Table 1] to [Table 6](hereinafter referred to as "Compound group SX79").

A compound represented by formula (L-10), wherein A¹ represents a nitrogen atom, X¹ represents a sulfur atom, L represents a single bond, and R² represents any one substituent described in [Table 1] to [Table 6](hereinafter referred to as "Compound group SX80").

A compound represented by formula (L-11)

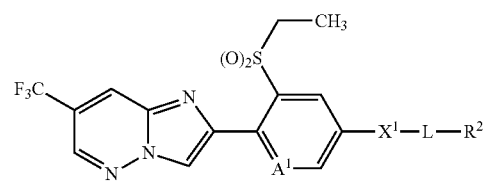

(L-11)

wherein A¹ represents a CH, X¹ represents an oxygen atom, L represents a CH₂, and R² represents any one substituent described in [Table 1] to [Table 9] (hereinafter referred to as "Compound group SX81").

A compound represented by formula (L-11), wherein A¹ represents a CH, X¹ represents a sulfur atom, L represents a CH₂, and R² represents any one substituent described in [Table 1] to [Table 9] (hereinafter referred to as "Compound group SX82").

A compound represented by formula (L-11), wherein A¹ represents a nitrogen atom, X¹ represents an oxygen atom, L represents a CH₂, and R² represents any one substituent described in [Table 1] to [Table 9] (hereinafter referred to as "Compound group SX83").

A compound represented by formula (L-11), wherein A¹ represents a nitrogen atom, X¹ represents a sulfur atom, L represents a CH₂, and R² represents any one substituent described in [Table 1] to [Table 9] (hereinafter referred to as "Compound group SX84").

A compound represented by formula (L-11), wherein A¹ represents a CH, X¹ represents an oxygen atom, L represents a single bond, and R² represents any one substituent described in [Table 1] to [Table 6] (hereinafter referred to as "Compound group SX85").

A compound represented by formula (L-11), wherein A¹ represents a CH, X¹ represents a sulfur atom, L represents a single bond, and R² represents any one substituent described in [Table 1] to [Table 6] (hereinafter referred to as "Compound group SX86").

A compound represented by formula (L-11), wherein A¹ represents a nitrogen atom, X¹ represents an oxygen atom, L represents a single bond, and R² represents any one substituent described in [Table 1] to [Table 6](hereinafter referred to as "Compound group SX87").

A compound represented by formula (L-11), wherein A¹ represents a nitrogen atom, X¹ represents a sulfur atom, L represents a single bond, and R² represents any one substituent described in [Table 1] to [Table 6](hereinafter referred to as "Compound group SX88").

A compound represented by formula (L-12)

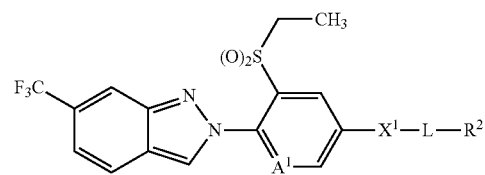

(L-12)

wherein A¹ represents a CH, X¹ represents an oxygen atom, L represents a CH₂, and R² represents any one substituent described in [Table 1] to [Table 9] (hereinafter referred to as "Compound group SX89").

A compound represented by formula (L-12), wherein A represents a CH, X¹ represents a sulfur atom, L represents a CH₂, and R² represents any one substituent described in [Table 1] to [Table 9] (hereinafter referred to as "Compound group SX90").

A compound represented by formula (L-12), wherein A¹ represents a nitrogen atom, X¹ represents an oxygen atom, L represents a CH₂, and R² represents any one substituent described in [Table 1] to [Table 9] (hereinafter referred to as "Compound group SX91").

A compound represented by formula (L-12), wherein A¹ represents a nitrogen atom, X¹ represents a sulfur atom, L represents a CH₂, and R² represents any one substituent described in [Table 1] to [Table 9] (hereinafter referred to as "Compound group SX92").

A compound represented by formula (L-12), wherein A¹ represents a CH, X¹ represents an oxygen atom, L represents a single bond, and R² represents any one substituent described in [Table 1] to [Table 6] (hereinafter referred to as "Compound group SX93").

A compound represented by formula (L-12), wherein A¹ represents a CH, X¹ represents a sulfur atom, L represents a single bond, and R² represents any one substituent described in [Table 1] to [Table 6] (hereinafter referred to as "Compound group SX94").

A compound represented by formula (L-12), wherein A¹ represents a nitrogen atom, X¹ represents an oxygen atom, L represents a single bond, and R² represents any one substituent described in [Table 1] to [Table 6](hereinafter referred to as "Compound group SX95").

A compound represented by formula (L-12), wherein A represents a nitrogen atom, X¹ represents a sulfur atom, L represents a single bond, and R² represents any one substituent described in [Table 1] to [Table 6](hereinafter referred to as "Compound group SX96").

A compound represented by formula (L-13)

(L-13)

wherein A¹ represents a CH, X¹ represents an oxygen atom, L represents a CH₂, and R² represents any one substituent described in [Table 1] to [Table 9] (hereinafter referred to as "Compound group SX97").

A compound represented by formula (L-13), wherein A¹ represents a CH, X¹ represents a sulfur atom, L represents a CH₂, and R² represents any one substituent described in [Table 1] to [Table 9] (hereinafter referred to as "Compound group SX98").

A compound represented by formula (L-13), wherein A¹ represents a nitrogen atom, X¹ represents an oxygen atom, L represents a CH₂, and R² represents any one substituent described in [Table 1] to [Table 9] (hereinafter referred to as "Compound group SX99").

A compound represented by formula (L-13), wherein A¹ represents a nitrogen atom, X¹ represents a sulfur atom, L represents a CH₂, and R² represents any one substituent described in [Table 1] to [Table 9] (hereinafter referred to as "Compound group SX100").

A compound represented by formula (L-13), wherein A¹ represents a CH, X¹ represents an oxygen atom, L represents a single bond, and R² represents any one substituent described in [Table 1] to [Table 6] (hereinafter referred to as "Compound group SX101").

A compound represented by formula (L-13), wherein A¹ represents a CH, X¹ represents a sulfur atom, L represents a single bond, and R² represents any one substituent described in [Table 1] to [Table 6] (hereinafter referred to as "Compound group SX102").

A compound represented by formula (L-13), wherein A¹ represents a nitrogen atom, X¹ represents an oxygen atom, L represents a single bond, and R² represents any one substituent described in [Table 1] to [Table 6](hereinafter referred to as "Compound group SX103").

A compound represented by formula (L-13), wherein A¹ represents a nitrogen atom, X¹ represents a sulfur atom, L represents a single bond, and R² represents any one substituent described in [Table 1] to [Table 6](hereinafter referred to as "Compound group SX104").

A compound represented by formula (L-14)

(L-14)

wherein A¹ represents a CH, X¹ represents an oxygen atom, L represents a CH₂, and R² represents any one substituent described in [Table 1] to [Table 9] (hereinafter referred to as "Compound group SX105").

A compound represented by formula (L-14), wherein A¹ represents a CH, X¹ represents a sulfur atom, L represents a CH₂, and R² represents any one substituent described in [Table 1] to [Table 9] (hereinafter referred to as "Compound group SX106").

A compound represented by formula (L-14), wherein A¹ represents a nitrogen atom, X¹ represents an oxygen atom, L represents a CH₂, and R² represents any one substituent described in [Table 1] to [Table 9] (hereinafter referred to as "Compound group SX107").

A compound represented by formula (L-14), wherein A¹ represents a nitrogen atom, X¹ represents a sulfur atom, L represents a CH₂, and R² represents any one substituent described in [Table 1] to [Table 9] (hereinafter referred to as "Compound group SX108").

A compound represented by formula (L-14), wherein A¹ represents a CH, X¹ represents an oxygen atom, L represents a single bond, and R² represents any one substituent described in [Table 1] to [Table 6] (hereinafter referred to as "Compound group SX109").

A compound represented by formula (L-14), wherein A¹ represents a CH, X¹ represents a sulfur atom, L represents a single bond, and R² represents any one substituent described in [Table 1] to [Table 6] (hereinafter referred to as "Compound group SX110").

A compound represented by formula (L-14), wherein A¹ represents a nitrogen atom, X¹ represents an oxygen atom, L represents a single bond, and R² represents any one substituent described in [Table 1] to [Table 6](hereinafter referred to as "Compound group SX111").

A compound represented by formula (L-14), wherein A¹ represents a nitrogen atom, X¹ represents a sulfur atom, L represents a single bond, and R² represents any one substituent described in [Table 1] to [Table 6](hereinafter referred to as "Compound group SX112").

A compound represented by formula (L-15)

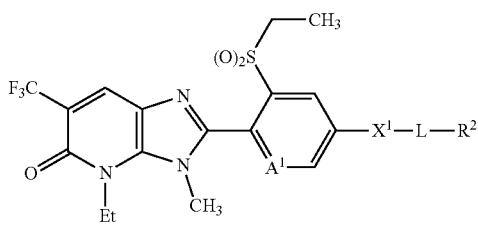

(L-15)

wherein A¹ represents a CH, X¹ represents an oxygen atom, L represents a CH₂, and R² represents any one substituent described in [Table 1] to [Table 9] (hereinafter referred to as "Compound group SX113").

A compound represented by formula (L-15), wherein A represents a CH, X¹ represents a sulfur atom, L represents a CH₂, and R² represents any one substituent described in [Table 1] to [Table 9] (hereinafter referred to as "Compound group SX114").

A compound represented by formula (L-15), wherein A¹ represents a nitrogen atom, X¹ represents an oxygen atom, L represents a CH₂, and R² represents any one substituent described in [Table 1] to [Table 9] (hereinafter referred to as "Compound group SX115").

A compound represented by formula (L-15), wherein A¹ represents a nitrogen atom, X¹ represents a sulfur atom, L represents a CH₂, and R² represents any one substituent described in [Table 1] to [Table 9] (hereinafter referred to as "Compound group SX116").

A compound represented by formula (L-15), wherein A¹ represents a CH, X¹ represents an oxygen atom, L represents a single bond, and R² represents any one substituent described in [Table 1] to [Table 6] (hereinafter referred to as "Compound group SX117").

A compound represented by formula (L-15), wherein A¹ represents a CH, X¹ represents a sulfur atom, L represents a single bond, and R² represents any one substituent described in [Table 1] to [Table 6] (hereinafter referred to as "Compound group SX118").

A compound represented by formula (L-15), wherein A¹ represents a nitrogen atom, X¹ represents an oxygen atom, L represents a single bond, and R² represents any one substituent described in [Table 1] to [Table 6](hereinafter referred to as "Compound group SX119").

A compound represented by formula (L-15), wherein A¹ represents a nitrogen atom, X¹ represents a sulfur atom, L represents a single bond, and R² represents any one substituent described in [Table 1] to [Table 6](hereinafter referred to as "Compound group SX120").

A compound represented by formula (L-16)

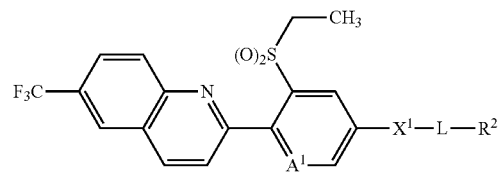

(L-16)

wherein A¹ represents a CH, X¹ represents an oxygen atom, L represents a CH₂, and R² represents any one substituent described in [Table 1] to [Table 9] (hereinafter referred to as "Compound group SX121").

A compound represented by formula (L-16), wherein A¹ represents a CH, X¹ represents a sulfur atom, L represents a CH₂, and R² represents any one substituent described in [Table 1] to [Table 9] (hereinafter referred to as "Compound group SX122").

A compound represented by formula (L-16), wherein A¹ represents a nitrogen atom, X¹ represents an oxygen atom, L represents a CH₂, and R² represents any one substituent described in [Table 1] to [Table 9] (hereinafter referred to as "Compound group SX123").

A compound represented by formula (L-16), wherein A¹ represents a nitrogen atom, X¹ represents a sulfur atom, L represents a CH₂, and R² represents any one substituent described in [Table 1] to [Table 9] (hereinafter referred to as "Compound group SX124").

A compound represented by formula (L-16), wherein A¹ represents a CH, X¹ represents an oxygen atom, L represents a single bond, and R² represents any one substituent described in [Table 1] to [Table 6] (hereinafter referred to as "Compound group SX125").

A compound represented by formula (L-16), wherein A¹ represents a CH, X¹ represents a sulfur atom, L represents a single bond, and R² represents any one substituent described in [Table 1] to [Table 6] (hereinafter referred to as "Compound group SX126").

A compound represented by formula (L-16), wherein A¹ represents a nitrogen atom, X¹ represents an oxygen atom, L represents a single bond, and R² represents any one substituent described in [Table 1] to [Table 6](hereinafter referred to as "Compound group SX127").

A compound represented by formula (L-16), wherein A¹ represents a nitrogen atom, X^L represents a sulfur atom, L represents a single bond, and R² represents any one substituent described in [Table 1] to [Table 6](hereinafter referred to as "Compound group SX128").

A compound represented by formula (L-17)

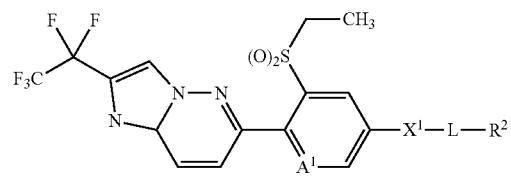

(L-17)

wherein A¹ represents a CH, X¹ represents an oxygen atom, L represents a CH₂, and R² represents any one substituent described in [Table 1] to [Table 9] (hereinafter referred to as "Compound group SX129").

A compound represented by formula (L-17), wherein $A^1$ represents a CH, $X^1$ represents a sulfur atom, L represents a $CH_2$, and $R^2$ represents any one substituent described in [Table 1] to [Table 9] (hereinafter referred to as "Compound group SX130").

A compound represented by formula (L-17), wherein $A^1$ represents a nitrogen atom, $X^1$ represents an oxygen atom, L represents a $CH_2$, and $R^2$ represents any one substituent described in [Table 1] to [Table 9] (hereinafter referred to as "Compound group SX131").

A compound represented by formula (L-17), wherein $A^1$ represents a nitrogen atom, $X^1$ represents a sulfur atom, L represents a $CH_2$, and $R^2$ represents any one substituent described in [Table 1] to [Table 9] (hereinafter referred to as "Compound group SX132").

A compound represented by formula (L-17), wherein $A^1$ represents a CH, $X^1$ represents an oxygen atom, L represents a single bond, and $R^2$ represents any one substituent described in [Table 1] to [Table 6] (hereinafter referred to as "Compound group SX133").

A compound represented by formula (L-17), wherein $A^1$ represents a CH, $X^1$ represents a sulfur atom, L represents a single bond, and $R^2$ represents any one substituent described in [Table 1] to [Table 6] (hereinafter referred to as "Compound group SX134").

A compound represented by formula (L-17), wherein $A^1$ represents a nitrogen atom, $X^1$ represents an oxygen atom, L represents a single bond, and $R^2$ represents any one substituent described in [Table 1] to [Table 6](hereinafter referred to as "Compound group SX135").

A compound represented by formula (L-17), wherein $A^1$ represents a nitrogen atom, $X^1$ represents a sulfur atom, L represents a single bond, and $R^2$ represents any one substituent described in [Table 1] to [Table 6](hereinafter referred to as "Compound group SX136").

All the compounds of the Compound groups SX1 to SX136 may be prepared according to the methods described in Examples or Processes of the present description.

The Present compound may be mixed with or used in combination with the following one or more ingredient(s) selected from the group consisting of Group (a), Group (b), Group (c), Group (d), and Group (e) (hereinafter referred to as "Present ingredient").

When the Present compound is mixed with or used in combination with the Present ingredient, they are used simultaneously, separately, or at time intervals with each other.

When the Present compound is used simultaneously with the Present ingredient, the Present compound and the Present ingredient may be contained in separate formulations or contained in one formulation.

One aspect of the present invention provides a composition comprising one or more ingredient(s) selected from the group consisting of Group (a), Group (b), Group (c), Group (d), and Group (e) (i.e., Present ingredient), and the Present compound.

Group (a) is a group of insecticidal active ingredients, miticidal active ingredients, and nematicidal active ingredients consisting of the following Subgroup a-1 to Subgroup a-10.

Subgroup a-1: Carbamate acetylcholinesterase (AChE) inhibitors
Subgroup a-2: Organophosphorus acetylcholinesterase (AChE) inhibitors
Subgroup a-3: GABAergic chloride channel blockers
Subgroup a-4: GABAergic chloride channel allosteric modulators
Subgroup a-5: Sodium channel modulators
Subgroup a-6: Nicotinic acetylcholine receptor (nAChR) competitive modulators
Subgroup a-7: Ryanodine receptor modulators
Subgroup a-8: Microbial materials
Subgroup a-9: Nematicidal active ingredients
Subgroup a-10: Other insecticidal active ingredients and miticidal active ingredients Group (b) is a group of fungicidal active ingredients consisting of the following Subgroup b-1 to Subgroup b-18.
Subgroup b-1: PA fungicides (Phenylamides)
Subgroup b-2: MBC fungicides (Methyl benzimidazole carbamates)
Subgroup b-3: Thiazole carboxamides
Subgroup b-4: SDHI (Succinate dehydrogenase inhibitors)
Subgroup b-5: QoI fungicides (Qo inhibitors)
Subgroup b-6: QiI fungicides (Qi inhibitors)
Subgroup b-7: Thiophenecarboxamides
Subgroup b-8: AP fungicides (Anilinopyrimidines)
Subgroup b-9: PP fungicides (Phenylpyrroles)
Subgroup b-10: AH fungicides (Aromatic hydrocarbons)
Subgroup b-11: DMI-fungicides (Demethylation inhibitors)
Subgroup b-12: CCA fungicides (Carboxylic acid amides)
Subgroup b-13: Piperidinyl thiazole isoxazolines
Subgroup b-14: Tetrazolyl oximes
Subgroup b-15: Dithiocarbamates
Subgroup b-16: Phthalimides
Subgroup b-17: Microbial fungicides
Subgroup b-18: Other fungicides Group (c) is a group of plant growth regulatory ingredients consisting of the following Subgroup c-1, Subgroup c-2, and Subgroup c-3.
Subgroup c-1: Plant growth regulatory ingredients
Subgroup c-2: Mycorrhizal fungi
Subgroup c-3: Root nodule bacteria Group (d) is a group of phytotoxicity-reducing ingredients which reduce the phytotoxicity to crops when used in combination with another agent.

Group (e) is a group of synergists which potentiate the efficacy of another agent when used in combination with said agent.

A composition comprising said Present ingredient and the Present compound produces its effects depending on the contained amount or the content percentage of said Present ingredient or said Present compound in said composition. Thus, the use of said composition may be determined depending on the effect produced by said composition. Said composition may have one or more uses.

One aspect of said composition is an agrochemical composition.

Another aspect of said composition is a composition for controlling a harmful arthropod.

Still another aspect of said composition is an insecticidal, miticidal, or nematicidal composition.

Still another aspect of said composition is a fungicidal composition.

Still another aspect of said composition is a plant growth regulatory composition.

Still another aspect of said composition is a phytotoxicity-reducing composition.

Hereinafter, examples of the combination of the Present ingredient and the Present compound are described. For example, "alanycarb+SX" indicates a combination of alanycarb and SX.

The abbreviation of "SX" indicates any one of the Present compound selected from the Compound groups SX1 to SX136. Also, all of the following Present ingredients are known ingredients, and may be obtained from commercially available formulations, or may be prepared by known methods. When the Present ingredient is a microorganism, it may be available from a bacterial authority depository. Further, the number in parentheses represents the CAS registration number.

Combinations of the Present ingredient in the above Subgroup a-1 and the Present compound:

alanycarb+SX, aldicarb+SX, bendiocarb+SX, benfuracarb+SX, butocarboxim+SX, butoxycarboxim+SX, carbaryl (NAC)+SX, carbofuran+SX, carbosulfan+SX, ethiofencarb+SX, fenobucarb (BPMC)+SX, formetanate+SX, furathiocarb+SX, isoprocarb (MIPC)+SX, methiocarb+SX, methomyl+SX, metolcarb+SX, oxamyl+SX, pirimicarb+SX, propoxur (PHC)+SX, thiodicarb+SX, thiofanox+SX, triazamate+SX, trimethacarb+SX, XMC+SX, xylylcarb+SX.

Combinations of the Present ingredient in the above Subgroup a-2 and the Present compound:

acephate+SX, azamethiphos+SX, azinphos-ethyl+SX, azinphos-methyl+SX, cadusafos+SX, chlorethoxyfos+SX, chlorfenvinphos+SX, chlormephos+SX, chlorpyrifos+SX, chlorpyrifos-methyl+SX, coumaphos+SX, cyanophos (CYAP)+SX, demeton-S-methyl+SX, diazinon+SX, dichlorvos (DDVP)+SX, dicrotophos+SX, dimethoate+SX, dimethylvinphos+SX, disulfoton+SX, EPN+SX, ethion+SX, ethoprophos+SX, famphur+SX, fenamiphos+SX, fenitrothion (MEP)+SX, fenthion (MPP)+SX, fosthiazate+SX, heptenophos+SX, imicyafos+SX, isofenphos+SX, isopropyl-O-(methoxyaminothiophosphoryl)salicylate+SX, isoxathion+SX, malathion+SX, mecarbam+SX, methamidophos+SX, methidathion (DMTP)+SX, mevinphos+SX, monocrotophos+SX, naled (BRP)+SX, omethoate+SX, oxydemeton-methyl+SX, parathion+SX, parathion-methyl+SX, phenthoate (PAP)+SX, phorate+SX, phosalone+SX, phosmet (PMP)+SX, phosphamidon+SX, phoxim+SX, pirimiphos-methyl+SX, profenofos+SX, propetamphos+SX, prothiofos+SX, pyraclofos+SX, pyridaphenthion+SX, quinalphos+SX, sulfotep+SX, tebupirimfos+SX, temephos+SX, terbufos+SX, tetrachlorvinphos+SX, thiometon+SX, triazophos+SX, trichlorfon (DEP)+SX, vamidothion+SX.

Combinations of the Present ingredient in the above Subgroup a-3 and the Present compound:

ethiprole+SX, fipronil+SX, flufiprole+SX, chlordane+SX, endosulfan+SX, alpha-endosulfan+SX.

Combinations of the Present ingredient in the above Subgroup a-4 and the Present compound:

afoxolaner+SX, fluralaner+SX, broflanilide+SX, fluxametamide+SX.

Combinations of the Present ingredient in the above Subgroup a-5 and the Present compound:

acrinathrin+SX, allethrin+SX, bifenthrin+SX, kappa-bifenthrin+SX, bioallethrin+SX, bioresmethrin+SX, cycloprothrin+SX, cyfluthrin+SX, beta-cyfluthrin+SX, cyhalothrin+SX, gamma-cyhalothrin+SX, lambda-cyhalothrin+SX, cypermethrin+SX, alpha-cypermethrin+SX, beta-cypermethrin+SX, theta-cypermethrin+SX, zeta-cypermethrin+SX, cyphenothrin+SX, deltamethrin+SX, empenthrin+SX, esfenvalerate+SX, etofenprox+SX, fenpropathrin+SX, fenvalerate+SX, flucythrinate+SX, flumethrin+SX, fluvalinate+SX, tau-fluvalinate+SX, halfenprox+SX, heptafluthrin+SX, imiprothrin+SX, kadethrin+SX, meperfluthrin+SX, momfluorothrin+SX, permethrin+SX, phenothrin+SX, prallethrin+SX, pyrethrins+SX, resmethrin+SX, silafluofen+SX, tefluthrin+SX, kappa-tefluthrin+SX, tetramethrin+SX, tetramethylfluthrin+SX, tralomethrin+SX, transfluthrin+SX, benfluthrin+SX, flufenoprox+SX, flumethrin+SX, sigma-cypermethrin+SX, furamethrin+SX, metofluthrin+SX, profluthrin+SX, dimefluthrin+SX, epsilon-metofluthrin+SX, epsilon-momfluorothrin+SX, methoxychlor+SX.

Combinations of the Present ingredient in the above Subgroup a-6 and the Present compound:

acetamiprid+SX, clothianidin+SX, dinotefuran+SX, imidacloprid+SX, nitenpyram+SX, thiacloprid+SX, thiamethoxam+SX, sulfoxaflor+SX, flupyradifurone+SX, triflumezopyrim+SX, dicloromezotiaz+SX, cycloxaprid+SX, (E)-N-{1-[(6-chloropyridin-3-yl)methyl]pyridin-2(1H)-ylidene}-2,2,2-trifluoroacetamide (1689566-03-7)+SX.

Combinations of the Present ingredient in the above Subgroup a-7 and the Present compound:

chlorantraniliprole+SX, cyantraniliprole+SX, cycloniliprole+SX, flubendiamide+SX, tetraniliprole+SX, cyhalodiamide+SX, 3-bromo-N-[2,4-dichloro-6-(methylcarbamoyl)phenyl]-1-(3,5-dichloropyridin-2-yl)-1H-pyrazole-5-carboxamide (1104384-14-6)+SX.

Combinations of the Present ingredient in the above Subgroup a-8 and the Present compound: *Bacillus thuringiensis* BD #32+SX, *Bacillus thuringiensis* AQ52+SX, *Bacillus thuringiensis* CR-371+SX, *Bacillus thuringiensis* subsp. *Aizawai* GC-91+SX, *Bacillus thuringiensis* subsp. *Aizawai* ABTS-1857+SX, *Bacillus thuringiensis* subsp. *Aizawai* Serotype H-7+SX, *Bacillus thuringiensis* subsp. *Aizawai* AM65-52+SX, *Bacillus thuringiensis* subsp. *Kurstaki* ABTS351+SX, *Bacillus thuringiensis* subsp. *Kurstaki* PB54+SX, *Bacillus thuringiensis* subsp. *Kurstaki* EG234+SX, *Bacillus thuringiensis* subsp. *Kurstaki* HD-1+SX, *Bacillus thuringiensis* subsp. *Kurstaki* BMP123+SX, *Bacillus thuringiensis* subsp. *Kurstaki* SA-11+SX, *Bacillus thuringiensis* subsp. *Kurstaki* SA-12+SX, *Bacillus thuringiensis* subsp. *Kurstaki* EG7841+SX, *Bacillus thuringiensis* subsp. *Kurstaki* EVB113-19+SX, *Bacillus thuringiensis* subsp. *Kurstaki* F810+SX, *Bacillus thuringiensis* subsp. *Tenebriosis* NB176+SX, *Bacillus thuringiensis* var. *israelensis* serotype H-14+SX, *Bacillus thuringiensis* var. *israelensis* BMP144+SX, *Bacillus thuringiensis* var. *aegypti*+SX, *Bacillus thuringiensis* var. *colmeri*+SX, *Bacillus thuringiensis* var. *darmstadiensis* 24-91+SX, *Bacillus thuringiensis* var. *dendrolimus*+SX, *Bacillus thuringiensis* var. *galleriae*+SX, *Bacillus thuringiensis* var. *japonensis buibui*+SX, *Bacillus thuringiensis* subsp. *morrisoni*+SX, *Bacillus thuringiensis* var. *san diego*+SX, *Bacillus thuringiensis* subsp. *Thuringiensis* MPPL002+SX, *Bacillus thuringiensis* var. 7216+SX, *Bacillus thuringiensis* var. T36+SX, *Bacillus* sp. AQ175+SX, *Bacillus* sp. AQ177+SX, *Bacillus* sp. AQ178+SX, *Bacillus sphaericus* 2362+SX, *Bacillus sphaericus* Serotype H5a5b+SX, *Bacillus sphaericus* ABTS1743+SX, BT crop protein Cry1Ab+SX, BT crop protein Cry1Ac+SX, BT crop protein Cry1Fa+SX, BT crop protein Cry1A.105+SX, BT crop protein Cry2Ab+SX, BT crop protein Vip3A+SX, BT crop protein Cry3A+SX, BT crop protein Cry3Ab+SX, BT crop protein Cry3Bb+SX, BT crop protein Cry34Abl/Cry35Abl+SX, *Beauveria bassiana* ATCC74040+SX, *Beauveria bassiana* GHA+SX, *Beauveria bassiana* ANT-03+SX, *Beauveria brongniartii*+SX, *Paecilomyces fumosoroseus*+SX, *Paecilomyces lilacinus*+SX, *Paecilomyces tenuipes* T1+SX, *Verticillium lecani* NCIM1312+SX, *Arthrobotrys dactyloides*+SX, *Bacillus firmus* 1-1582+SX, *Bacillus firmus* GB-126+SX, *Bacillus megaterium*+SX, *Hirsutella rhossiliensis*+SX, *Hirsutella minnesotensis*+SX, *Monacrosporium phymatopagum*+SX, *Pasteuria nishizawae*+SX, *Pasteuria penetrans*+SX, *Pasteuria usgae*+SX, *Verticillium* chlamydosporium+SX, Harpin protein+SX, *Adoxophyes orana* granulosis virus+SX,

*Anticarsia gemmatalis* mNPV+SX, *Autographa californica* mNPV FV #11+SX, *Burkholderia rinojensis* A396+SX, *Chromobacterium subtsugae* PRAA4-1T+SX, *Cydia pomonella* GV V15+SX, *Cydia pomonella* GV V22+SX, *Cryptophlebia leucotreta* GV+SX, *Dendrolimus punctatus* cypovirus+SX, *Helicoverpa armigera* NPV BV-0003+SX, *Helicoverpa zea* NPV+SX, *Hirsutella thompsonii*+SX, *Lagenidium giganteum*+SX, *Lecanicillium lecanii* KVO1+SX, *Lymantria dispar* NPV+SX, *Mamestra brassicae* NPV+SX, *Mamestra configurata* NPV+SX, *Metarhizium anisopliae* F52+SX, *Metarhizium flavoviride*+SX, *Neodiprion abietis* NPV+SX, *Neodiprion lecontei* NPV+SX, *Neodiprion sertifer* NPV+SX, *Nosema locustae*+SX, *Orgyia pseudotsugata* NPV+SX, *Paecilomyces fumosoroseus* Apopka97+SX, *Paenibacillus popilliae*+SX, *Pieris rapae* GV+SX, *Plodia interpunctella* GV+SX, *Serratia entomophila*+SX, *Spodoptera exigua* mNPV+SX, *Spodoptera littoralis* mNPV+SX, *Spodoptera litura* NPV+SX, *Paecilomyces lilacinus* 251+SX, *Pasteuria thoynei*+SX, *Dactyllela ellipsospora*+SX, *Dectylaria thaumasia*+SX.

Combinations of the Present ingredient in the above Subgroup a-9 and the Present compound:

abamectin+SX, fluazaindolizine+SX, fluensulfone+SX, fluopyram+SX, tioxazafen+SX.

Combinations of the Present ingredient in the above Subgroup a-10 and the Present compound:

spinetoram+SX, spinosad+SX, emamectin-benzoate+SX, lepimectin+SX, milbemectin+SX, hydroprene+SX, kinoprene+SX, methoprene+SX, fenoxycarb+SX, pyriproxyfen+SX, methyl bromide+SX, chloropicrin+SX, sulfuryl fluoride+SX, sodium aluminium fluoride or chiolite+SX, borax+SX, boric acid+SX, disodium octaborate+SX, sodium borate+SX, sodium metaborate+SX, tartar emetic+SX, dazomet+SX, metam+SX, pymetrozine+SX, pyrifluquinazone+SX, clofentezine+SX, hexythiazox+SX, diflovidazin+SX, etoxazole+SX, diafenthiuron+SX, azocyclotin+SX, cyhexatin+SX, fenbutatin oxide+SX, propargite+SX, tetradifon+SX, chlorfenapyr+SX, DNOC+SX, sulfluramid+SX, bensultap+SX, cartap+SX, cartap hydrochloride+SX, thiocyclam+SX, thiosultap-disodium+SX, thiosultap-monosodium+SX, bistrifluron+SX, chlorfluazuron+SX, diflubenzuron+SX, fluazuron+SX, flucycloxuron+SX, flufenoxuron+SX, hexaflumuron+SX, lufenuron+SX, novaluron+SX, noviflumuron+SX, teflubenzuron+SX, triflumuron+SX, buprofezin+SX, cyromazine+SX, chromafenozide+SX, halofenozide+SX, methoxyfenozide+SX, tebufenozide+SX, amitraz+SX, hydramethylnon+SX, acequinocyl+SX, fluacrypyrim+SX, bifenazate+SX, fenazaquin+SX, fenpyroximate+SX, pyridaben+SX, pyrimidifen+SX, tebufenpyrad+SX, tolfenpyrad+SX, rotenone+SX, indoxacarb+SX, metaflumizone+SX, spirodiclofen+SX, spiromesifen+SX, spirotetramat+SX, aluminium phosphide+SX, calcium phosphide+SX, phosphine+SX, zinc phosphide+SX, calcium cyanide+SX, potassium cyanide+SX, sodium cyanide+SX, cyenopyrafen+SX, cyflumetofen+SX, pyflubumide+SX, flonicamid+SX, azadirachtin+SX, benzoximate+SX, bromopropylate+SX, chinomethionat+SX, dicofol+SX, pyridalyl+SX, lime sulfur+SX, sulfur+SX, machine oil+SX, nicotine+SX, nicotine-sulfate+SX, afidopyropen+SX, flometoquin+SX, metoxadiazone+SX, pyriminostrobin+SX, N-[3-chloro-1-(pyridin-3-yl)-1H-pyrazol-4-yl]-N-ethyl-3-(3,3,3-trifluoropropylsulfanyl)propaneamide (1477919-27-9)+SX, N-[3-chloro-1-(pyridin-3-yl)-1H-pyrazol-4-yl]-N-ethyl-3-(3,3,3-trifluoropropanesulfinyl)propaneamide (1477923-37-7)+SX, 5-(1,3-dioxan-2-yl)-4-[4-(trifluoromethyl)benzyloxy]pyrimidine (1449021-97-9)+SX, 2-[3-(ethanesulfonyl)pyridin-2-yl]-5-(trifluoromethanesulfonyl)benzoxazole (1616678-32-0)+SX, 4-[5-(3,5-dichlorophenyl)-5-(trifluoromethyl)-4,5-dihydro-1,2-oxazol-3-yl]-2-methyl-N-(1-oxothietan-3-yl)benzamide (1241050-20-3)+SX, 3-methoxy-N-(5-{5-(trifluoromethyl)-5-[3-(trifluoromethyl)phenyl]-4,5-dihydro-1,2-oxazol-3-yl}indan-1-yl)propaneamide (1118626-57-5)+SX, 3-(4-chloro-2,6-dimethylphenyl)-4-[(ethoxycarbonyl)oxy]-8-methoxy-1-methyl-1,8-diazaspiro[4.5]dec-3-en-2-one (1229023-00-0)+SX, N-[2-bromo-6-chloro-4-(1,1,1,2,3,3,3-heptafluoropropan-2-yl)phenyl]-3-{ethyl[(pyridin-4-yl)carbonyl]amino}-2-methoxybenzamide (1429513-53-0)+SX, N-[2-bromo-6-chloro-4-(1,1,1,2,3,3,3-heptafluoropropan-2-yl)phenyl]-3-[ethyl(4-cyanobenzoyl)amino]-2-methoxybenzamide (1609007-65-9)+SX, N-[2-bromo-6-difluoromethoxy-4-(1,1,1,2,3,3,3-heptafluoropropan-2-yl)phenyl]-3-{methyl[(pyridin-4-yl)carbonyl]amino}-2-methoxybenzamide (1630969-78-6)+SX, 1-{2-fluoro-4-methyl-5-[(2,2,2-trifluoroethyl)sulfinyl]phenyl}-3-(trifluoromethyl)-1H-1,2,4-triazol-5-amine (885026-50-6)+SX, 3-endo-[2-propoxy-4-(trifluoromethyl)phenoxy]-9-{[5-(trifluoromethyl)pyridin-2-yl]oxy}-9-azabicyclo[3.3.1]nonane (1332838-17-1)+SX.

Combinations of the Present ingredient in the above Subgroup b-1 and the Present compound:

benalaxyl+SX, benalaxyl-M+SX, furalaxyl+SX, metalaxyl+SX, metalaxyl-M+SX, oxadixyl+SX, ofurace+SX.

Combinations of the Present ingredient in the above Subgroup b-2 and the Present compound:

benomyl+SX, carbendazim+SX, fuberidazole+SX, thiabendazole+SX, thiophanate+SX, thiophanate-methyl+SX.

Combination of the Present ingredient in the above Subgroup b-3 and the Present compound:

ethaboxam+SX.

Combinations of the Present ingredient in the above Subgroup b-4 and the Present compound:

benodanil+SX, flutolanil+SX, mepronil+SX, isofetamid+SX, fenfuram+SX, carboxin+SX, oxycarboxin+SX, thifluzamide+SX, benzovindiflupyr+SX, bixafen+SX, fluxapyroxad+SX, furametpyr+SX, isopyrazam+SX, penflufen+SX, penthiopyrad+SX, sedaxane+SX, pydiflumetofen+SX, boscalid+SX, pyraziflumid+SX, fluindapyr+SX, 3-(difluoromethyl)-N-methoxy-1-methyl-N-[(1R)-1-methyl-2-(2,4,6-trichlorophenyl)ethyl]pyrazole-4-carboxamide (1639015-48-7)+SX, 3-(difluoromethyl)-N-methoxy-1-methyl-N-[(1S)-1-methyl-2-(2,4,6-trichlorophenyl)ethyl]pyrazole-4-carboxamide (1639015-49-8)+SX, N-cyclopropyl-3-(difluoromethyl)-5-fluoro-N-(5-chloro-2-isopropylbenzyl)-1-methyl-1H-pyrazole-4-carboxamide (1255734-28-1)+SX, 3-(difluoromethyl)-1-methyl-N-(1,1,3-trimethylindan-4-yl)pyrazole-4-carboxamide (141573-94-6)+SX, 3-(difluoromethyl)-1-methyl-N-[(3R)-1,1,3-trimethylindan-4-yl]pyrazole-4-carboxamide (1352994-67-2)+SX, 3-(difluoromethyl)-N-[(3R)-7-fluoro-1,1,3-trimethylindan-4-yl]-1-methylpyrazole-4-carboxamide (1513466-73-3)+SX.

Combinations of the Present ingredient in the above Subgroup b-5 and the Present compound:

azoxystrobin+SX, coumoxystrobin+SX, enoxastrobin+SX, flufenoxystrobin+SX, picoxystrobin+SX, pyraoxystrobin+SX, mandestrobin+SX, pyraclostrobin+SX, pyrametostrobin+SX, triclopyricarb+SX, kresoxim-methyl+SX, trifloxystrobin+SX, dimoxystrobin+SX, fenaminstrobin+SX, metominostrobin+SX, orysastrobin+SX, famoxadone+SX, fluoxastrobin+SX, fenamidone+SX, pyribencarb+SX.

Combinations of the Present ingredient in the above Subgroup b-6 and the Present compound:

cyazofamid+SX, amisulbrom+SX, binapacryl+SX, meptyldinocap+SX, dinocap+SX, fluazinam+SX.

Combination of the Present ingredient in the above Subgroup b-7 and the Present compound:
silthiofam+SX.

Combinations of the Present ingredient in the above Subgroup b-8 and the Present compound:
cyprodinil+SX, mepanipyrim+SX, pyrimethanil+SX.

Combinations of the Present ingredient in the above Subgroup b-9 and the Present compound:
fenpiclonil+SX, fludioxonil+SX.

Combinations of the Present ingredient in the above Subgroup b-10 and the Present compound:
biphenyl+SX, chloroneb+SX, dicloran+SX, quintozene+SX, tecnazene+SX, tolclofos-methyl+SX.

Combinations of the Present ingredient in the above Subgroup b-11 and the Present compound:
azaconazole+SX, bitertanol+SX, bromuconazole+SX, cyproconazole+SX, difenoconazole+SX, diniconazole+SX, diniconazole-M+SX, epoxiconazole+SX, etaconazole+SX, fenbuconazole+SX, fluquinconazole+SX, flusilazole+SX, flutriafol+SX, hexaconazole+SX, imibenconazole+SX, ipconazole+SX, ipfentrifluconazole+SX, mefentrifluconazole+SX, metconazole+SX, myclobutanil+SX, penconazole+SX, propiconazole+SX, simeconazole+SX, tebuconazole+SX, tetraconazole+SX, triadimefon+SX, triadimenol+SX, triticonazole+SX, prothioconazole+SX, triforine+SX, pyrifenox+SX, pyrisoxazole+SX, fenarimol+SX, nuarimol+SX, imazalil+SX, oxpoconazole+SX, oxpoconazole fumarate+SX, pefurazoate+SX, prochloraz+SX, triflumizole+SX.

Combinations of the Present ingredient in the above Subgroup b-12 and the Present compound:
dimethomorph+SX, flumorph+SX, pyrimorph+SX, benthiavalicarb+SX, benthivalicarb-isopropyl+SX, iprovalicarb+SX, valifenalate+SX, mandipropamid+SX.

Combination of the Present ingredient in the above Subgroup b-13 and the Present compound:
oxathiapiprolin+SX.

Combination of the Present ingredient in the above Subgroup b-14 and the Present compound:
picarbutrazox+SX.

Combinations of the Present ingredient in the above Subgroup b-15 and the Present compound:
ferbam+SX, mancozeb+SX, maneb+SX, metiram+SX, propineb+SX, thiram+SX, zineb+SX, ziram+SX.

Combinations of the Present ingredient in the above Subgroup b-16 and the Present compound:
captan+SX, captafol+SX, folpet+SX.

Combinations of the Present ingredient in the above Subgroup b-17 and the Present compound: *Agrobacterium radiobactor* K84+SX, *Agrobacterium radiobactor* K1026+SX, *Bacillus amyloliquefaciens* QST713+SX, *Bacillus amyloliquefaciens* FZB24+SX, *Bacillus amyloliquefaciens* MBI600+SX, *Bacillus amyloliquefaciens* D747+SX, *Bacillus amyloliquefaciens* AT332+SX, *Bacillus amyloliquefaciens* IN937a+SX, *Bacillus amyloliquefaciens* FZB42+SX, *Bacillus amyloliquefaciens* B3+SX, *Bacillus amyloliquefaciens* PTA-4838+SX, *Bacillus pumilus* GB34+SX, *Bacillus pumilus* QST2808+SX, *Bacillus pumilus* BUF-33+SX, *Bacillus pumilus* AQ717+SX, *Bacillus simplex* CGF2856+SX, *Bacillus subtilis* QST713+SX, *Bacillus subtilis* HAI0404+SX, *Bacillus subtilis* Y1336+SX, *Bacillus subtilis* GB03+SX, *Bacillus subtilis* QST714+SX, *Bacillus subtilis* AQ743+SX, *Bacillus subtilis* AQ153+SX, *Bacillus subtilis* MBI600+SX, *Bacillus subtilis* D747+SX, *Bacillus subtilis* QST30002/AQ30002+SX, *Bacillus subtilis* QST30004/AQ30004+SX, *Bacillus subtilis* DB101+SX, *Bacillus subtilis* IAB/BS03+SX, *Bacillus subtilis* var. *Amyloliquefaciens* FZB24+SX, Variovorax *paradoxus* CGF4526+SX, *Erwinia carotovora* subsp. *carotovora* CGE234M403+SX, *Pseudomonas fluorescens* G7090+SX, *Pseudomonas fluorescens* CL145A+SX, *Pseudomonas fluorescens* A506+SX, *Pseudomonas fluorescens* 1629RS+SX, *Talaromyces flavus* SAY-Y-94-01+SX, *Trichoderma atroviride* SKT-1+SX, *Trichoderma atroviride* CNCM 1-1237+SX, *Trichoderma atroviride* SC1+SX, *Trichoderma harzianum* T39+SX, *Trichoderma harzianum* DSM 14944+SX, *Trichoderma harzianum* DB104+SX, *Trichoderma harzianum* 21+SX, *Trichoderma harzianum* kd+SX, *Trichoderma harzianum* SF+SX, *Trichoderma harzianum* ESALQ-1306+SX, *Trichoderma harzianum* ESALQ-1303+SX, *Trichoderma harzianum* IIHR-Th-2+SX, *Trichoderma harzianum* MO1+SX, *Bacillus licheniformis* HB-2+SX, *Bacillus licheniformis* SB3086+SX, *Burkholderia cepacia*+SX, *Candida oleophila* O+SX, *Candida saitoana*+SX, *Chaetomium cupreum*+SX, *Clonostachys rosea*+SX, *Coniothyrium minitans* CON/M/91-8+SX, *Coniothyrium minitans* CGMCC8325+SX, *Cryptococcus albidus*+SX, *Fusarium oxysporum* Fo47+SX, *Gliocladium catenulatum* J1446+SX, *Paenibacillus polymyxa* AC-1+SX, *Pantoea agglomerans* E325+SX, *Phlebiopsis gigantea*+SX, *Pseudomonas aureofaciens* TX-1+SX, *Pseudomonas chlororaphis* MA342+SX, *Pseudomonas chlororaphis* 63-28+SX, *Pseudomonas syringae* MA-4+SX, *Pseudomonas syringae* 742RS+SX, *Pseudozyma flocculosa* PF-A22UL+SX, *Pythium oligandrum* DV74+SX, *Streptomyces griseoviridis* K61+SX, *Streptomyces lydicus* WYCD108US+SX, *Streptomyces lydicus* WYEC108+SX, *Talaromyces flavus* SAY-Y-94-01+SX, *Trichoderma asperellum* ICC012+SX, *Trichoderma asperellum* T34+SX, *Trichoderma polysporum* IMI 206039+SX, *Trichoderma stromaticum*+SX, Harpin protein+SX.

Combinations of the Present ingredient in the above Subgroup b-18 and the Present compound:
bupirimate+SX, dimethirimol+SX, ethirimol+SX, hymexazole+SX, octhilinone+SX, oxolinic acid+SX, diethofencarb+SX, zoxamide+SX, pencycuron+SX, fluopicolide+SX, phenamacril+SX, diflumetorim+SX, tolfenpyrad+SX, fentin acetate+SX, fentin chloride+SX, fentin hydroxide+SX, ametoctradin+SX, blasticidin-S+SX, kasugamycin+SX, streptomycin+SX, oxytetracycline+SX, quinoxyfen+SX, proquinazid+SX, chlozolinate+SX, dimethachlone+SX, iprodione+SX, procymidone+SX, vinclozolin+SX, edifenphos+SX, iprobenfos+SX, pyrazophos+SX, isoprothiolane+SX, etridiazole+SX, iodocarb+SX, propamocarb+SX, prothiocarb+SX, aldimorph+SX, dodemorph+SX, fenpropidin+SX, fenpropimorph+SX, piperalin+SX, spiroxamine+SX, tridemorph+SX, fenhexamid+SX, fenpyrazamine+SX, pyributicarb+SX, naftifine+SX, terbinafine+SX, polyoxins+SX, phthalide+SX, pyroquilon+SX, tricyclazole+SX, carpropamid+SX, diclocymet+SX, fenoxanil+SX, tolprocarb+SX, acibenzolar-S-methyl+SX, probenazole+SX, tiadinil+SX, isotianil+SX, laminarin+SX, cymoxanil+SX, fosetyl+SX, teclofthalam+SX, triazoxide+SX, flusulfamide+SX, diclomezine+SX, methasulfocarb+SX, cyflufenamid+SX, metrafenone+SX, pyriofenone+SX, dodine+SX, flutianil+SX, ferimzone+SX, tebufloquin+SX, validamycin+SX, basic copper chloride+SX, copper(II) hydroxide+SX, basic copper sulfate+SX, Dodecylbenzenesulphonic acid bisethylenediamine copper [II] salt (DBEDC)+SX, organic copper+SX, sulfur+SX, chlorothalonil+SX, dichlofluanid+SX, tolylfluanid+SX, guazatine+SX, iminoctadine+SX, anilazine+SX, dithianon+SX, chinomethionat+SX, fluoroimide+SX, dipymetitrone+SX, quinofumelin+SX, dichlobentiazox+SX, 3-chloro-5-phenyl-6-methyl-4-(2,6-difluorophenyl)pyridazine (1358061-55-8)+SX, fenpicoxamid+SX, N'-[4-({3-[(4-chlorophenyl)methyl]-1,2,4-thiadiazol-5-yl}oxy)-2,5-dimethylphenyl]-N-ethyl-N-methylmethanimidamide (1202781-91-6)+SX, 2-{3-[2-(1-{[3,5-bis(difluoromethyl)-1H-pyrazol-1-yl]acetyl}piperidin-4-yl)-1,3-thiazol-4-yl]-4,5-dihydro-1,2-oxazol-5-yl}-3-chlorophenyl=methanesulfonate (1360819-11-9)+SX, 4-(2-bromo-4-fluorophenyl)-N-(2-chloro-6-fluorophenyl)-1,3-dimethyl-1H-pyrazol-5-amine (1362477-26-6)+SX, 2,2-dimethyl-9-fluoro-5-(quinolin-3-yl)-2,3-dihydrobenzo[f][1,4]oxazepine (1207749-50-5)+SX, 2-[6-(3-fluoro-4-methoxyphenyl)-5-methylpyridin-2-yl]quinazoline (1257056-97-5)+SX, 5-fluoro-2-[(4-methylphenyl)methoxy]-4-pyrimidineamine (1174376-25-0)+SX, 5-fluoro-4-imino-3-methyl-1-tosyl-3,4-dihydropyrimidin-2(1H)-one (1616664-98-2)+SX, N'-(2,5-dimethyl-4-phenoxyphenyl)-N-ethyl-N-methylmethanimidamide (1052688-31-9)+SX, N'-{4-[(4,5-dichlorothiazol-2-yl)oxy]-2,5-dimethylphenyl}-N-ethyl-N-methylmethanimidamide (929908-57-6)+SX, ethyl (2Z)-3-amino-2-cyano-3-phenylacrylate (39491-78-6)+SX, N-[(2-chlorothiazol-5-yl)methyl]-N-ethyl-6-methoxy-3-nitropyridin-2-amine (1446247-98-8)+SX, 1-[2-({[1-(4-chlorophenyl)-1H-pyrazol-3-yl]oxy}methyl)-3-methylphenyl]-4-methyl-5-oxo-4,5-dihydro-1H-tetrazole (1472649-01-6)+SX, (4-phenoxyphenyl)methyl 2-amino-6-methylpyridine-3-carboxylate (1531626-08-0)+SX, Colletochlorin B+SX.

Combinations of the Present ingredient in the above Subgroup c-1 and the Present compound:

IAA {(1H-indol-3-yl)acetic acid}+SX, IBA (4-(1H-indol-3-yl)butyric acid)+SX, ethychlozate+SX, 2-(naphthalen-1-yl)acetamide+SX, 4-CPA (4-chlorophenoxyacetic acid)+SX, sodium 1-naphthaleneacetate+SX, MCPB (4-(4-chloro-2-methylphenoxy)butyric acid)+SX, Maleic hydrazide+SX, ethephon+SX, AVG (aminoethoxyvinylglycine)+SX, 1-methylcyclopropene+SX, chlormequat-chloride+SX, mepiquat-chloride+SX, Gibberellin A3+SX, Gibberellin A+SX, uniconazole-P+SX, pacrobutrazol+SX, flurprimidol+SX, prohexandione-calcium+SX, trinexapac-ethyl+SX, daminozide+SX, abscisic acid+SX, Kinetin+SX, 6-benzylaminopurine+SX, forchlorfenuron+SX, thidiazuron+SX, prohydrojasmon+SX, 5-aminolevulinic acid hydrochloride+SX, pendimethalin+SX, decan-1-ol+SX, butralin+SX, ancymidol+SX, mefluidide+SX, calcium peroxide+SX, hymexazol+SX, isoprothiolane+SX, choline chloride+SX, cyanamide+SX, pyraflufen-ethyl+SX, diquat+SX, streptmycin+SX, sodium cyanate+SX, calcium polysulfide+SX, calcium chloride+SX, calcium sulfate+SX, calcium carbonate+SX, calcium formate+SX, oxidized glutathione+SX, Cyclanilide+SX, Flumetralin+SX, Chlorpropham+SX, Dikegulac+SX, Dimethipin+SX, Tribufos+SX, sintofen+SX, triapenthenol+SX, 2,3,5-triiodobenzoic acid+SX, inabenfide+SX, cloprop+SX, [4-oxo-4-(2-phenylethyl)amino]butyric acid+SX, methyl 5-(trifluoromethyl)benzo[b]thiophene-2-carboxylate+SX, 3-[(6-chloro-4-phenylquinazolin-2-yl)amino]-1-propanol+SX.

Combinations of the Present ingredient in the above Subgroup c-2 and the Present compound: Glomus spp.+SX, Glomus intraradices+SX, Glomus mosseae+SX, Glomus aggregatum+SX, Glomus etunicatum+SX.

Combinations of the Present ingredient in the above Subgroup c-3 and the Present compound: Bradyrhizobium elkani+SX, Bradyrhizobium japonicum+SX, Bradyrhizobium lupini+SX, Rhizobium leguminosarum bv. trifolii+SX, Rhizobium leguminosarum bv. phaseoli+SX, Rhizobium leguminosarum bv. viciae+SX, Sinorhizobium meliloti+SX, Rhizobium spp.+SX.

Combinations of the Present ingredient in the above Group (d) and the Present compound:

benoxacor+SX, cloquintocet+SX, cloquintocet-mexyl+SX, cyometrinil+SX, cyprosulfamide+SX, dichlormid+SX, dicyclonone+SX, disulfoton+SX, dymron+SX, fenchlorazole+SX, fenchlorazole-ethyl+SX, fenclorim+SX, flurazole+SX, furilazole+SX, fluxofenim+SX, isoxadifen+SX, isoxadifen-ethyl+SX, mefenpyr+SX, mefenpyr-ethyl+SX, mefenpyr-diethyl+SX, mephenate+SX, oxabetrinil+SX, 1,8-naphthalic anhydride+SX, 1,8-octamethylene diamine+SX, CSB (1-bromo-4-[(chloromethyl)sulfonyl]benzene)+SX, AD-67 (4-(dichloroacetyl)-1-oxa-4-azaspiro[4.5]decane)+SX, DKA-24 (2,2-dichloro-N-[2-oxo-2-(2-propenylamino)ethyl]-N-(2-propenyl)acetamide)+SX, MG191 (2-(dichloromethyl)-2-methyl-1,3-dioxolane)+SX, MG-838 (2-propenyl 1-oxa-4-azaspiro[4.5]decane-4-carbodithioate)+SX, PPG-1292 (2,2-dichloro-N-(1,3-dioxan-2-ylmethyl)-N-(2-propenyl)acetamide)+SX, R-29148 (3-(dichloroacetyl)-2,2,5-trimethyl-1,3-oxazolidine)+SX, R-28725 (3-(dichloroacetyl)-2,2-dimethyl-1,3-oxazolidine)+SX, TI-35 (1-(dichloroacetyl)azepane)+SX, CL-304415 (4-carboxy-3,4-dihydro-2H-1-benzopyran-4-acetic acid)+SX.

Combinations of the Present ingredient in the above Group (e) and the Present compound:

DMC (1,1-bis(4-chlorophenyl)ethanol)+SX, FDMC (1,1-bis(4-chlorophenyl)-2,2,2-trifluoroethanol)+SX, bucarpolate+SX, N,N-dibutyl-4-chlorobenzenesulfonamide+SX, dietholate+SX, diethylmaleate+SX, 1-dodecyl-1H-imidazole+SX, N-(2-ethylhexyl)-8,9,10-trinorborn-5-ene-2,3-dicarboximide+SX, PSCP (phenylsaligenin cyclic phosphate)+SX, piperonyl butoxide+SX, piperonyl cyclonene+SX, piprotal+SX, propyl isome+SX, safroxan+SX, sesamex+SX, sesamolin+SX, sulfoxide+SX, tribufos+SX, TBPT (S,S,S-tributyl phosphorotrithioate)+SX, ETP (1,1,1-trichloro-2,3-expoxypropane)+SX, ETN (1,2-epoxy-1,2,3,4-tetrahydronaphthalene)+SX, TPP (triphenyl phosphate)+SX, Verbutin+SX.

Examples of the pest on which the Present compound has control efficacies include harmful arthropods such as harmful insects and harmful mites. Specific examples of the pest include, but are not limited to, the followings.

Hemiptera:

from the family Delphacidae, for example, small brown planthopper (*Laodelphax striatella*), brown planthopper (*Nilaparvata lugens*), white-backed planthopper (*Sogatella furcifera*), corn planthopper (*Peregrinus maidis*), cereal leafhopper (*Javesella pellucida*), sugarcane leafhopper (*Perkinsiella saccharicida*), and *Tagosodes orizicolus*; from the family Cicadellidae, for example, green rice leafhopper (*Nephotettix cincticeps*), green paddy leafhopper (*Nephotettix virescens*), rice leafhopper (*Nephotettix nigropictus*), zigzag-striped leafhopper (*Recilia dorsalis*), tea green leafhopper (*Empoasca onukii*), potato leafhopper (*Empoasca fabae*), corn leafhopper (*Dalbulus maidis*), and rice leafhopper (*Cofana spectra*);

from the family Cercopidae, for example, *Mahanarva posticata* and *Mahanarva fimbriolata*;

from the family Aphididae, for example, bean aphid (*Aphis fabae*), soybean aphid (*Aphis glycines*), cotton aphid (*Aphis gossypii*), green apple aphid (*Aphis pomi*), apple aphid (*Aphis spiraecola*), green peach aphid (*Myzus persicae*), leaf-curling plum aphid (*Brachycaudus helichrysi*), cabbage aphid (*Brevicoryne brassicae*), rosy apple aphid (*Dysaphis plantaginea*), false cabbage aphid (*Lipaphis* erysimi), potato aphid (*Macrosiphum euphorbiae*), foxglove aphid (*Aulacorthum solani*), lettuce aphid (*Nasonovia ribisnigri*), grain aphid (*Rhopalosiphum padi*), corn aphid (*Rhopalosiphum maidis*), brown citrus aphid (*Toxoptera citricida*), mealy plum aphid (*Hyalopterus pruni*), cane aphid (*Melanaphis sacchari*), black rice root aphid (*Tetraneura nigriabdominalis*), sugarcane cottony aphid (*Ceratovacuna lanigera*), and apple woolly aphid (*Eriosoma lanigerum*);

from the family Phylloxeridae, for example, grapevine *phylloxera* (*Daktulosphaira vitifoliae*), Pecan *phylloxera* (*Phylloxera devastatrix*), Pecan leaf *phylloxera* (*Phylloxera notabilis*), and Southern pecan leaf *phylloxera* (*Phylloxera russellae*);

from the family Adelgidae, for example, hemlock woolly aphid (*Adelges tsugae*), balsam woolly aphid (*Adelges piceae*), and *Aphrastasia pectinatae*;

from the family Pentatomidae, for example, black rice bug (*Scotinophara lurida*), Malayan rice black bug (*Scotinophara coarctata*), common green stink bug (*Nezara antennata*), white-spotted spined bug (*Eysarcoris aeneus*), lewis spined bug (*Eysarcoris lewisi*), white-spotted bug (*Eysarcoris ventralis*), *Eysarcoris* annamita, brown marmorated stink bug (*Halyomorpha halys*), green plant bug (*Nezara viridula*), brown stink bug (*Euschistus heros*), red banded stink bug (*Piezodorus guildinii*), *Oebalus pugnax*, and *Dichelops melacanthus*;

from the family Cydnidae, for example, Burrower brown bug (*Scaptocoris castanea*);

from the family Alydidae, for example, bean bug (*Riptortus pedestris*), corbett rice bug (*Leptocorisa chinensis*), and rice bug (*Leptocorisa acuta*);

from the family Coreidae, for example, *Cletus punctiger* and Australian leaf-footed bug (*Leptoglossus australis*);

from the family Lygaeidae, for example, oriental chinch bug (*Caverelius saccharivorus*), seed bug (*Togo hemipterus*), and chinch bug (*Blissus leucopterus*); from the family Miridae, for example, rice leaf bug (*Trigonotylus caelestialium*), sorghum plant bug (*Stenotus rubrovittatus*), wheat leaf bug (*Stenodema calcarata*), and American tarnished plant bug (*Lygus lineolaris*); from the family Aleyrodidae, for example, greenhouse whitefly (*Trialeurodes vaporariorum*), tobacco whitefly (*Bemisia tabaci*), citrus whitefly (*Dialeurodes citri*), citrus spiny whitefly (*Aleurocanthus spiniferus*), tea spiny whitefly (*Aleurocanthus camelliae*), and *Pealius euryae*; from the family Diaspididae, for example, *Abgrallaspis cyanophylli*, red scale (*Aonidiella aurantii*), San Jose scale (*Diaspidiotus perniciosus*), white peach scale (*Pseudaulacaspis pentagona*), arrowhead scale (*Unaspis yanonensis*), and citrus snow scale (*Unaspis citri*); from the family Coccidae, for example, pink wax scale (*Ceroplastes rubens*);

from the family Margarodidae, for example, fluted scale (*Icerya purchasi*) and seychelles fluted scale (*Icerya seychellarum*);

from the family Pseudococcidae, for example, *Solanum* mealybug (*Phenacoccus solani*), cotton mealybug (*Phenacoccus solenopsis*), Japanese mealybug (*Planococcus kraunhiae*), white peach scale (*Pseudococcus comstocki*), citrus mealybug (*Planococcus citri*), currant mealybug (*Pseudococcus calceolariae*), long-tailed mealybug (*Pseudococcus longispinus*), and tuttle mealybug (*Brevennia rehi*); from the family Psyllidae, for example, citrus psylla (*Diaphorina citri*), two-spotted citrus psyllid (*Trioza erytreae*), pear sucker (*Cacopsylla pyrisuga*), *Cacopsylla chinensis*, potato psyllid (*Bactericera cockerelli*), and Pear psylla (*Cacopsylla pyricola*);

from the family Tingidae, for example, sycamore lace bug (*Corythucha ciliata*), aster tingid (*Corythucha marmorata*), Japanese pear lace bug (*Stephanitis nashi*), and azalea lace bug (*Stephanitis pyrioides*);

from the family Cimicidae, for example, common bed bug (*Cimex lectularius*);

from the family Cicadidae, for example, Giant Cicada (*Quesada gigas*);

from *Triatoma* spp., for example, *Triatoma infestans*; and the others.

Lepidoptera:

from the family Crambidae, for example, rice stem borer (*Chilo suppressalis*), Darkheaded stem borer (*Chilo polychrysus*), white stem borer (*Scirpophaga innotata*), yellow paddy borer (*Scirpophaga incertulas*), *Rupela albina*, rice leaf roller (*Cnaphalocrocis medinalis*), *Marasmia patnalis*, rice leaf roller (*Marasmia exigua*), cotton leaf roller (*Notarcha derogata*), corn borer (*Ostrinia furnacalis*), European corn borer (*Ostrinia nubilalis*), cabbage webworm (*Hellula undalis*), grape leafroller (*Herpetogramma luctuosale*), bluegrass webworm (*Pediasia teterrellus*), rice case-worm (*Nymphula depunctalis*), and Sugarcane borer (*Diatraea saccharalis*);

from the family Pyralidae, for example, lesser cornstalk borer (*Elasmopalpus lignosellus*) and mealworm moth (*Plodia interpunctella*);

from the family Noctuidae, for example, cotton worm (*Spodoptera litura*), beet armyworm (*Spodoptera exigua*), rice armyworm (*Mythimna separata*), cabbage moth (*Mamestra brassicae*), pink borer (*Sesamia inferens*), grass armyworm (*Spodoptera mauritia*), green rice caterpillar (*Naranga aenescens*), *Spodoptera frugiperda*, true armyworm (*Spodoptera exempta*), black cutworm (*Agrotis ipsilon*), beet worm (*Autographa nigrisigna*), rice looper (*Plusia festucae*), soybean looper (*Chrysodeixis includens*), *Trichoplusia* spp., *Heliothis* spp. (such as tobacco budworm (*Heliothis virescens*)), *Helicoverpa* spp. (such as tobacco budworm (*Helicoverpa armigera*) and corn earworm (*Helicoverpa zea*)), velvetbean caterpillar (*Anticarsia gemmatalis*), cotton leafworm (*Alabama argillacea*), and hop vine borer (*Hydraecia immanis*);

from the family Pieridae, for example, common cabbage worm (*Pieris rapae*);

from the family Tortricidae, for example, oriental fruit moth (*Grapholita molesta*), *Grapholita dimorpha*, soybean moth (*Leguminivora glycinivorella*), *Matsumuraeses azukivora*, summer fruit *tortrix* (*Adoxophyes orana fasciata*), smaller tea *tortrix* (*Adoxophyes honmai*), Japanese tea *tortrix* (*Homona magnanima*), apple *tortrix* (*Archips fuscocupreanus*), codling moth (*Cydia pomonella*), sugarcane shoot borer (*Tetramoera schistaceana*), bean shoot borer (*Epinotia aporema*), and citrus fruit borer (*Ecdytolopha aurantiana*);

from the family Gracillariidae, for example, tea leaf roller (*Caloptilia theivora*) and Asiatic apple leaf miner (*Phyllonorycter ringoniella*);

from the family Carposinidae, for example, peach fruit moth (*Carposina sasakii*);

from the family Lyonetiidae, for example, coffee leaf miner (*Leucoptera coffeella*), peach leaf miner (*Lyonetia clerkella*), and *Lyonetia prunifoliella*;

from the family Lymantriidae, for example, *Lymantria* spp. (such as gypsy moth (*Lymantria dispar*)) and *Euproctis* spp. (such as tea lymantriid (*Euproctis pseudoconspersa*));

from the family Plutellidae, for example, diamondback moth (*Plutella xylostella*);

from the family Gelechiidae, for example, peach worm (*Anarsia lineatella*), sweetpotato leaf folder (*Helcystogramma triannulella*), pink bollworm (*Pectinophora gossypiella*), potato moth (*Phthorimaea operculella*), and *Tuta absoluta*;

from the family Arctiidae, for example, American white moth (*Hyphantria cunea*);

from the family Castniidae, for example, giant sugarcane borer (*Telchin licus*);

from the family Cossidae, for example, *Cossus insularis*;

from the family Geometridae, for example, Ascotis selenaria;

from the family Limacodidae, for example, blue-striped nettle grub (*Parasa lepida*);

from the family Stathmopodidae, for example, persimmon fruit moth (*Stathmopoda masinissa*);

from the family Sphingidae, for example, tobacco hornworm (*Acherontia lachesis*);

from the family Sesiidae, for example, *Nokona feralis*;

from the family Hesperiidae, for example, rice skipper (*Parnara guttata*);

from the family Tineidae, for example, casemaking clothes moth (*Tinea translucens*) and common clothes moth (*Tineola bisselliella*);

and the others.

Thysanoptera:

from the family Thripidae, for example, western flower thrips (*Frankliniella occidentalis*), oriental *thrips* (*Thrips palmi*), yellow tea thrips (*Scirtothrips dorsalis*), onion *thrips* (*Thrips tabaci*), eastern flower *thrips* (*Frankliniella intonsa*), rice *thrips* (*Stenchaetothrips biformis*), and Echinothrips americanus;

from the family Phlaeothripidae, for example, aculeated rice *thrips* (*Haplothrips aculeatus*);

and the others.

Diptera:

from the family Anthomyiidae, for example, seedcorn maggot (*Delia platura*) and onion maggot (*Delia antiqua*);

from the family Ulidiidae, for example, sugarbeet root maggot (*Tetanops myopaeformis*);

from the family Agromyzidae, for example, rice leaf miner (*Agromyza oryzae*), tomato leaf miner (*Liriomyza sativae*), chrysanthemum leaf miner (*Liriomyza trifolii*), and pea leafminer (*Chromatomyia horticola*);

from the family Chloropidae, for example, rice stem maggot (*Chlorops oryzae*);

from the family Tephritidae, for example, melon fly (*Bactrocera cucurbitae*), oriental fruit fly (*Bactrocera dorsalis*), Malaysian fruit fly (*Bactrocera latifrons*), olive fruit fly (*Bactrocera oleae*), Queensland fruit fly (*Bactrocera tryoni*), and Mediterranean fruit fly (*Ceratitis capitata*);

from the family Ephydridae, for example, smaller rice leaf miner (*Hydrellia griseola*), whorl maggot (*Hydrellia philippina*), and paddy stem maggot (*Hydrellia sasakii*); from the family Drosophilidae, for example, cherry *drosophila* (*Drosophila suzukii*);

from the family Phoridae, for example, *Megaselia spiracularis*;

from the family Psychodidae, for example, *Clogmia albipunctata*;

from the family Sciaridae, for example, *Bradysia difformis*;

from the family Cecidomyiidae, for example, hessian fly (*Mayetiola destructor*) and paddy gall fly (*Orseolia oryzae*);

from the family Diopsidae, for example, *Diopsis macrophthalma*;

from the family Tipulidae, for example, rice crane fly (*Tipula aino*), common cranefly (*Tipula oleracea*), and European cranefly (*Tipula paludosa*);

from the family Culicidae, for example, southern house mosquito (*Culex pipiens pallens*), dengue mosquito (*Aedes aegypti*), Asian tiger mosquito (*Aedes albopictus*), Chinese malaria mosquito (*Anopheles hyracanus sinensis*), *Culex quinquefasciatus, Culex pipiens molestus* Forskal, and brown house mosquito (*Culex quinquefasciatus*);

from the family Simuliidae, for example, *Prosimulium yezoensis* and *Simulium ornatum*;

from the family Tabanidae, for example, *Tabanus* trigonus;

from the family Muscidae, for example, house fly (*Musca domestica*), false stable fly (*Muscina stabulans*), biting house fly (*Stomoxys calcitrans*), and buffalo fly (*Haematobia irritans*);

from the family Calliphoridae;

from the family Sarcophagidae;

from the family Chironomidae, for example, Chironomus plumosus, Chironomus yoshimatsui, and Glyptotendipes tokunagai;

from the family Fannidae;

and the others.

Coleoptera:

from the family Chrysomelidae, for example, western corn rootworm (*Diabrotica virgifera virgifera*), southern corn rootworm (*Diabrotica undecimpunctata howardi*), northern corn rootworm (*Diabrotica barberi*), Mexican corn rootworm (*Diabrotica virgifera zeae*), banded cucumber beetle (*Diabrotica balteata*), cucurbit beetle (*Diabrotica speciosa*), bean leaf beetle (*Cerotoma trifurcata*), barley leaf beetle (*Oulema melanopus*), cucurbit leaf beetle (*Aulacophora femoralis*), striped flea beetle (*Phyllotreta striolata*), cabbage flea beetle (*Phyllotreta cruciferae*), western black flea beetle (*Phyllotreta pusilla*), cabbage stem flea beetle (*Psylliodes chrysocephala*), Colorado potato beetle (*Leptinotarsa decemlineata*), rice leaf beetle (*Oulema oryzae*), grape colaspis (*Colaspis brunnea*), corn flea beetle (*Chaetocnema pulicaria*), sweet-potato flea beetle (*Chaetocnema confinis*), potato flea beetle (*Epitrix cucumeris*), rice leaf beetle (*Dicladispa armigera*), southern corn leaf beetle (*Myochrous denticollis*), Laccoptera quadrimaculata, and tobacco flea beetle (*Epitrix hirtipennis*);

from the family Carabidae, for example, Seedcorn beetle (*Stenolophus lecontei*), and slender seedcorn beetle (*Clivina impressifrons*);

from the family Scarabaeidae, for example, cupreus chafer (*Anomala cuprea*), soybean beetle (*Anomala rufocuprea*), *Anomala albopilosa*, Japanese beetle (*Popillia japonica*), yellowish elongate chafer (*Heptophylla picea*), European Chafer (*Rhizotrogus majalis*), *Tomarus gibbosus, Holotrichia* spp., *Phyllophaga* spp. (such as June beetle (*Phyllophaga crinita*)), and *Diloboderus* spp. (such as *Diloboderus abderus*);

from the family Curculionidae, for example, coffee bean weevil (*Araecerus coffeae*), sweet-potato weevil (*Cylas formicarius*), West Indian sweet-potato weevil (*Euscepes postfasciatus*), alfalfa weevil (*Hypera postica*), maize weevil (*Sitophilus zeamais*), rice plant weevil (*Echinocnemus squameus*), rice water weevil (*Lissorhoptrus oryzophilus*), *Rhabdoscelus lineaticollis*, boll weevil (*Anthonomus grandis*), nunting billbug (*Sphenophorus venatus*), southern corn billbug (*Sphenophorus callosus*), soybean stalk weevil (*Sternechus subsignatus*), sugarcane weevil (*Sphenophorus levis*), rusty gourd-shaped weevil (*Scepticus griseus*), brown gourd-shaped weevil (*Scepticus uniformis*), Mexican bean weevil (*Zabrotes subfasciatus*), pine beetle (*Tomicus piniperda*), coffee berry borer (*Hypothenemus hampei*), *Aracanthus* spp. (such as *Aracanthus mourei*), and cotton root borer (*Eutinobothrus brasiliensis*);

from the family Tenebrionidae, for example, red meal beetle (*Tribolium castaneum*) and mason beetle (*Tribolium confusum*);

from the family Coccinellidae, for example, twenty-eight-spotted ladybird (*Epilachna vigintioctopunctata*); from the family Bostrychidae, for example, common powder-post beetle (*Lyctus brunneus*);

from the family Ptinidae;

from the family Cerambycidae, for example, citrus long-horned beetle (*Anoplophora malasiaca*) and *Migdolus fryanus*;

from the family Elateridae, for example, *Melanotus okinawensis*, barley wireworm (*Agriotes fuscicollis*), *Melanotus legatus*, *Anchastus* spp., *Conoderus* spp., *Ctenicera* spp., *Limonius* spp., and *Aeolus* spp.;

from the family Staphylinidae, for example, Paederus fuscipes;

from the family Dermestidae, for example, varied carpet beetle (*Anthrenus verbasci*) and hide beetle (*Dermestes maculates*);

from the family Anobiidae, for example, tobacco beetle (*Lasioderma serricorne*) and biscuit beetle (*Stegobium paniceum*);

and the others;

Orthoptera:

from the family Acrididae, for example, oriental migratory locust (*Locusta migratoria*), Moroccan locust (*Dociostaurus maroccanus*), Australian plague locust (*Chortoicetes terminifera*), red locust (*Nomadacris septemfasciata*), brown locust (*Locustana pardalina*), tree locust (*Anacridium melanorhodon*), Italian locust (*Calliptamus italicus*), differential grasshopper (*Melanoplus differentialis*), two-striped grasshopper (*Melanoplus bivittatus*), migratory grasshopper (*Melanoplus sanguinipes*), red-legged grasshopper (*Melanoplus femurrubrum*), clear-winged grasshopper (*Camnula pellucida*), desert locust (*Schistocerca gregaria*), Yellow-winged locust (*Gastrimargus musicus*), spur-throated locust (*Austracris guttulosa*), Japanese grasshopper (*Oxya yezoensis*), rice grasshopper (*Oxya japonica*), and Bombay locust (*Patanga succincta*);

from the family Gryllotalpidae, for example, oriental mole cricket (*Gryllotalpa orientalis*);

from the family Gryllidae, for example, house cricket (*Acheta domestica*) and emma field cricket (*Teleogryllus emma*);

from the family Tettigoniidae, for example, mormon cricket (*Anabrus simplex*);

and the others.

Hymenoptera:

from the family Tenthredinidae, for example, beet sawfly (*Athalia rosae*) and nippon cabbage sawfly (*Athalia japonica*);

from the family Formicidae, for example, *Solenopsis* spp. (such as red imported fire ant (*Solenopsis invicta*) and tropical fire ant (*Solenopsis geminata*)), *Atta* spp. (such as brown leaf-cutting ant (*Atta capiguara*)), *Acromyrmex* spp., *Paraponera clavata*, black house ant (*Ochetellus glaber*), little red ant (*Monomorium pharaonis*), Argentine ant (*Linepithema humile*), *Formica japonica*, *Pristomyrmex punctutus*, *Pheidole noda*, big-headed ant (*Pheidole megacephala*), *Camponotus* spp. (such as *Camponotus japonicus* and *Camponotus obscuripes*), *Pogonomyrmex* spp. (such as western harvester ant (*Pogonomyrmex occidentalis*)), *Wasmania* spp. (such as *Wasmania auropunctata*), and long-legged ant (*Anoplolepis gracilipes*);

from the family Vespidae, for example, Asian giant hornet (*Vespa mandarinia japonica*), *Vespa simillima*, *Vespa analis* Fabriciusi, Asian hornet (*Vespa velutina*), and *Polistes jokahamae*;

from the family Siricidae, for example, pine wood wasp (*Urocerus gigas*);

from the family Bethylidae;

and the others.

Blattodea:

from the family Blattellidae, for example, German cockroach (*Blattella germanica*);

from the family Blattidae, for example, smoky-brown cockroach (*Periplaneta fuliginosa*), American cockroach (*Periplaneta americana*), brown cockroach (*Periplaneta brunnea*), and black cockroach (*Blatta orientalis*); from the family Termitidae, for example, Japanese termite (*Reticulitermes speratus*), Formosan termite (*Coptotermes formosanus*), western drywood termite (*Incisitermes minor*), *Cryptotermes domesticus*, *Odontotermes formosanus*, *Neotermes koshunensis*, *Glyptotermes satsumensis*, *Glyptotermes nakajimai*, *Glyptotermes fuscus*, *Hodotermopsis sjostedti*, *Coptotermes guangzhouensis*, *Reticulitermes amamianus*, *Reticulitermes miyatakei*, *Reticulitermes kanmonensis*, *Nasutitermes takasagoensis*, *Pericapritermes nitobei*, *Sinocapritermes mushae*, and *Cornitermes cumulans*; and the others.

Siphonaptera:

for example, cat flea (*Ctenocephalides felis*), dog flea (*Ctenocephalides canis*), human flea (*Pulex irritans*), oriental rat flea (*Xenopsylla cheopis*), chigoe flea (*Tunga penetrans*), chicken flea (*Echidnophaga gallinacea*), and European rat flea (*Nosopsyllus fasciatus*);

and the others.

Anoplura:

for example, pig louse (*Haematopinus suis*), short-nosed cattle louse (*Haematopinus eurysternus*), sheep biting louse (*Dalmalinia ovis*), *Linognathus seypsus*, *Pediculus humanis*, *Pediculuc humanus corporis*, *Pediculus humanus humanus*, and *Phthirus pubis*;

and the others.

Mallophagida:

for example, *Bovicola* spp. (such as cattle biting louse (*Dalmalinia bovis*) and sheep biting louse (*Dalmalinia ovis*)), *Trichodestes* spp. (such as dog biting louse (*Trichodectes canis*)), *Felicola* spp. (such as cat louse (*Felicola subrostrata*)), *Lipeurus* spp. (such as chicken wing louse (*Lipeurus caponis*)), and Menoponidae family (such as *Trimenopon* spp. and *Menopon* spp.);

and the others.

Acari:

from the family Tetranychidae, for example, common red spider mite (*Tetranychus urticae*), kanzawa spider mite (*Tetranychus kanzawai*), red spider mite (*Tetranychus evansi*), citrus red mite (*Panonychus citri*), fruit-tree red spider mite (*Panonychus ulmi*), and *Oligonychus* spp.; from the family Eriophyidae, for example, Japanese citrus rust mite (*Aculops pelekassi*), *Phyllocoptruta citri*, tomato mite (*Aculops lycopersici*), purple mite (*Calacarus carinatus*), tea rust mite (*Acaphylla theavagrans*), *Eriophyes chibaensis*, apple bud mite (*Aculus schlechtendali*), *Aceria diospyri*, *Aceria tosichella*, and *Shevtchenkella* sp.;

from the family Tarsonemidae, for example, broad mite (*Polyphagotarsonemus latus*);

from the family Tenuipalpidae, for example, *Brevipalpus phoenicis*;

from the family Tuckerellidae;

from the family Ixodidae, for example, *Haemaphysalis longicornis, Haemaphysalis flava, Dermacentor taiwanensis*, American dog tick (*Dermacentor variabilis*), *Dermacentor andersoni, Ixodes ovatus, Ixodes persulcatus, Ixodes ricinus*, black-legged tick (*Ixodes scapularis*), lone star tick (*Amblyomma americanum*), *Amblyomma maculatum*, cattle tick (*Boophilus microplus*), *Boophilus annulatus*, and brown dog tick (*Rhipicephalus sanguineus*);

from the family Acaridae, for example, cereal mite (*Tyrophagus putrescentiae*) and grassland mite (*Tyrophagus similis*);

from the family Pyroglyphidae, for example, American house dust mite (*Dermatophagoides farinae*) and European house dust mite (*Dermatophagoides pteronyssinus*); from the family Cheyletidae, for example, *Cheyletus eruditus, Cheyletus malaccensis, Chelacaropsis moorei*, and *Cheyletiella yasguri;* from the family Sarcoptidae, for example, ear mange mite (*Otodectes cynotis*) and itch mite (*Sarcoptes scabiei*); from the family Demodicidae, for example, dog follicle mite (*Demodex canis*);

from the family Listrophoridae;

from the family Haplochthoniidae;

from the family Macronyssidae, for example, tropical rat mite (*Ornithonyssus bacoti*) and feather mite (*Ornithonyssus sylviarum*);

from the family Dermanyssidae, for example, bird mite (*Dermanyssus gallinae*);

from the family Trombiculidae, for example, *Leptotrombidium akamushi;* and the others.

Araneae:

from the family Eutichuridae, for example, *Cheiracanthium japonicum;* from the family Theridiidae, for example, red-back spider (*Latrodectus hasseltii*);

and the others.

Polydesmida:

from the family Paradoxosomatidae, for example, flat-backed millipede (*Oxidus gracilis*) and *Nedyopus tambanus*;

and the others.

Isopoda:

from the family Armadillidiidae, for example, common pill bug (*Armadillidium vulgare*);

and the others.

Chilopoda:

from the family Scutigeridae, for example, *Thereuonema hilgendorfi;* from the family Scolopendridae, for example, giant tropical centipede (*Scolopendra subspinipes*);

from the family Ethopolyidae, for example, *Bothropolys rugosus;* and the others.

Gastropoda:

from the family Limacidae, for example, tree slug (*Limax marginatus*) and garden tawny slug (*Limax flavus*); from the family Philomycidae, for example, *Meghimatium bilineatum;* from the family Ampullariidae, for example, golden apple snail (*Pomacea canaliculata*);

from the family Lymnaeidae, for example, *Austropeplea ollula;* and the others.

Nematoda:

from the family Aphelenchoididae, for example, rice white-tip nematode (*Aphelenchoides besseyi*);

from the family Pratylenchidae, for example, root lesion nematode (*Pratylenchus coffeae*), *Pratylenchus* brachyurus, California meadow nematode (*Pratylenchus neglectus*), and *Radopholus similis;* from the family Heteroderidae, for example, javanese root-knot nematode (*Meloidogyne javanica*), southern root-knot nematode (*Meloidogyne incognita*), northern root-knot nematode (*Meloidogyne hapla*), soybean cyst nematode (*Heterodera glycines*), potato cyst nematode (*Globodera rostochiensis*), and white potato cyst nematode (*Globodera pallida*);

from the family Hoplolaimidae, for example, *Rotylenchulus reniformis;* from the family Anguinidae, for example, strawberry bud nematode (*Nothotylenchus acris*) and stem nematode (*Ditylenchus dipsaci*);

from the family Tylenchulidae, for example, citrus nematode (*Tylenchulus semipenetrans*);

from the family Longidoridae, for example, dagger nematode (*Xiphinema index*);

from the family Trichodoridae;

from the family Parasitaphelenchidae, for example, pine wilt disease (*Bursaphelenchus xylophilus*);

and the others.

The target harmful insects and harmful mites may have a reduced agent-sensitivity to or a developed agent-resistance to an insecticide or a miticide. However, when the agent-sensitivity is greatly reduced or the agent-resistance is greatly developed, a composition of the present invention comprising an insecticide and a miticide other than the intended insecticide and miticide is preferably used.

The Present compound may be also used to protect a plant from a plant disease caused by insect-borne viruses or insect-borne bacteria.

Examples of the insect-borne viruses are recited as follows.

Rice tungro spherical virus, Rice tungro bacilliform virus, Rice grassy stunt virus, Rice ragged stunt virus, Rice stripe virus, Rice black streaked dwarf virus, Southern rice black-streaked dwarf virus, Rice gall dwarf virus, Rice hoja blanca virus, Rice yellow stunt virus, Rice yellow mottle virus, Rice dwarf virus, Northern cereal mosaic virus, Barley yellow dwarf virus, Barley mild mosaic virus, Barley yellow dwarf virus-PAV, Cereal yellow dwarf virus-RPS, Wheat yellow leaf virus, Oat sterile dwarf virus, Wheat streak mosaic virus, Maize dwarf mosaic virus, Maize stripe virus, Maize chlorotic mottle virus, Maize chlorotic dwarf virus, Maize rayado fino virus, Sugarcane mosaic virus, Fiji disease virus, Sugarcane yellow leaf virus, Soybean mild mosaic virus, Cycas necrotic stunt virus, Soybean dwarf virus, Milk vetch dwarf virus, Soybean mosaic virus, Alfalfa mosaic virus, Bean yellow mosaic virus, Bean common mosaic virus, Southern bean mosaic virus, Peanut stunt virus, Broad bean wilt virus 1, Broad bean wilt virus 2, Broad bean necrosis virus, Broad bean yellow vein virus, Clover yellow vein virus, Peanut mottle virus, Tobacco streak virus, Bean pod mottle virus, Cowpea chlorotic mottle virus, Mung bean yellow mosaic virus, Soybean crinkle leaf virus, Tomato chlorosis virus, Tomato spotted wilt virus, Tomato yellow leaf curl virus, Tomato aspermy virus, Tomato infectious chlorosis virus, Potato leafroll virus, Potato virus Y, Melon yellow spot virus, Melon necrotic spot virus, Watermelon mosaic virus, Cucumber mosaic virus, Zucchini yellow mosaic virus, Turnip mosaic virus, Turnip yellow mosaic virus, Cauliflower mosaic virus, Lettuce mosaic virus, Celery mosaic virus, Beet mosaic virus, Cucurbit chlorotic yellows virus, Capsicum chlorosis virus, Beet pseudo yellows virus, Leak yellow stripe virus, Onion yellow dwarf virus, Sweet potato feathery mottle virus, Sweet potato shukuyo mosaic virus, Strawberry mottle virus, Strawberry mild yellow edge virus, Strawberry pseudo mild yellow edge virus, Strawberry crinkle virus, Strawberry vein banding virus, plum pox virus, Chrysanthemum stem necrosis virus, Impatiens necrotic spot virus, Iris yellow spot virus, Lily mottle cirus, Lilly symptomless virus, Tulip mosaic virus, and the others.

Examples of the insect-borne bacteria are recited as follows.

*Candidatus Phytoplasma oryzae, Candidatus Phytoplasma asteris, Maize bushy stunt phytoplasma, Candidatus Liberbacter asiaticus, Candidatus Liberbacter africanus, Candidatus Liberbacter americanus*, and the others.

The composition for controlling harmful arthropods of the present invention comprises the Present compound and inert carrier(s). The composition for controlling harmful arthropods of the present invention is usually prepared by mixing the Present compound with inert carrier(s) such as solid carrier(s), liquid carrier(s), and gaseous carrier(s), and as needed, adding surfactant(s) and other auxiliary agent(s) for formulation, to formulate into an emulsifiable concentrate, an oil solution, a dust formulation, a granule, a wettable powder, a flowable, a microcapsule, an aerosol, a smoking agent, a poison bait, a resin formulation, a shampoo formulation, a paste-like formulation, a foam, a carbon dioxide formulation, a tablet, or the like. Such formulation may be processed into and used as a mosquito repellent coil, an electric mosquito repellent mat, a liquid mosquito repellent formulation, a smoking agent, a fumigant, a sheet formulation, a spot-on formulation, or a formulation for oral treatment. Also, the composition for controlling harmful arthropods of the present invention may be mixed with other insecticide(s), miticide(s), nematicide(s), fungicide(s), plant growth regulator(s), herbicide(s), or synergist(s).

The composition for controlling harmful arthropods of the present invention usually comprises 0.0001 to 95% by weight of the Present compound.

Examples of the solid carrier to be used in the formulation include fine powders and granules of clays (for example, kaolin clay, diatomaceous earth, bentonite, Fubasami clay, or acid white clay), synthetic hydrated silicon oxides, talcs, ceramics, other inorganic minerals (for example, sericite, quartz, sulfur, active carbon, calcium carbonate, or hydrated silica), chemical fertilizers (for example, ammonium sulfate, ammonium phosphate, ammonium nitrate, urea, or ammonium chloride), and the others; as well as synthetic resins (for example, polyester resins such as polypropylene, polyacrylonitrile, polymethylmethacrylate, and polyethylene terephthalate; nylon resins such as nylon-6, nylon-11, and nylon-66; polyamide resins; polyvinyl chloride, polyvinylidene chloride, vinyl chloride-propylene copolymers, or the others).

Examples of the liquid carrier include water; alcohols (for example, methanol, ethanol, isopropyl alcohol, butanol, hexanol, benzyl alcohol, ethylene glycol, propylene glycol, or phenoxy ethanol); ketones (for example, acetone, methyl ethyl ketone, or cyclohexanone); aromatic hydrocarbons (for example, toluene, xylene, ethyl benzene, dodecyl benzene, phenyl xylyl ethane, or methylnaphthalene); aliphatic hydrocarbons (for example, hexane, cyclohexane, kerosene, or light oil); esters (for example, ethyl acetate, butyl acetate, isopropyl myristate, ethyl oleate, diisopropyl adipate, diisobutyl adipate, or propylene glycol monomethyl ether acetate); nitriles (for example, acetonitrile or isobutyronitrile); ethers (for example, diisopropyl ether, 1,4-dioxane, ethylene glycol dimethyl ether, diethylene glycol dimethyl ether, diethylene glycol monomethyl ether, propylene glycol monomethyl ether, dipropylene glycol monomethyl ether, or 3-methoxy-3-methyl-1-butanol); amides (for example, DMF or dimethylacetamide); sulfoxides (for example, DMSO); propylene carbonate; and vegetable oils (for example, soybean oil or cottonseed oil).

Examples of the gaseous carrier include fluorocarbon, butane gas, LPG (liquefied petroleum gas), dimethyl ether, and carbon dioxide.

Examples of the surfactant include nonionic surfactants such as polyoxyethylene alkyl ethers, polyoxyethylene alkyl aryl ethers, and polyethylene glycol fatty acid esters; and anionic surfactants such as alkyl sulfonates, alkylbenzene sulfonates, and alkyl sulfates.

Examples of the other auxiliary agent for formulation include binders, dispersants, colorants, and stabilizers. Specific examples thereof include casein, gelatin, saccharides (for example, starch, gum arabic, cellulose derivatives, or alginic acid), lignin derivatives, bentonite, water-soluble synthetic polymers (for example, polyvinyl alcohol, polyvinyl pyrrolidone, or polyacrylic acids), acidic isopropyl phosphate, 2,6-di-tert-butyl-4-methylphenol, and BHA (a mixture of 2-tert-butyl-4-methoxyphenol and 3-tert-butyl-4-methoxyphenol).

Examples of the base material of the resin formulation include vinyl chloride polymers, polyurethane, and the others, and plasticizer(s) such as phthalic acid esters (for example, dimethyl phthalate or dioctyl phthalate), adipic acid esters, and stearic acid may be added to these base materials, as needed. The resin formulation may be prepared by mixing the Present compound with the above-mentioned base material, kneading the mixture in a conventional kneading apparatus, followed by molding it by injection molding, extrusion molding, pressure molding, or the like. The resultant resin formulation may be subjected to further molding, cutting procedure, or the like, as needed, to be processed into a shape such as plate, film, tape, net, and string shapes. These resin formulations may be processed into an animal collar, an animal ear tag, a sheet formulation, a trap string, a gardening support, or other products.

Examples of the base material for the poison bait include bait ingredients such as grain powders, vegetable oils, saccharides, and crystalline celluloses, and further, antioxidant(s) such as dibutylhydroxytoluene and nordihydroguaiaretic acid, preservative(s) such as dehydroacetic acid, accidental ingestion inhibitor(s) for children and pets such as chili powder, insect attraction fragrance(s) such as cheese flavor, onion flavor, and peanut oil, or the other ingredient(s) may be added thereto as needed.

The method for controlling harmful arthropods of the present invention is carried out by applying an effective amount of the Present compound to harmful arthropods directly and/or habitats of pests (for example, plant bodies, soil, interiors of houses, or animal bodies). Also, the Present compound may be applied to seeds. In the method for controlling harmful arthropods of the present invention, the Present compound is usually used in the form of the composition for controlling harmful arthropods of the present invention.

When the composition for controlling harmful arthropods of the present invention is used for controlling pests in an agricultural field, the application dose as an amount of the Present compound is usually within the range from 1 to 10,000 g per 10,000 m$^2$. When the composition for controlling harmful arthropods of the present invention is applied to seeds, the application dose as an amount of the Present compound is usually within the range from 0.001 to 100 g per 1 Kg of the seeds. The emulsifiable concentrate, the wettable powder, the flowable, or the like of the composition for controlling harmful arthropods of the present invention is usually applied by diluting it with water in such a way that a concentration of the active ingredient is within a range from 0.01 to 10,000 ppm. The granule, the dust formulation, or the like is usually applied as itself without diluting it.

These formulations and diluents of the formulations with water may be directly sprayed to harmful arthropods or plants such as crops to be protected from harmful arthropods, or applied to soil in cultivated areas to control pests that inhabit the soil.

Also, a resin formulation processed into a sheet shape or a string shape may be wrapped around crops, stretched near crops, spread on plant foot soil, or the like.

When the composition for controlling harmful arthropods of the present invention is used to control pests that live inside a house, the application dose as an amount of the Present compound is usually within a range from 0.01 to 1,000 mg per 1 m² of an area to be treated in the case of using it on a planar area. In the case of using it spatially, the application dose as an amount of the Present compound is usually within a range from 0.01 to 500 mg per 1 m³ of the space to be treated. When the composition for controlling harmful arthropods of the present invention is formulated into an emulsifiable concentrate, a wettable powder, a flowable, or the others, such formulation is usually applied after diluting it with water in such a way that a concentration of the active ingredient is within a range from 0.1 to 10,000 ppm, and then sparging it. In the case of being formulated into an oil solution, an aerosol, a smoking agent, a poison bait, or the others, such formulation is used as itself without diluting it.

When the composition for controlling harmful arthropods of the present invention is used for controlling external parasites of livestock such as cows, horses, pigs, sheep, goats, and chickens, and small animals such as dogs, cats, rats, and mice, the composition of the present invention may be applied to the animals by a known method in the veterinary field. Specifically, when systemic control is intended, the composition of the present invention is administered to the animals as a tablet, a mixture with feed, or a suppository, or by injection (including intramuscular, subcutaneous, intravenous, and intraperitoneal injections), or the like. On the other hand, when non-systemic control is intended, the composition of the present invention is applied to the animals by means of spraying of the oil solution or aqueous solution, pour-on or spot-on treatment, or washing of the animal with a shampoo formulation, or by putting a collar or an ear tag made of the resin formulation to the animal, or the like. In the case of administering to an animal body, the amount of the Present compound is usually within the range from 0.1 to 1,000 mg per 1 kg of the animal body weight.

Also, the Present compound may be used as an agent for controlling harmful arthropods in croplands such as fields, paddy fields, grasses, and orchards. The Present compound can control harmful arthropods in the croplands etc. for cultivating the following plant(s) etc.

Crops: corn, rice, wheat, barley, rye, oat, sorghum, cotton, soybean, peanut, buckwheat, beet, rapeseed, sunflower, sugar cane, tobacco, and the others; Vegetables: solanaceous vegetables (for example, eggplant, tomato, pimento, pepper, or potato), cucurbitaceous vegetables (for example, cucumber, pumpkin, zucchini, water melon, or melon), cruciferous vegetables (for example, Japanese radish, white turnip, horseradish, kohlrabi, Chinese cabbage, cabbage, leaf mustard, broccoli, or cauliflower), asteraceous vegetables (for example, burdock, crown daisy, artichoke, or lettuce), liliaceous vegetables (for example, welsh onion, onion, garlic, or asparagus), ammiaceous vegetables (for example, carrot, parsley, celery, or parsnip), chenopodiaceous vegetables (for example, spinach or Swiss chard), lamiaceous vegetables (for example, perilla, mint, or basil), strawberry, sweet potato, glutinous yam, eddoe, and the others; Flowers; Foliage plants; Fruits: pomaceous fruits (for example, apple, pear, Japanese pear, Chinese quince, or quince), stone fleshy fruits (for example, peach, plum, nectarine, Japanese apricot (*Prunus mume*), cherry fruit, apricot, or prune), citrus fruits (for example, Citrus unshiu, orange, lemon, lime, or grapefruit), nuts (for example, chestnuts, walnuts, hazelnuts, almond, pistachio, cashew nuts, or macadamia nuts), berry fruits (for example, blueberry, cranberry, blackberry, or raspberry), grapes, Japanese persimmon, olive, Japanese plum, banana, coffee, date palm, coconuts, and the others; and Trees other than fruit trees: tea, mulberry, flowering plants, roadside trees (for example, ash, birch, dogwood, eucalyptus, ginkgo (*Ginkgo biloba*), lilac, maple, oak (*Quercus*), poplar, Judas tree, Formosan gum (*Liquidambar formosana*), plane tree, zelkova, Japanese arborvitae (*Thuja standishii*), fir wood, hemlock, juniper, pinus, picea, or yew (*Taxus cuspidate*)), and the others.

The above-mentioned "plant(s)" may be genetically modified plant(s).

EXAMPLES

The following Examples including Preparation Examples, Formulation Examples, and Test Examples serve to illustrate the present invention more in detail, which should not intend to limit the present invention.

First, Preparation Examples of the Present compound are shown below.

Reference Preparation Example 1-1

A mixture of 2-(5-bromo-3-ethanesulfonylpyridin-2-yl)-3-methyl-6-trifluoromethyl-3H-imidazo[4,5-b]pyridine (9.0 g), bis(pinacolato)diboron (5.6 g), [1,1'-bis(diphenylphosphino)ferrocene]palladium(II) dichloride dichloromethane adduct (0.49 g), potassium acetate (5.9 g), and DMSO (80 mL) was stirred under nitrogen atmosphere at 90° C. for 10 hours. To the resulting mixture was added water at room temperature, and the resulting mixture was extracted with chloroform. The resulting organic layer was washed with saturated brine, dried over anhydrous magnesium sulfate, and concentrated under reduced pressure to give the Intermediate compound (1) represented by the following formula (8.1 g).

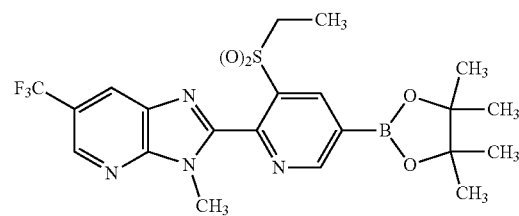

Intermediate Compound (1)

¹H-NMR (CDCl₃) δ: 9.27 (1H, d, J=1.4 Hz), 8.87 (1H, d, J=1.4 Hz), 8.76 (1H, d, J=1.8 Hz), 8.31 (1H, d, J=1.8 Hz), 3.87 (3H, s), 3.82 (2H, q, J=7.5 Hz), 1.42 (12H, s), 1.38 (3H, t, J=7.5 Hz).

Reference Preparation Example 1-2

The compound prepared according to the method described in the Reference Preparation Example 1-1 and the physical property thereof are shown below.

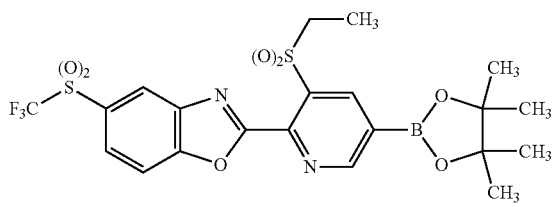

Intermediate Compound (2)

¹H-NMR (CDCl₃) δ: 9.31 (1H, d, J=1.4 Hz), 8.94 (1H, d, J=1.6 Hz), 8.60 (1H, d, J=1.6 Hz), 8.19 (1H, dd, J=8.6, 1.6 Hz), 7.99 (1H, d, J=8.6 Hz), 3.98 (2H, q, J=7.5 Hz), 1.49 (3H, t, J=7.5 Hz), 1.43 (12H, s).

Reference Preparation Example 2-1

To a mixture of the Intermediate compound (1) (0.99 g), sodium acetate (1.2 g), THF (8 mL), and water (4 mL) was added 30% hydrogen peroxide water (1.1 mL), and the resulting mixture was stirred at 0° C. for 6 hours. To the resulting mixture was added saturated sodium thiosulfate (30 mL), and the resulting mixture was stirred for 1 hour. To the resulting mixture was added a saturated aqueous solution of sodium hydrogen carbonate at room temperature, and the resulting mixture was extracted with chloroform. The resulting organic layer was washed with saturated brine, dried over anhydrous magnesium sulfate, and concentrated under reduced pressure. The resulting residue was subjected to silica gel chromatography to give the Intermediate compound (3) represented by the following formula (0.46 g).

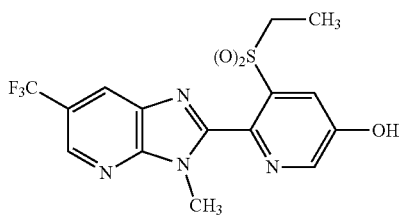

Intermediate Compound (3)

¹H-NMR (CDCl₃) δ: 8.78-8.76 (1H, m), 8.49 (1H, d, J=2.7 Hz), 8.33-8.31 (1H, m), 7.87 (1H, d, J=2.7 Hz), 3.84 (3H, s), 3.70 (2H, q, J=7.5 Hz), 1.36 (3H, t, J=7.5 Hz).

Reference Preparation Example 2-2

The compound prepared according to the method described in the Reference Preparation Example 2-1 and the physical property thereof are shown below.

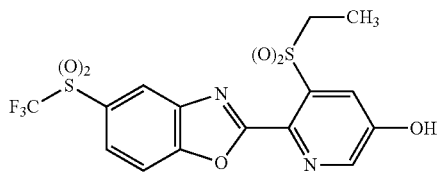

Intermediate Compound (4)

¹H-NMR (CDCl₃) δ: 8.62 (1H, d, J=2.5 Hz), 8.55-8.53 (1H, m), 8.15-8.11 (1H, m), 8.02 (1H, d, J=2.5 Hz), 7.94-7.90 (1H, m), 4.03 (2H, q, J=7.5 Hz), 1.44 (3H, t, J=7.5 Hz).

Reference Preparation Example 3-1

To a mixture of 5-bromo-3-(ethylthio)pyridine-2-carboxylic acid (5.2 g), THF (80 mL), and DMF (0.1 mL) was added oxalyl chloride (3 mL) under ice-cooling, and the resulting mixture was stirred at room temperature for 1 hour. The resulting mixture was concentrated under reduced pressure. To the resulting residue were added chloroform (80 mL) and N-methyl-1,1,3,3-tetrafluoro-1,3-dihydroisobenzofuran-5,6-diamine (4.7 g), triethylamine (5.6 mL) was added thereto under ice-cooling, and the resulting mixture was stirred at room temperature for 2 hours. To the resulting mixture was added water, and the resulting mixture was extracted with chloroform. The resulting organic layer was washed with saturated brine, dried over anhydrous magnesium sulfate, and concentrated under reduced pressure to give a crude product of the Intermediate compound (5) represented by the following formula (9.8 g).

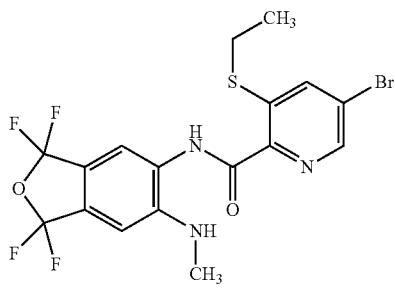 [SMILES: CCSc1cc(Br)cnc1C(=O)Nc1cc2c(cc1NC)C(F)(F)OC2(F)F]

Intermediate Compound (5)

¹H-NMR (CDCl₃) δ: 9.68 (1H, s), 8.37 (1H, d, J=1.8 Hz), 7.99 (1H, s), 7.83 (1H, d, J=1.8 Hz), 7.65 (1H, d, J=1.8 Hz), 3.85 (1H, s), 3.04 (2H, q, J=7.3 Hz), 2.97 (3H, s), 1.35 (3H, t, J=7.3 Hz).

Reference Preparation Example 3-2

A mixture of the crude product of the Intermediate compound (5) (9.8 g) and acetic acid (40 mL) was stirred under reflux for 5 hours. The mixture was cooled to room temperature, and then concentrated under reduced pressure. To the resulting residue was added a saturated aqueous solution of sodium hydrogen carbonate, and the resulting mixture was extracted with ethyl acetate. The resulting organic layer was washed with saturated brine, dried over anhydrous magnesium sulfate, and concentrated under reduced pressure to give the Intermediate compound (6) represented by the following formula (7.4 g).

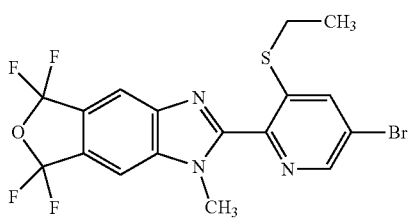 [SMILES: CCSc1cc(Br)cnc1-c1nc2cc3c(cc2n1C)C(F)(F)OC3(F)F]

Intermediate Compound (6)

$^1$H-NMR (CDCl$_3$) δ: 8.55 (1H, d, J=2.0 Hz), 8.12 (1H, s), 7.87 (1H, d, J=2.0 Hz), 7.70 (1H, s), 4.01 (3H, s), 2.97 (2H, q, J=7.4 Hz), 1.37 (3H, t, J=7.4 Hz).

Reference Preparation Example 3-3

To a mixture of the Intermediate compound (6) (7.2 g) and chloroform (50 mL) was added m-chloroperoxybenzoic acid (8.6 g) under ice-cooling, and the resulting mixture was stirred at room temperature for 6 hours. To the resulting mixture was added an aqueous solution of sodium thiosulfate, and the resulting mixture was stirred at room temperature for 1 hour. To the resulting mixture was added a saturated aqueous solution of sodium hydrogen carbonate, and the resulting mixture was extracted with chloroform. The resulting organic layer was washed with saturated brine, dried over anhydrous magnesium sulfate, and concentrated under reduced pressure to give the Intermediate compound (7) represented by the following formula (7.5 g).

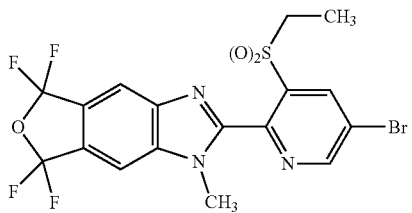

Intermediate Compound (7)

$^1$H-NMR (CDCl$_3$) δ: 9.05 (1H, d, J=2.1 Hz), 8.67 (1H, d, J=2.1 Hz), 8.04 (l, s), 7.73 (l, s), 3.85 (2H, q, J=7.4 Hz), 3.85 (3H, s), 1.39 (3H, t, J=7.4 Hz).

Reference Preparation Example 4

To a mixture of 2-bromo-1-[5-bromo-3-(ethanesulfonyl)pyridin-2-yl]ethanone (6.0 g) and ethanol (54 mL) was added 2-amino-4-(trifluoromethyl)pyridine (17.8 mL) at room temperature, and the resulting mixture was stirred under reflux for 8 hours. The resulting mixture was cooled to room temperature, and then concentrated under reduced pressure. To the resulting residue was added water, and resulting mixture was extracted with ethyl acetate. The resulting organic layer was washed with saturated brine, dried over anhydrous magnesium sulfate, and concentrated under reduced pressure to give the Intermediate compound (8) represented by the following formula (3.7 g).

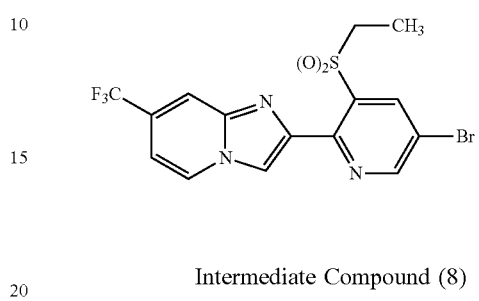

Intermediate Compound (8)

$^1$H-NMR (CDCl$_3$) δ: 8.93 (1H, d, J=2.1 Hz), 8.68 (1H, d, J=2.1 Hz), 8.32-8.27 (2H, m), 7.97-7.95 (1H, m), 7.07-7.03 (1H, m), 4.02 (2H, q, J=7.6 Hz), 1.38 (3H, t, J=7.6 Hz).

Preparation Example 1

A mixture of 2-(5-fluoro-3-ethanesulfonylpyridin-2-yl)-3-methyl-6-trifluoromethyl-3H-imidazo[4,5-b]pyridine (0.23 g), 3-hydroxypyridine (0.057 g), cesium carbonate (0.39 g), and DMF (3 mL) was stirred at room temperature for 2 hours. To the mixture was added water at room temperature, and the resulting mixture was extracted with ethyl acetate. The resulting organic layer was washed with saturated brine, dried over anhydrous sodium sulfate, and concentrated under reduced pressure. The resulting residue was subjected to silica gel chromatography (hexane:ethyl acetate=3:1) to give the Present compound 1 represented by the following formula (0.12 g).

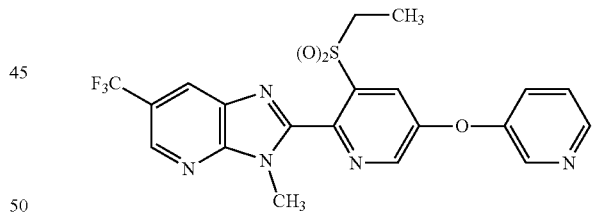

Present Compound 1

$^1$H-NMR (CDCl$_3$) δ: 8.80-8.78 (1H, m), 8.76 (1H, d, J=2.7 Hz), 8.65-8.62 (1H, m), 8.61 (1H, d, J=2.7 Hz), 8.34-8.32 (1H, m), 8.07 (1H, d, J=2.7 Hz), 7.58-7.54 (1H, m), 7.51-7.47 (1H, m), 3.92 (3H, s), 3.88 (2H, q, J=7.4 Hz), 1.38 (3H, t, J=7.4 Hz).

Preparation Example 2

The compounds prepared according to the method described in the Preparation Example 1 and the physical properties thereof are shown below.

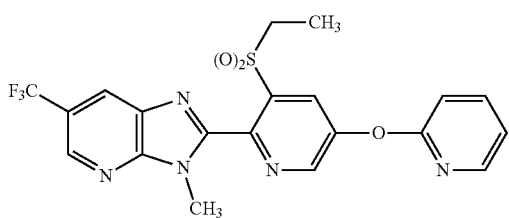

Present Compound 2

¹H-NMR (CDCl₃) δ: 8.80-8.78 (1H, m), 8.76 (1H, d, J=2.7 Hz), 8.65-8.62 (1H, m), 8.61 (1H, d, J=2.7 Hz), 8.34-8.32 (1H, m), 8.07 (1H, d, J=2.7 Hz), 7.58-7.54 (1H, m), 7.51-7.47 (1H, m), 3.92 (3H, s), 3.88 (2H, q, J=7.4 Hz), 1.38 (3H, t, J=7.4 Hz).

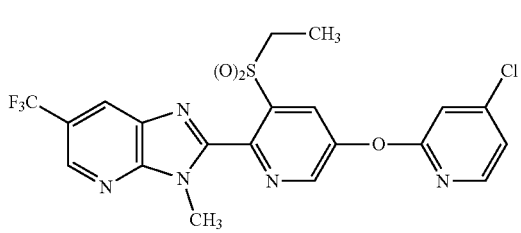

Present Compound 3

¹H-NMR (CDCl₃) δ: 8.90 (1H, d, J=2.5 Hz), 8.81-8.78 (1H, m), 8.40 (1H, d, J=2.5 Hz), 8.35-8.33 (1H, m), 8.14-8.12 (1H, m), 7.22-7.20 (2H, m), 3.95 (3H, s), 3.90 (2H, q, J=7.4 Hz), 1.42 (3H, t, J=7.4 Hz).

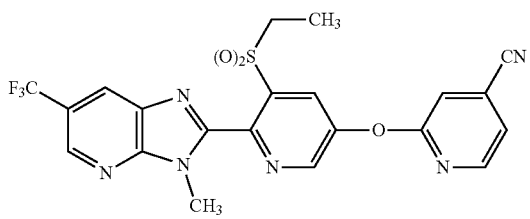

Present Compound 4

¹H-NMR (CDCl₃) δ: 8.92 (1H, d, J=2.5 Hz), 8.81-8.79 (1H, m), 8.42 (1H, d, J=2.5 Hz), 8.39-8.37 (1H, m), 8.36-8.33 (1H, m), 7.44-7.41 (2H, m), 3.95 (3H, s), 3.92 (2H, q, J=7.5 Hz), 1.42 (3H, t, J=7.5 Hz).

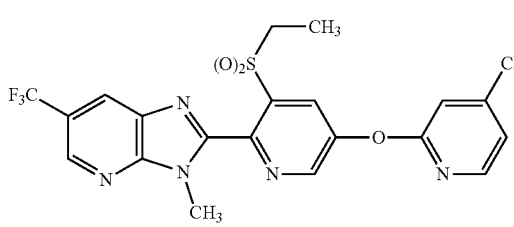

Present Compound 5

¹H-NMR (CDCl₃) δ: 8.93 (1H, d, J=2.5 Hz), 8.81-8.79 (1H, m), 8.43 (1H, d, J=2.5 Hz), 8.41-8.37 (1H, m), 8.36-8.33 (1H, m), 7.44-7.40 (2H, m), 3.96 (3H, s), 3.92 (2H, q, J=7.4 Hz), 1.43 (3H, t, J=7.4 Hz).

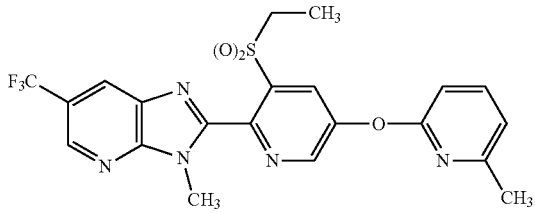

Present Compound 6

¹H-NMR (CDCl₃) δ: 8.89 (1H, d, J=2.7 Hz), 8.80-8.77 (1H, m), 8.40 (1H, d, J=2.7 Hz), 8.35-8.32 (1H, m), 7.77-7.71 (1H, m), 7.07-7.03 (1H, m), 6.96-6.93 (1H, m), 3.94 (3H, s), 3.88 (2H, q, J=7.5 Hz), 2.46 (3H, s), 1.43 (3H, t, J=7.5 Hz).

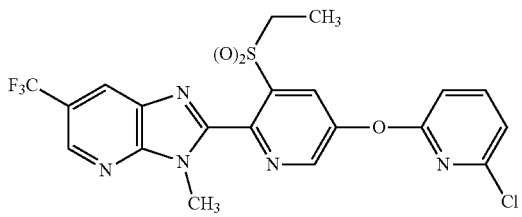

Present Compound 7

¹H-NMR (CDCl₃) δ: 8.91 (1H, d, J=2.5 Hz), 8.80-8.77 (1H, m), 8.41 (1H, d, J=2.5 Hz), 8.35-8.33 (1H, m), 7.84-7.78 (1H, m), 7.23-7.19 (1H, m), 7.10-7.05 (1H, m), 3.95 (3H, s), 3.90 (2H, q, J=7.4 Hz), 1.44 (3H, t, J=7.4 Hz).

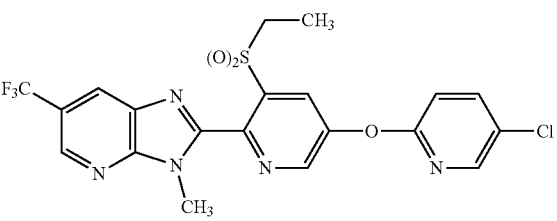

Present Compound 8

¹H-NMR (CDCl₃) δ: 8.90 (1H, d, J=2.5 Hz), 8.81-8.78 (1H, m), 8.38 (1H, d, J=2.5 Hz), 8.35-8.33 (1H, m), 8.19-8.16 (1H, m), 7.86-7.81 (1H, m), 7.17-7.13 (1H, m), 3.94 (3H, s), 3.90 (2H, q, J=7.5 Hz), 1.42 (3H, t, J=7.5 Hz).

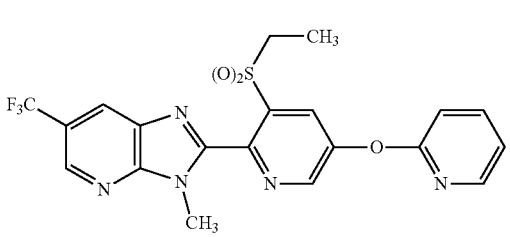

Present Compound 9

¹H-NMR (CDCl₃) δ: 9.04 (1H, d, J=2.3 Hz), 8.80-8.78 (1H, m), 8.67 (1H, d, J=2.3 Hz), 8.49-8.45 (1H, m), 8.36-8.32 (1H, m), 7.75-7.68 (1H, m), 7.45-7.40 (1H, m), 7.26-7.21 (1H, m), 3.95 (3H, s), 3.89 (2H, q, J=7.4 Hz), 1.42 (3H, t, J=7.4 Hz).

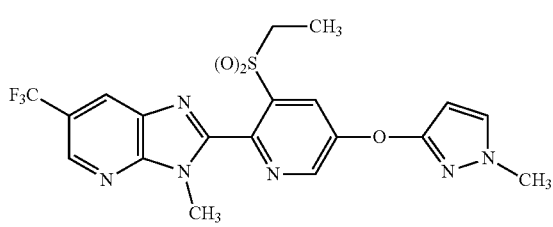

Present Compound 10

¹H-NMR (CDCl₃) δ: 8.85 (1H, d, J=2.7 Hz), 8.76-8.73 (1H, m), 8.31-8.28 (1H, m), 8.27 (1H, d, J=2.7 Hz), 7.36 (1H, d, J=2.3 Hz), 5.98 (1H, d, J=2.3 Hz), 3.87 (3H, s), 3.86 (3H, s), 3.83 (2H, q, J=7.4 Hz), 1.35 (3H, t, J=7.4 Hz).

Preparation Example 3

A mixture of the Intermediate compound (3) (0.31 g), 2-(bromomethyl)pyridine hydrobromide (0.20 g), cesium carbonate (0.78 g), and DMF (4 mL) was stirred at 60° C. for 4 hours. To the resulting mixture was added water at room temperature, and the resulting mixture was extracted with chloroform. The resulting organic layer was washed with saturated brine, dried over anhydrous magnesium sulfate, and concentrated under reduced pressure. The resulting residue was subjected to silica gel chromatography (hexane:ethyl acetate=2:1) to give the Present compound 11 represented by the following formula (0.10 g).

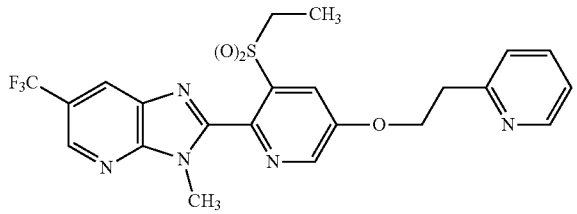

Present Compound 11

¹H-NMR (CDCl₃) δ: 8.75-8.72 (2H, m), 8.67-8.64 (1H, m), 8.29-8.27 (1H, m), 8.10 (1H, d, J=2.7 Hz), 7.82-7.77 (1H, m), 7.53 (1H, d, J=7.9 Hz), 7.34-7.29 (1H, m), 5.43 (2H, s), 3.84 (3H, s), 3.80 (2H, q, J=7.5 Hz), 1.31 (3H, t, J=7.5 Hz).

Preparation Example 4-1

A mixture of the Intermediate compound (4) (0.30 g), 2-bromopyridine (0.11 g), copper(I) iodide (0.013 g), 1-butylimidazole (0.43 g), potassium carbonate (0.19 g), and toluene (4 mL) was stirred under reflux for 24 hours. To the resulting mixture was added water at room temperature, and the resulting mixture was extracted with chloroform. The resulting organic layer was washed with saturated brine, dried over anhydrous magnesium sulfate, and concentrated under reduced pressure. The resulting residue was subjected to silica gel chromatography (hexane:ethyl acetate=2:1) to give the Present compound 12 represented by the following formula (0.080 g).

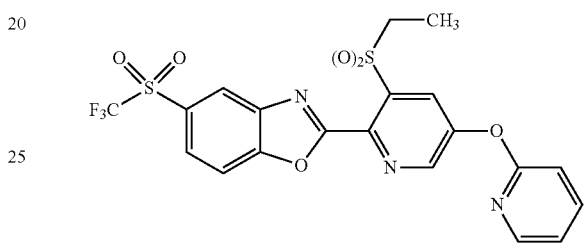

Present Compound 12

¹H-NMR (CDCl₃) δ: 8.94 (1H, d, J=2.5 Hz), 8.60-8.57 (1H, m), 8.46 (1H, d, J=2.5 Hz), 8.24-8.19 (1H, m), 8.19-8.15 (1H, m), 7.99-7.94 (1H, m), 7.90-7.84 (1H, m), 7.22-7.18 (1H, m), 7.17-7.14 (1H, m), 4.03 (2H, q, J=7.5 Hz), 1.48 (3H, t, J=7.5 Hz).

Preparation Example 4-2

The compound prepared according to the method described in the Preparation Example 4-1 and the physical property thereof are shown below.

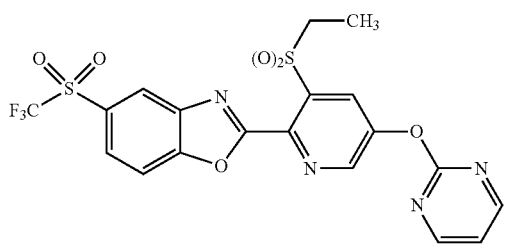

Present Compound 13

¹H-NMR (CDCl₃) δ: 8.99 (1H, d, J=2.5 Hz), 8.67 (2H, d, J=4.8 Hz), 8.61-8.59 (1H, m), 8.55 (1H, d, J=2.5 Hz), 8.21-8.16 (1H, m), 7.98 (1H, d, J=8.7 Hz), 7.26-7.23 (1H, m), 4.05 (2H, q, J=7.5 Hz), 1.48 (3H, t, J=7.5 Hz).

Preparation Example 5-1

A mixture of the Intermediate compound (7) (0.49 g), 2-hydroxypyridine (0.095 g), copper(I) iodide (0.019 g), 1-butylimidazole (0.62 g), potassium carbonate (0.28 g), and toluene (4 mL) was stirred under reflux for 48 hours. To the resulting mixture was added water at room temperature, and the resulting mixture was extracted with ethyl acetate. The resulting organic layer was washed with saturated brine, dried over anhydrous magnesium sulfate, and concentrated under reduced pressure. The resulting residue was subjected to silica gel chromatography (hexane:ethyl acetate=3:1) to give the Present compound 14 represented by the following formula (0.062 g).

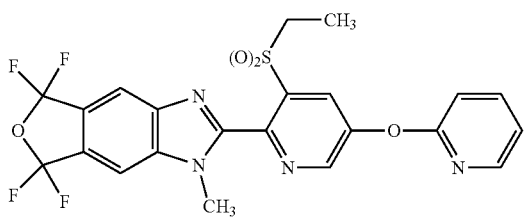

Present Compound 14

$^1$H-NMR (CDCl$_3$) δ: 8.88 (1H, d, J=2.5 Hz), 8.37 (1H, d, J=2.5 Hz), 8.21-8.20 (1H, m), 8.03 (1H, s), 7.88-7.83 (1H, m), 7.73 (1H, s), 7.20-7.16 (1H, m), 7.16-7.13 (1H, m), 3.87-3.79 (5H, m), 1.38 (3H, t, J=7.4 Hz).

Preparation Example 5-2

The compound prepared according to the method described in the Preparation Example 5-1 and the physical property thereof are shown below.

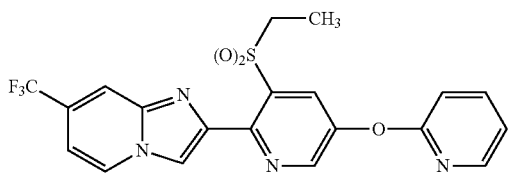

Present Compound 15

$^1$H-NMR (CDCl$_3$) δ: 8.80 (1H, d, J=2.5 Hz), 8.38 (1H, d, J=2.5 Hz), 8.31-8.28 (2H, m), 8.19-8.17 (1H, m), 7.97-7.95 (1H, m), 7.83-7.78 (1H, m), 7.14-6.98 (3H, m), 3.95 (2H, q, J=7.5 Hz), 1.37 (3H, t, J=7.5 Hz).

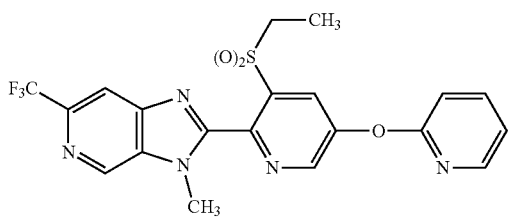

Present Compound 16

$^1$H-NMR (CDCl$_3$) δ: 8.99 (1H, s), 8.89 (1H, d, J=2.5 Hz), 8.37 (1H, d, J=2.5 Hz), 8.21-8.20 (1H, m), 8.11 (1H, s), 7.88-7.82 (1H, m), 7.20-7.09 (2H, m), 3.93 (3H, s), 3.81 (2H, q, J=7.4 Hz), 1.38 (3H, t, J=7.4 Hz).

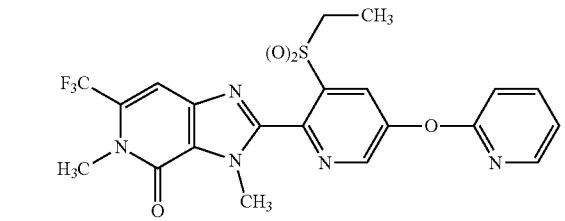

Present Compound 17

$^1$H-NMR (CDCl$_3$) δ: 8.86 (1H, d, J=2.7 Hz), 8.33 (1H, d, J=2.7 Hz), 8.21-8.19 (1H, m), 7.87-7.81 (1H, m), 7.22 (1H, d, J=2.5 Hz), 7.19-7.12 (2H, m), 4.10 (3H, s), 3.77 (2H, q, J=7.5 Hz), 3.73 (3H, s), 1.36 (3H, t, J=7.5 Hz).

Next, the Formulation Examples of the Present compound are shown below. The "part(s)" represents "part(s) by weight".

Formulation Example 1

Any one of the Present compounds 1 to 17 (10 parts) is mixed with a mixture of xylene (35 parts) and DMF (35 parts), and then polyoxyethylene styryl phenyl ether (14 parts) and calcium dodecylbenzene sulfonate (6 parts) are added thereto, followed by mixing them to obtain each formulation.

Formulation Example 2

Sodium lauryl sulfate (4 parts), calcium lignin sulfonate (2 parts), wet silica (20 parts), and diatomaceous earth (54 parts) are mixed, and further any one of the Present compounds 1 to 17 (20 parts) is added thereto, followed by mixing them to obtain each formulation.

Formulation Example 3

To any one of the Present compounds 1 to 17 (2 parts) are added wet silica (1 part), calcium lignin sulfonate (2 parts), bentonite (30 parts), and kaolin clay (65 parts), followed by mixing them to obtain a mixture. To the mixture is then added an appropriate amount of water, the resulting mixture is additionally stirred, and subjected to granulation with a granulator and forced-air drying to obtain each formulation.

Formulation Example 4

Any one of the Present compounds 1 to 17 (1 part) is mixed with an appropriate amount of acetone, and then wet silica (5 parts), acidic isopropyl phosphate (0.3 part), and kaolin clay (93.7 parts) are added thereto, followed by mixing with stirring thoroughly and removal of acetone from the mixture by evaporation to obtain each formulation.

Formulation Example 5

A mixture of polyoxyethylene alkyl ether sulfate ammonium salt and wet silica (weight ratio of 1:1) (35 parts), any one of the Present compounds 1 to 17 (20 parts), and water (45 parts) are thoroughly mixed to obtain each formulation.

Formulation Example 6

Any one of the Present compounds 1 to 17 (0.1 part) is mixed with a mixture of xylene (5 parts) and trichloroethane (5 parts), and the resulting mixture is then mixed with kerosene (89.9 parts) to obtain each formulation.

Formulation Example 7

Any one of the Present compounds 1 to 17 (10 mg) is mixed with acetone (0.5 mL), and the solution is added dropwise to a solid feed powder for an animal (solid feed powder for rearing and breeding CE-2, manufactured by CLEA Japan, Inc.) (5 g), followed by mixing the resulting mixture uniformly, and then by drying it by evaporation of acetone to obtain each poison bait.

Formulation Example 8

Any one of the Present compounds 1 to 17 (0.1 part) and Neothiozole (manufactured by Chuo Kasei Co., Ltd.) (49.9 parts) are placed into an aerosol can. After mounting an aerosol valve, dimethyl ether (25 parts) and LPG (25 parts) are filled, followed by shaking and further mounting an actuator to obtain each oily aerosol.

Formulation Example 9

A mixture of any one of the Present compounds 1 to 17 (0.6 part), 2,6-di-tert-butyl-4-methylphenol (0.01 part), xylene (5 parts), kerosene (3.39 parts), and an emulsifier {Rheodol MO-60 (manufactured by Kao Corporation)} (1 part), and distilled water (50 parts) are filled into an aerosol container, and a valve part is attached. Then, a propellant (LPG) (40 parts) is filled therein through the valve under pressure to obtain each aqueous aerosol.

Formulation Example 10

Any one of the Present compounds 1 to 17 (0.1 g) is mixed with propylene glycol (2 mL), and the resulting solution is impregnated into a ceramic plate having a size of 4.0 cm×4.0 cm and a thickness of 1.2 cm to obtain each thermal smoking agent.

Formulation Example 11

Any one of the Present compounds 1 to 17 (5 parts) and ethylene-methyl methacrylate copolymer (the ratio of the methyl methacrylate relative to the total weight of the copolymer: 10% by weight, Acryft (registered trademark) WD 301, manufactured by Sumitomo Chemical Co. Ltd.) (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 12

Any one of the Present compounds 1 to 17 (5 parts) and flexible vinyl chloride resin (95 parts) are melted and kneaded with a closed type pressure kneader (manufactured by Moriyama Co., Ltd.), and the resulting kneaded product is extruded from an extrusion molding machine through a molding die to obtain each rod-shaped molded product having a length of 15 cm and a diameter of 3 mm.

Formulation Example 13

Any one of the Present compounds 1 to 17 (100 mg), lactose (68.75 mg), corn starch (237.5 mg), microcrystalline cellulose (43.75 mg), polyvinylpyrrolidone (18.75 mg), sodium carboxymethyl starch (28.75 mg), and magnesium stearate (2.5 mg) are mixed, and the resulting mixture is compressed to an appropriate size to obtain each tablet.

Formulation Example 14

Any one of the Present compounds 1 to 17 (25 mg), lactose (60 mg), corn starch (25 mg), carmellose calcium (6 mg), and an appropriate amount of 5% hydroxypropyl methylcellulose are mixed, and the resulting mixture is filled into a hard shell gelatin capsule or a hydroxypropyl methylcellulose capsule to obtain each capsule.

Formulation Example 15

To any one of the Present compounds 1 to 17 (100 mg), fumaric acid (500 mg), sodium chloride (2,000 mg), methylparaben (150 mg), propylparaben (50 mg), granulated sugar (25,000 mg), sorbitol (70% solution) (13,000 mg), Veegum K (manufactured by Vanderbilt Co.) (100 mg), perfume (35 mg), and colorant (500 mg) is added distilled water so that the final volume is set to be 100 mL, followed by mixing them to obtain each suspension for oral administration.

Formulation Example 16

Any one of the Present compounds 1 to 17 (5% by weight) is mixed with an emulsifier (5% by weight), benzyl alcohol (3% by weight), and propylene glycol (30% by weight), and phosphate buffer is added thereto so that the pH of the solution is set to be 6.0 to 6.5, and then water is added thereto as the rest parts to obtain each solution for oral administration.

Formulation Example 17

Aluminum distearate (5% by weight) is added to fractional distillated palm oil (57% by weight) and polysorbate 85 (3% by weight), and dispersed by heating. The resulting mixture is cooled to room temperature, and saccharin (25% by weight) is dispersed in the oil vehicle. Any one of the Present compounds 1 to 17 (10% by weight) is divided thereto to obtain each paste-like formulation for oral administration.

Formulation Example 18

Any one of the Present compounds 1 to 17 (5% by weight) is mixed with a limestone filler (95% by weight), followed by a wet granulation of the resulting mixture to obtain each granule for oral administration.

Formulation Example 19

Any one of the Present compounds 1 to 17 (5 parts) is mixed with diethylene glycol monoethyl ether (80 parts), propylene carbonate (15 parts) is added thereto, and the resulting mixture is mixed to obtain each spot-on solution.

Formulation Example 20

Any one of the Present compounds 1 to 17 (10 parts) is mixed with diethylene glycol monoethyl ether (70 parts), 2-octyldodecanol (20 parts) is added thereto, and the resulting mixture is mixed to obtain each pour-on solution.

Formulation Example 21

To any one of the Present compounds 1 to 17 (0.5 part) are added Nikkol (registered trademark) TEALS-42 (manufactured by Nikko Chemicals Co., Ltd.: a 42% aqueous solution of triethanolamine lauryl sulfate) (60 parts) and propylene glycol (20 parts), the resulting mixture is mixed with stirring thoroughly to obtain a homogeneous solution, water (19.5 parts) is then added thereto, and the resulting mixture is further mixed with stirring thoroughly to obtain each homogeneous solution of shampoo formulation.

Formulation Example 22

Any one of the Present compounds 1 to 17 (0.15% by weight), an animal feed (95% by weight), and a mixture (4.85% by weight) consisting of dibasic calcium phosphate, diatomaceous earth, Aerosil, and carbonate (or chalk) are mixed with stirring thoroughly to obtain each premix for an animal feed.

Formulation Example 23

Any one of the Present compounds 1 to 17 (7.2 g) and Hosco (registered trademark)S-55 (manufactured by Maruishi Pharmaceuticals) (92.8 g) are mixed at 100° C., and the resulting mixture is poured into a suppository mold, followed by performing a cooling solidification to obtain each suppository.

Next, Test Examples are used to show efficacies of the Present compounds on controlling harmful arthropods. In the following Test Examples, the tests were carried out at 25° C.

Test Example 1

Each test compound is formulated according to the process described in the Formulation Example 5 to obtain each formulation, and water containing a spreader (0.03% by volume) is added thereto to prepare a diluted solution containing a prescribed concentration of each test compound. Cucumber (*Cucumis sativus*) seedlings (on the developmental stage of the second true leaf) are planted in a container and approximately 30 cotton aphids (*Aphis gossypii*) (all stages of life) are released onto the cucumber seedlings. After 1 day, each of said diluted solutions is sprayed into the seedlings in a ratio of 10 mL/seedling. After additional 5 days, the number of the surviving insects is examined and the controlling value is calculated by the following equation.

Controlling value (%)={1−($Cb$×$Tai$)/($Cai$×$Tb$)}×100 wherein the symbols in the equation represent the following meanings.

$Cb$: Number of the test insects in untreated group;
$Cai$: Number of the surviving insects at the time of the investigation in untreated group;
$Tb$: Number of the test insects in treated group;
$Tai$: Number of the surviving insects at the time of the investigation in treated group Here the "untreated group" represents a group where a similar treatment procedure to that of the treated group except not using each test compound is done.

When the prescribed concentration was 500 ppm and each of the following Present compounds was used as a test compound to carry out a test according to the Test Example 1, each of the following Present compounds showed 90% or greater as the controlling value.

Present compounds: 1, 2, 6, 7, 8, 9, 10, 11, and 13

When the prescribed concentration was 200 ppm and each of the following Present compounds was used as a test compound to carry out a test according to the Test Example 1, each of the following Present compounds showed 90% or greater as the controlling value.

Present compounds: 2, 7, 8, 9, 10, 11, 12, 15, and 17

Test Example 2

Each test compound is formulated according to the process described in the Formulation Example 5 to obtain each formulation, and water is added thereto to prepare a diluted solution containing a prescribed concentration of each test compound.

Cucumber seedlings (on the developmental stage of the second true leaf) are planted in a container, and each of said diluted solutions is irrigated into the plant foot in a ratio of 5 mL/seedling. After 7 days, approximately 30 cotton aphids (*Aphis gossypii*) (all stages of life) are released onto the surfaces of leaves of the cucumber seedlings. After additional 6 days, the number of the surviving insects is examined and the controlling value is calculated by the following equation.

Controlling value (%)={1−($Cb$×$Tai$)/($Cai$×$Tb$)}×100 wherein the symbols in the equation represent the following meanings.

$Cb$: Number of the test insects in untreated group;
$Cai$: Number of the surviving insects at the time of the investigation in untreated group;
$Tb$: Number of the test insects in treated group;
$Tai$: Number of the surviving insects at the time of the investigation in treated group Here the "untreated group" represents a group where a similar treatment procedure to that of the treated group except not using each test compound is done.

When the prescribed concentration was 1000 ppm and each of the following Present compounds was used as a test compound to carry out a test according to the Test Example 2, each of the following Present compounds showed 90% or greater as the controlling value.

Present compounds: 2, 10, 11, and 17

Test Example 3

Each test compound is formulated according to the process described in the Formulation Example 5 to obtain each formulation, and water is added thereto to prepare a diluted solution containing a prescribed concentration of each test compound.

An artificial diet (Insecta LF, manufactured by Nosan Corporation) (7.7 g) is placed in a container, and thereto is irrigated each of said diluted solutions (2 mL). Five (5) the 4th instar larvae of cotton worm (*Spodoptera litura*) are released onto the artificial diet. After 5 days, the number of the surviving insects is counted, and the mortality of insects is calculated by the following equation.

Mortality (%)=(1−Number of surviving insects/5)×100

When the prescribed concentration was 500 ppm and each of the following Present compounds was used as a test compound to carry out a test according to the Test Example 3, each of the following Present compounds showed 80% or greater as the mortality.
Present compounds: 2, 7, 8, 9, and 13

Test Example 4

Each test compound is formulated according to the process described in the Formulation Example 5 to obtain each formulation, and water containing a spreader (0.03% by volume) is added thereto to prepare a diluted solution containing a prescribed concentration of each test compound.

Cabbage (*Brassicae oleracea*) seedlings (on the developmental stage of the second to third true leaf) are planted in a container, and each of said diluted solutions is sprayed into the seedlings in a ratio of 20 mL/seedling. Thereafter, the stem and leaf of the seedlings are cut out, and placed into a container lined with a filter paper.

Five (5) the 2nd instar larvae of diamondback moth (*Plutella xylostella*) are released into the container. After 5 days, the number of the surviving insects is counted, and the mortality of insects is calculated by the following equation.

Mortality (%)=(1−Number of surviving insects/5)×100

When the prescribed concentration was 500 ppm and each of the following Present compounds was used as a test compound to carry out a test according to the Test Example 4, each of the following Present compounds showed 80% or greater as the mortality.
Present compounds: 1, 2, 6, 7, 8, 9, 10, 11, and 13

Test Example 5

Each test compound is formulated according to the process described in the Formulation Example 5 to obtain each formulation, and water containing a spreader (0.03% by volume) is added thereto to prepare a diluted solution containing a prescribed concentration of each test compound. Cabbage seedlings (on the developmental stage of the third to fourth true leaf) are planted in a container, and each of said diluted solutions is sprayed into the seedlings in a ratio of 20 mL/seedling. Thereafter, 10 the 3rd instar larvae of diamondback moth (*Plutella xylostella*) are released into the cabbage seedlings. After 5 days, the number of the surviving insects is counted, and the mortality of insects is calculated by the following equation.

Mortality (%)=(1−Number of surviving insects/10)×100

When the prescribed concentration was 200 ppm and each of the following Present compounds was used as a test compound to carry out a test according to the Test Example 5, each of the following Present compounds showed 90% or greater as the mortality.
Present compounds: 2, 7, 8, 9, 10, 11, 12, 14, 15, and 17

Test Example 6

Each test compound is dissolved into a mixed solution (50 µL) of polyoxyethylene sorbitan mono-cocoate:acetone (at a volume ratio of polyoxyethylene sorbitan mono-cocoate:acetone=5:95) per 1 mg of the test compound, and water containing a spreader (0.03% by volume) is added thereto to prepare a diluted solution containing a prescribed concentration of each test compound.

Corns (*Zea mays*) are inoculated onto a tray lined with wet Kimwipes. After the corns are grown for 5 days, the entire seedlings of the corns are immersed into each of said diluted solutions for 30 seconds. Thereafter, two seedlings are placed into a petri dish (diameter: 90 mm), and 10 the 2nd instar larvae of western corn rootworm (*Diabrotica virgifera virgifera*) are released into the dish. After 5 days, the number of the dead insects is counted, and the mortality of insects is calculated by the following equation.

Mortality (%)=(Number of dead insects/10)×100

When the prescribed concentration was 500 ppm and each of the following Present compounds was used as a test compound to carry out a test according to the Test Example 6, each of the following Present compounds showed 80% or greater as the mortality.
Present compounds: 2, 7, 8, 11, and 16

Test Example 7

Each test compound is formulated according to the process described in the Formulation Example 5 to obtain each formulation, and water is added thereto to prepare a diluted solution containing a prescribed concentration of each test compound.

A filter paper having a diameter of 5.5 cm is lined with the inside bottom of a cup having a diameter of 5.5 cm, each of said diluted solutions (0.7 mL) is added dropwise on the filter paper, and sucrose (30 mg) is homogeneously placed into said cup as a feed. Ten (10) female adult house flies (*Musca domestica*) are released into said cup, and the cup is covered. After 24 hours, life and death of the house flies are examined, and the mortality is calculated by the following equation.

Mortality (%)=(Number of dead insects/Number of test insects)×100

When the prescribed concentration was 500 ppm and the following Present compound was used as a test compound to carry out a test according to the Test Example 7, the following Present compound showed 100% as the mortality.
Present compound: 1

Comparative Test Example 1

When the prescribed concentration was 250 ppm and each of the Present compound 2 and a compound represented by the following formula disclosed in WO 2013/018928 pamphlet (hereinafter referred to as "Comparative compound 1") was used as a test compound to carry out a test according to the Test Example 2, the Present compound 2 showed 100% as the mortality, while the Comparative compound 1 showed less than 30% as the mortality.

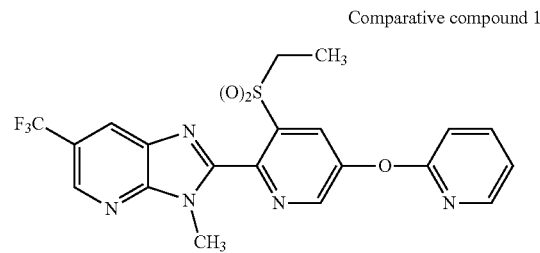

Comparative compound 1

INDUSTRIAL APPLICABILITY

The Present compounds have excellent control efficacies against harmful arthropods.

The invention claimed is:
1. A compound represented by formula (I)

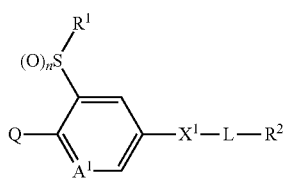

wherein:
Q represents a group represented by formula Q1, a group represented by formula Q2, a group represented by formula Q3, a group represented by formula Q4, a group represented by formula Q5, a group represented by formula Q6, or a group represented by formula Q7;

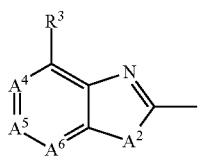

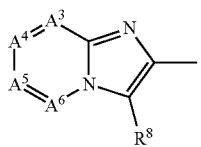

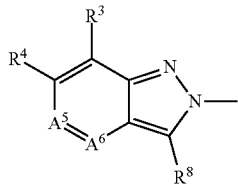

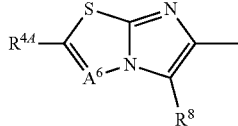

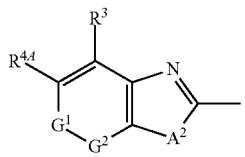

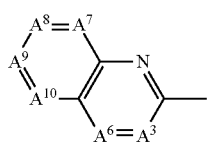

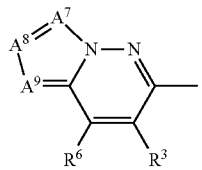

$A^1$ represents a $CR^7$ or a nitrogen atom;
$A^2$ represents a $NR^{8A}$, an oxygen atom, or a sulfur atom;
$A^3$ represents a nitrogen atom or a $CR^3$;
$A^4$ represents a nitrogen atom or a $CR^4$;
$A^5$ represents a nitrogen atom or a $CR^5$;
$A^6$ represents a nitrogen atom or a $CR^6$;
$A^7$ represents a nitrogen atom or a $CR^9$;
$A^8$ represents a nitrogen atom or a $CR^{10}$;
$A^9$ represents a nitrogen atom or a $CR^{11}$;
$A^{10}$ represents a nitrogen atom or a $CR^{12}$
provided that
in the group represented by formula Q1, $A^4$ and $A^5$ do not each simultaneously represent a nitrogen atom,
in the group represented by formula Q2, $A^3$, $A^4$, $A^5$, and $A^6$ do not each simultaneously represent a nitrogen atom,
in the group represented by formula Q6, $A^3$ and $A^6$ do not each simultaneously represent a nitrogen atom, and $A^7$, $A^8$, $A^9$, and $A^{10}$ do not each simultaneously represent a nitrogen atom, and
in the group represented by formula Q7, $A^7$, $A^8$, and $A^9$ do not each simultaneously represent a nitrogen atom;
$R^1$ represents a cyclopropyl group, a cyclopropylmethyl group, or a C1-C6 alkyl group optionally having one or more halogen atom(s);
$R^2$ represents a 5-10 membered heterocyclic group optionally having one or more substituent(s) selected from Group B;
$R^3$, $R^6$, $R^7$, and $R^9$ represent each independently a C1-C6 chain hydrocarbon group optionally having one or more halogen atom(s), a nitro group, a $OR^{13}$, a $NR^{14}R^{15}$, a cyano group, a halogen atom, or a hydrogen atom;
$R^{10}$, $R^{11}$, and $R^{12}$ represent each independently a C1-C6 chain hydrocarbon group optionally having one or more substituent(s) selected from Group C, a $OR^{16}$, a $S(O)_mR^{17}$, a $SF_5$, a halogen atom, or a hydrogen atom, wherein $R^{10}$ and $R^{11}$ do not each simultaneously represent a hydrogen atom;
$R^{4A}$ represents a C1-C6 chain hydrocarbon group optionally having one or more substituent(s) selected from Group C, a $OR^{16}$, a $S(O)_mR^{17}$, a $SF_5$, or a halogen atom;
when $A^4$ represents a $CR^4$ and $A^5$ represents a $CR^5$, then
$R^4$ represents a hydrogen atom, and $R^5$ represents a C1-C6 chain hydrocarbon group optionally having one or more substituent(s) selected from Group C, a $OR^{16}$, a $S(O)_mR^{17}$, a $SF_5$, or a halogen atom;
$R^5$ represents a hydrogen atom, and $R^4$ represents a C1-C6 chain hydrocarbon group optionally having one or more substituent(s) selected from Group C, a $OR^{16}$, a $S(O)_mR^{17}$, a $SF_5$, or a halogen atom; or
$R^4$ and $R^5$ may be combined with the carbon atom to which they are attached to form a benzene ring, a 5-6 membered aromatic heterocyclic ring, wherein said benzene ring and said 5-6 membered aromatic heterocyclic ring may optionally have one or more substituent(s) selected from Group B, or a 5-8 membered nonaromatic heterocyclic ring optionally having one or more substituent(s) selected from Group E;

when $A^4$ represents a nitrogen atom and $A^5$ represents a $CR^5$, then $R^5$ represents a C1-C6 chain hydrocarbon group optionally having one or more substituent(s) selected from Group C, a $OR^{16}$, a $S(O)_mR^{17}$, a $SF_5$, or a halogen atom;

when $A^5$ represents a nitrogen atom and $A^4$ represents a $CR^4$, then $R^4$ represents a C1-C6 chain hydrocarbon group optionally having one or more substituent(s) selected from Group C, a $OR^{16}$, a $S(O)_mR^{17}$, a $SF_5$, or a halogen atom;

$R^8$ represents a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{18}$, a $C(O)OR^{18}$, or a hydrogen atom;

$R^{8A}$ represents a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{18}$, or a $C(O)OR^{18}$;

$G^1$ represents a $NR^{19}$ and $G^2$ represents a $C(X^2)$; $G^1$ represents a $C(X^2)$ and $G^2$ represents a $NR^{19}$; or $G^1$ represents a $NR^{19}$ and $G^2$ represents a $NR^{20}$;

$R^{19}$ and $R^{20}$ represent each independently a C1-C6 chain hydrocarbon group optionally having one or more substituent(s) selected from Group D, a C3-C6 cycloalkyl group optionally having one or more halogen atom(s) or one or more C1-C3 alkyl group(s), a $C(O)R^{21}$, a $C(O)OR^{21}$, or a hydrogen atom;

$R^{13}$, $R^{14}$, $R^{15}$, $R^{16}$, $R^{17}$, $R^{18}$, and $R^{21}$ represent each independently a C1-C6 chain hydrocarbon group optionally having one or more halogen atom(s), or a hydrogen atom;

$X^1$ and $X^2$ represent each independently an oxygen atom or a sulfur atom;

L represents a single bond or a $CH_2$;

m and n represent each independently 0, 1, or 2;

Group B is selected from the group consisting of a C1-C6 chain hydrocarbon group optionally having one or more halogen atom(s), a hydroxy group, a C1-C6 alkoxy group optionally having one or more halogen atom(s), a C3-C6 alkenyloxy group optionally having one or more halogen atom(s), a C3-C6 alkynyloxy group optionally having one or more halogen atom(s), a sulfanyl group, a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a $N^{22}R^{23}$, a $C(O)R^{22}$, a $OC(O)R^{22}$, a $C(O)OR^{22}$, a cyano group, a nitro group, and a halogen atom, wherein $R^{22}$ and $R^{23}$ represent each independently a C1-C6 chain hydrocarbon group optionally having one or more halogen atom(s), or a hydrogen atom;

Group C is selected from the group consisting of a C1-C6 alkoxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C2-C6 alkylcarbonyl group optionally having one or more halogen atom(s), a C2-C6 alkoxycarbonyl group optionally having one or more halogen atom(s), a C3-C6 cycloalkyl group optionally having one or more halogen atom(s) or one or more C1-C3 alkyl group(s), a nitro group, a cyano group, a hydroxy group, and a halogen atom;

Group D is selected from the group consisting of a C1-C6 alkoxy group optionally having one or more halogen atom(s), a C1-C6 alkylsulfanyl group optionally having one or more halogen atom(s), a C1-C6 alkylsulfinyl group optionally having one or more halogen atom(s), a C1-C6 alkylsulfonyl group optionally having one or more halogen atom(s), a C2-C6 alkylcarbonyl group optionally having one or more halogen atom(s), a C2-C6 alkoxycarbonyl group optionally having one or more halogen atom(s), a C3-C6 cycloalkyl group optionally having one or more halogen atom(s) or one or more C1-C3 alkyl group(s), a phenyl group optionally having one or more substituent(s) selected from Group C, a 5-6 membered heterocyclic group optionally having one or more substituent(s) selected from Group C, a cyano group, a hydroxy group, and a halogen atom;

Group E is selected from the group consisting of a C1-C3 alkyl group optionally having one or more halogen atom(s), a C1-C3 alkoxy group optionally having one or more halogen atom(s), a $NR^{24}R^{25}$, a C1-C3 alkylsulfanyl group optionally having one or more halogen atom(s), a C1-C3 alkylsulfinyl group optionally having one or more halogen atom(s), a C1-C3 alkylsulfonyl group optionally having one or more halogen atom(s), a C2-C4 alkylcarbonyl group optionally having one or more halogen atom(s), a C2-C4 alkoxycarbonyl group optionally having one or more halogen atom(s), a nitro group, a cyano group, a halogen atom, an oxo group, a thioxo group, and a $=NOR^{26}$, wherein $R^{24}$ and $R^{25}$ represent each independently a hydrogen atom or a C1-C6 chain hydrocarbon group optionally having one or more halogen atom(s), and $R^{26}$ represents a C1-C6 alkyl group optionally having one or more halogen atom(s), or a hydrogen atom, wherein when Q represents a group represented by formula Q3 and $A^5$ represents a nitrogen atom, then $R^4$ represents a hydrogen atom or a C1-C6 chain hydrocarbon group optionally having one or more substituent(s) selected from Group C;

when Q represents a group represented by formula Q3 and $A^5$ represents a $CR^5$, then $R^4$ and $R^5$ each individually represent a hydrogen atom or a C1-C6 hydrocarbon group optionally having one or more substituent(s) selected from Group C, or $R^4$ and $R^5$ may be combined with the carbon atom to which they are attached to form a benzene ring, a 5-6 membered aromatic heterocyclic ring, wherein said benzene ring and said 5-6 membered heterocyclic ring may optionally have one or more substituent(s) selected from Group B, or a 5-8 membered nonaromatic heterocyclic ring optionally having one or more substituent(s) selected from Group E.

2. The compound according to claim 1, wherein Q represents a group represented by formula Q1.

3. The compound according to claim 1, wherein $A^4$ represents a $CR^4$, $X^1$ represents an oxygen atom, and L represents a single bond.

4. The compound according to claim 1, wherein $R^2$ represents a pyridyl group, a pyrimidinyl group, a pyrazinyl group, a pyridazinyl group, a pyrazolyl group, an imidazolyl group, a triazolyl group, an oxazolyl group, a thiazolyl group, a thiadiazolyl group, or an isoxazolyl group, wherein said pyridyl group, said pyrimidinyl group, said pyrazinyl group, said pyridazinyl group, said pyrazolyl group, said imidazolyl group, said triazolyl group, said oxazolyl group, said thiazolyl group, said thiadiazolyl group, and said isoxazolyl group optionally have one or more substituent(s) selected from Group B.

5. A composition for controlling a harmful arthropod comprising the compound according to claim 1 and an inert carrier.

6. A method for controlling a harmful arthropod which comprises applying an effective amount of the compound according to claim 1 to a harmful arthropod or a habitat where a harmful arthropod lives.

7. A composition comprising one or more ingredient(s) selected from the group consisting of Group (a), Group (b), Group (c), Group (d), and Group (e), and the compound according to claim 1;
  Group (a): a group consisting of an insecticidal active ingredient, a miticidal active ingredient, and a nematicidal active ingredient;
  Group (b): a fungicidal active ingredient;
  Group (c): a plant growth regulatory ingredient;
  Group (d): a phytotoxicity-reducing ingredient;
  Group (e): a synergist.

* * * * *